(12) United States Patent
Altier et al.

(10) Patent No.: US 7,064,184 B2
(45) Date of Patent: Jun. 20, 2006

(54) MAG1 ANTIMICROBIAL POLYPEPTIDES AND THEIR USES

(75) Inventors: Daniel J. Altier, Waukee, IA (US); Rafael Herrmann, Wilmington, DE (US); Albert L. Lu, Newark, DE (US); Billy F. McCutchen, Clive, IA (US); James K. Presnail, Avondale, PA (US); Janine L. Weaver, Bear, DE (US); James F.H. Wong, Johnston, IA (US)

(73) Assignees: Pioneer Hi-Bred International, Inc., Des Moines, IA (US); E. I. duPont de Nemours and Company, Wilmington, DE (US)

(*) Notice: Subject to any disclaimer, the term of this patent is extended or adjusted under 35 U.S.C. 154(b) by 81 days.

(21) Appl. No.: 11/093,225

(22) Filed: Mar. 29, 2005

(65) Prior Publication Data

US 2005/0164941 A1   Jul. 28, 2005

Related U.S. Application Data

(62) Division of application No. 10/125,258, filed on Apr. 18, 2002, now Pat. No. 6,891,085.

(60) Provisional application No. 60/285,355, filed on Apr. 20, 2001.

(51) Int. Cl.
*C07K 14/00* (2006.01)
*C07K 1/00* (2006.01)

(52) U.S. Cl. ........................... 530/350; 530/858
(58) Field of Classification Search ............... 530/350, 530/858
See application file for complete search history.

(56) References Cited

U.S. PATENT DOCUMENTS

| 5,436,392 | A | 7/1995 | Thomas et al. |
| 5,597,945 | A | 1/1997 | Jaynes et al. |
| 5,597,946 | A | 1/1997 | Jaynes et al. |
| 5,614,395 | A | 3/1997 | Ryals et al. |
| 5,811,654 | A | 9/1998 | Jaynes et al. |
| 6,100,453 | A | 8/2000 | Aldwinckle et al. |
| 6,750,381 | B1 | 11/2004 | Mitsuhara et al. |

FOREIGN PATENT DOCUMENTS

| JP | 11-255799 | | 9/1999 |
| WO | WO-94/05787 | A1 | 3/1994 |
| WO | WO 94/07356 | | 4/1994 |
| WO | WO 95/01430 | | 1/1995 |
| WO | WO-99/24594 | A1 | 5/1999 |
| WO | WO 99/53053 | A1 | 10/1999 |
| WO | WO-99/67357 | A2 | 12/1999 |

OTHER PUBLICATIONS

Allefs, S. J. H. M., et al., "Erwinia Soft Rot Resistance of Potato Cultivars Transformed with a Gene Construct Coding for Antimicrobial Peptide Cecropin B is not Altered," Aug. 1995, *Am. Potato J.*, pp. 437-445, vol. 72, No. 8.

Boman, H., et al., "On The Primary Structures of Lysozyme, Cecropins and Attacins from Hyalophora Cecropia," *Developmental and Comparative Immunology*, 1985, pp. 551-558, vol. 9.

Bulet, P., et al., "Insect Immunity. Isolation From a Coleopteran Insect of a Novel Inducible Antibacterial Peptide and of New Members of the Insect Defensin Family," *The Journal of Biological Chemistry*, 1991, pp. 24520-24525, vol. 266(36).

Bulet, P., et al., "Antimicrobial Peptides in Insects; Structure and Function," *Developmental and Comparative Immunology*, 1999, pp. 329-344, vol. 23.

Bulet, P., et al., "Antimicrobial Peptides in Insect Immunity," in: *Infectious Disease: Innate Immunity*, 2003, pp. 89-107, Ezekowitz et al., eds., Humana Press, Totowa, NJ.

Butler, M., et al., "The Aminopeptidase N-encoding pepN Gene of *Streptomyces lividians* 66," *Gene*, 1994, pp. 115-119, vol. 141(1), Elsevier Science B.V.

Cavallarin, L., et al., "Cecropin A-Derived Peptides Are Potent Inhibitors of Fungal Plant Pathogens," *Molecular Plant-Microbe Interactions*, 1998, pp. 218-227, vol. 11(3), The American Phytopathological Society, USA.

Chakrabarti, A., et al., "MSI-99, a Magainin Analogue, Imparts Enhanced Disease Resistance in Transgenic Tobacco and Banana," *Planta*, 2003, pp. 587-596, vol. 216.

Choi, C., et al., "Antibacterial Properties and Partial cDNA Sequences of Cecropin-Like Antibacterial Peptides From the Common Cutworm, *Spodoptera litura*," *Comparative Biochemistry and Physiology, Part C.*, 2000, pp. 287-297, vol. 125, Elsevier Science Inc.

Chowdhury, S., et al., "cDNA Cloning and Gene Expression of Lebocin, A Novel Member of Antibacterial Peptides from the Silkworm, *Bombyx mori*," *Biochemical and Biophysical Research Communications*, Sep. 1995, pp. 271-278, vol. 214(1), Academic Press, Inc.

(Continued)

Primary Examiner—Maryam Monshipouri
Assistant Examiner—Suzanne M. Mayer
(74) Attorney, Agent, or Firm—Alston & Bird LLP

(57) ABSTRACT

The methods and compositions of the present invention find use in impacting microbial pathogens and in enhancing disease resistance to pathogens, particularly by plants. The compositions of the invention include polypeptides that possess antimicrobial properties, particularly fungicidal properties, and the encoding nucleic acid molecules. The polypeptides of the invention are isolated from the hemolymph and fat bodies of insect larvae induced by injection of plant pathogenic fungi. Further provided are plant cells, plants, and seed thereof, transformed with the nucleic acid molecules of the invention so as to confer disease resistance on the plant.

6 Claims, 3 Drawing Sheets

OTHER PUBLICATIONS

De Bolle, M.F.C., et al., "Antimicrobial Peptides from *Mirabilis jalapa* and *Amaranthus caudatus*: Expression, Processing, Localization and Biological Activity in Transgenic Tobacco," *Plant. Mol. Biol.*, 1996, pp. 993-1008, vol. 31.

Destéfano-Beltrán, L., "Using Genes Encoding Novel Peptides and Proteins to Enhance Disease Resistance in Plants," *Biotechnology in Plant Disease Control*, 1993, pp. 175-189.

Dushay, M., et al., "Twin *attacin* Antibacterial Genes of *Drosophila melanogaster*," *Gene*, 2000, pp. 49-57, vol. 246, Elsevier Science B. V.

Engstrom, A., et al., "Insect Immunity. The Primary Structure of the Antibacterial Protein attacin F and its Relation to Two Native Attacins from *Hyalophora cecropia*," *The EMBO Journal*, 1984, pp. 2065-2070, vol. 3(9).

Engstrom, P., et al., "The Antibacterial Effect of Attacins from the Silk Moth *Hyalophora cecropia* is Directed Against the Outer Membrane of *Escherichia coli*," *The EMBO Journal*, 1984, pp. 3347-3351, vol. 3(13).

Frobius, A., et al., "Isolation and Characterization of Novel Inducible Serine Protease Inhibitors from Larval Hemolymph of the Greater Wax Moth *Galleria mellonella*," *European Journal of Biochemistry*, 2000, pp. 2046-2053, vol. 267, FEBS.

Furukawa, S., et al., "A Novel Member of Lebocin Gene Family from the Silkworm, *Bombyx mori*," *Biochemical and Biophysical Research Communications*, 1997, pp. 769-774, vol. 238(3), Academic Press.

Gura, T., "Innate Immunity: Ancient System Gets New Respect," *Science*, Mar. 2001, pp. 2068-2071, vol. 291.

Hara, S., and M. Yamakawa, "A Novel Antibacterial Peptide Family Isolated from the Silkworm, *Bombyx mori*," *Biochem. J.*, 1995, pp. 651-656, vol. 310(2), The Biochemical Society, Great Britain.

Hegedus, D.D., et al., "The Impact of Biotechnology on Hyphomycetous Fungal Insect Biocontrol Agents," *Biotechnology Advances*, 1995, pp. 455-490, vol. 13(3); see particularly pp. 465-468.

Hetru, C., et al., "Antimicrobial Peptides from Insects" in: *Molecular Mechanisms of Immune Responses in Insects*, 1998, pp. 40-66, Brey et al., eds, Chapman & Hall, London.

Hightower, R., et al., "The Expression of Cecropin Peptide in Transgenic Tobacco Does Not Confer Resistance to *Pseudomonas syringae* pv tabaci," *Plant Cell Rep.*, 1994, pp. 295-299, vol. 13, No. 5.

Ko, K., "Using Antimicrobial Proteins to Enhance Plant Resistance," *APSnet Feature* (www.apsnet.org Online Publication), 2000, The American Phytopathological Society, USA.

Kockum, K., et al., "Insect Immunity. Isolation and Sequence of Two cDNA Closes Corresponding to Acidic and Basic Attacins fromn Hyalophora," *EMBO Journal*, 1984, pp. 2071-2075, vol. 3(9).

Lamberty, M., et al., "Insect Immunity: Isolation from the Lepidopteran *Heliothis virescens* of a Novel Insect Defensin with Potent Antifungal Activity," *The Journal of Biological Chemistry*, 1999, pp. 9320-9326, vol. 274(14), The American Society for Biochemistry and Molecular Biology, Inc., USA.

Loutelier, C., et al., "Non-Extractive Metabolism Study of E and A Destruxins in the Locust, *Locusta migratoria L.* III. Direct High-Performance Liquid Chromatographic Analysis and Parallel Fast Atom Bombardment Mass Spectrometric Monitoring," *Journal of Chromatography B: Biomedical Applications*, 1994, pp. 281-292, vol. 656(1).

Maes, M., et al., "Lower Serum Activity of Prolyl Endopeptidase in Fibromyalgia is Related to Severity of Depressive Symptoms and Pressure Hyperalgesia," *Psychological Medicine*, 1998, pp. 957-965, vol. 28(4), Cambridge University Press, United Kingdom.

Mitsuhara, I., et al., "Induced Expression of Sarcotoxin IA Enhanced Host Resistance Against Both Bacterial and Fungal Pathogens in Transgenic Tobacco," *Mol. Plant-Microbe Interact.*, 2000, pp. 860-868, vol. 13, No. 8.

Okamoto, M., et al., "Enhanced Expression of an Antimicrobial Peptide Sarcotoxin IA by GUS Fusion in Transgenic Tobacco Plants," *Plant Cell Physiol.*, 1998, pp. 57-63, vol. 39, No. 1.

Pang, S-Z., et al., "Expression of a Gene Encoding a Scorpion Insectotoxin Peptide in Yeast, Bacteria and Plants," *Gene*, 1992, pp. 165-172, vol. 116.

Ponti, D. et al., "An Amphibian Antimicrobial Peptide Variant Expressed in Nicotiana Tabacum Confers Resistance to Phytopathogens," *Biochem. J.*, 2003, pp. 121-127, vol. 370.

Rao, A.G., "Antimicrobial Peptides," *Molecular Plant-Microbe Interactions*, 1995, pp. 6-13, vol. 8(1), The American Phytopathological Society, USA.

Sasaki, T., "Amino-Acid Sequences of Two Basic Chymotrypsin Inhibitors from Silkworm Larval Hemolymph," *Biol. Chem. Hoppe-Seyler*, Nov. 1988, pp. 1235-1241, vol. 369.

Schaffrath, U., et al., "Constitutive Expression of the Defense-Related Rir1b Gene in Transgenic Rice Plants Confers Enhanced Resistance to the Rice Blast Fungus *Magnaporthe grisea*," *Plant Molecular Biology*, 2000, pp. 59-66, vol. 43, Kluwer Academic Publishers, Netherlands.

Sharma, A., et al., "Transgenic Expression of Cecropin B, an Antibacterial Peptide from *Bombyx mori*, Confers Enhanced Resistance to Bacterial Leaf Blight in Rice", *FEBS Letters*, 2000, pp. 7-11, vol. 484, Elsevier Science B.V.

Sun, S., et al., "Structure and Expression of the Attacin Genes in *Hyalophora cecropia*," *Eur. J. of Biochem.*, 1991, pp. 247-254, vol. 196(1), Springer International.

Thevissen, K., et al., "Fungal Membrane Responses Induced by Plant Defensins and Thionins," *The Journal of Biological Chemisty*, Jun. 1996, pp. 15018-15025, vol. 271(25), The American Society for Biochemistry and Molecular Biology, Inc., USA.

Toide, K., et al., "A Novel Prolyl Endopeptidase Inhibitor, JTP-4819 Its Behavorial and Neurochemical Properties for the Treatment of Alzheimer's Disease," *Reviews in the Neurosciences*, 1998, pp. 17-29, vol. 9(1), Freund & Pettman, U.K.

Tsuzurahara, S., et al., "Detection of MAGE-4 Protein in the Sera of Patients with Hepatitis-C Virus-Associated Hepatocellular Carcinoma and Liver Cirrhosis," *Jpn. J. Cancer Res.*, Sep. 1997, pp. 915-918, vol. 88(9).

Uttenweiler-Joseph, S., et al., "Differential Display of Peptides Induced During the Immune Response of *Drosophila*: A Matrix-Assisted Laser Desorption Ionization Time-of-Flight Mass Spectrometry Study," *Proc. Natl. Acad. Sci. USA*, Sep. 1998, pp. 11342-11347, vol. 95(19), The National Academy of Sciences.

GenBank Report for Accession No. U23831, Direct Submission on Mar. 31, 1995.

GenBank Report for Accession Report No. P01513, Direct Submission on Nov. 1, 1995.

GenBank Report for Accession No. AF226857, Direct Submission on Jan. 19, 2000.
GenBank Report for Accession No. A95923, Direct Submission on Jan. 26, 2000.
GenBank Report for Accession No. A95924, Direct Submission on Jan. 26, 2000.
GenBank Report for Accession No. A95927, Direct Submission on Jan. 26, 2000.
GenBank Report for Accession No. JC5666, Direct Submission on Jul. 21, 2000.
GenBank Report for Accession No. BI262536, Direct Submission on Jul. 17, 2001.
GenBank Report for Accession No. BI262626, Direct Submission on Jul. 17, 2001.
GenBank Report for Accession No. BI262643, Direct Submission on Jul. 17, 2001.
GenBank Report for Accession No. BI262658, Direct Submission on Jul. 17, 2001.
GenBank Report for Accession No. BI262708, Direct Submission on Jul. 17, 2001.
GenBank Report for Accession No. BI262711, Direct Submission on Jul. 17, 2001.
Hill, M.A. and J. Preiss, "Functional Analysis of Conserved Histidines in ADP-Glucose Pyrophosphorylast from *Escherichia coli*," *Biochem. Biophys. Res. Comm.*, 1998, pp. 573-577, vol. 244, No. 2.

Homology of Mag1 to known attacins

FIGURE 1

Mag1 homologs from M. sexta induced with pathogens

```
                           1                                                                         75
  iiglc.pk004.f3    (1)    --MSLSCLFLVALALVGAESRYIADDVVLVPMMVSRVRRDTHGSVTVNSDGTSGSVVKVPFAGDDKNVFSAIGGL
  iimlc.pk003.f3    (1)    ----------------------HEDDVVFVPMVVSRVRRDTHGSVTVNSDGTSGAIVKVPFAGDDKNIVSAIGGL imilc.pk002.m21     (1)    --MSLSCLLLFALALMGAESRYIADDVVFVPIVVSRVRRDTHGSVTVNSDGTSGAIVKVPFAGNDKNIVSAIGGL
           Mag1     (1)    ---------------------MFTKFVVLVCLLVGAKARPQLGALTFNSDGTSGAAVKVPFGGNKNNIFSAIGGA 76                                                                        150
  iiglc.pk004.f3   (74)    DLDKXLK--------------------------------------------------------------------
  iimlc.pk003.f3   (54)    DLDKNLKMSGATAGLAYDNVNGHGATLTNTHIPSFGDKLTAAGKLNVFHNDNHNLDVKALATRTMPDIPRVPDFN imilc.pk002.m21    (74)    DLDKNFKMSGATAGLAYDNVNRHGATLTNTHIPSFGDKLTATGKLNVFQNDKHNPGREGVGHQGPCQXFHAWPTS
           Mag1    (55)    DFNANHKLSSATAGVALDNIRGHGLSLTDTHIPGFGDKLTAAGKLNLFHNNNHDLTANAFATRNMPNIPQVPNFN 151                                                                       225
  iiglc.pk004.f3   (81)    ---------------------------------------------------------------------------
  iimlc.pk003.f3  (129)    TYGGGVDYMFKDKVGASASAAHTPLFDRNDYSVGGKLNLFR---------------------------------- imilc.pk002.m21   (149)    ---------------------------------------------------------------------------
           Mag1   (130)    TVGGGLDYMFKNKVGASLGAAHTDFINRNDYSVGGKLNLFRNPSTSLDFNAGFKKFDTPFMRSGWEPNMGFSLSK 226
  iiglc.pk004.f3   (81)    --
  iimlc.pk003.f3  (170)    -- imilc.pk002.m21   (149)    --
           Mag1   (205)    FF
```

FIGURE 2

Peptide sequences from Lys-C digested Mag1 maglysc18:
```
        1         5        10
        VGASLGAAHTDF
``` maglysc24:
```
        1         5        10        15
        NNIFSAIGGADFNANHK
``` maglysc29:
```
        1         5        10
        KFDTPFMRSGWE
``` maglysc36:
```
        1         5        10
        LNLFHNNNHDLT
```

FIGURE 3

MAG1 ANTIMICROBIAL POLYPEPTIDES AND THEIR USES

CROSS-REFERENCE TO RELATED APPLICATIONS

This application is a Divisional of U.S. application Ser. No. 10/125,258 filed Apr. 18, 2002, now U.S. Pat. No. 6,891,085, issued May 10, 2005, which claims priority to U.S. Provisional Application No. 60/285,355 filed Apr. 20, 2001.

FIELD OF THE INVENTION

The invention relates to plant disease resistance, particularly resistance to fungal pathogens. More specifically the present invention relates to the use of naturally occurring antimicrobial polypeptides isolated from insects induced with plant pathogens.

BACKGROUND OF THE INVENTION

Multicellular organisms produce a battery of antimicrobial peptides and proteins to defend themselves against microbial attack or injury. Many of these induced peptides and proteins possess broad antimicrobial activity against Gram-positive and/or Gram-negative bacteria (Boman, H. G. (1995) *Annu. Rev. Immunol.* 13:61–92). This defense system, called "innate immunity," may represent a chemical barrier that organisms deploy to stop dangerous microbes at their point of contact.

The peptides and proteins produced in response to microbial attack tend to work very differently from conventional antibiotics. Antibiotics work to block a crucial protein in an invading microbe. The mode of action of the antimicrobial defensive proteins varies. In some instances, they punch holes in a microbe's membranes and disrupt internal signaling of the microbe. In other instances, they may act to increase the host cell immune activity.

Several antimicrobial peptides have been isolated and their structures partially characterized. The defensins, one type of the antimicrobial peptides, are cysteine-rich peptides. Defensins have been isolated from insects and mammals. Insect defensins are 34–43 amino acid peptides with three disulfide bridges. They are produced by the insect fat body (Hoffmann et al. (1992) *Immunol. Today* 13:411–15). They have been shown to disrupt the permeability of the cytoplasmic membrane of *Micrococcus luteus*, resulting from the formation of voltage-dependent ion channels in the cytoplasmic membrane (Cociancich et al. (1993) *J. Biol. Chem.* 268:19239–19245).

Thionins are another group of small cysteine-rich antimicrobial peptides. Thionins are thought to play a role in the protection of plants against microbial infection. They are found in the seed endosperm, stems, roots, and in etiolated or pathogen stressed leaves of many plant species (Bohlmann et al. (1991) *Annu. Rev. Plant Physiol. Plant Mol. Biol.* 42:227–240). Thionins display toxicity to bacteria, fungi, yeasts, and even various mammalian cell types.

Disease in plants has many causes including fungi, viruses, bacteria, and nematodes. Phytopathogenic fungi have resulted in significant annual crop yield losses as well as devastating epidemics. Additionally, plant disease outbreaks have resulted in catastrophic crop failures that have triggered famines and caused major social change.

Molecular methods of crop protection not only have the potential to implement novel mechanisms for disease resistance, but can also be implemented more quickly than traditional breeding methods. Accordingly, molecular methods are needed to supplement traditional breeding methods to protect plants from pathogen attack.

Plant pathogenic fungi attack all of the approximately 300,000 species of flowering plants, but a single plant species can be host to only a few fungal species, and most fungi usually have a limited host range. It is for this reason that the best general strategy to date for controlling plant fungal disease has been to use resistant cultivars selected or developed by plant breeders. Unfortunately, even with the use of resistant cultivars, the potential for serious crop disease epidemics persists today, as evidenced by outbreaks of Victoria oat and southern corn leaf blight.

Accordingly, molecular methods utilizing the resistance mechanisms of naturally occurring plant insect pests to enhance plant disease resistance to microbes, particularly pathogenic fungi, are desirable.

SUMMARY OF THE INVENTION

Compositions and methods for increasing resistance to pathogens are provided. The compositions comprise antipathogenic peptides or defensive agents that are induced in insects by contacting the insect with a pathogen of interest. The compositions include polypeptides that possess antimicrobial properties, particularly fungicidal properties, and the nucleic acid molecules that encode such polypeptides. The methods and compositions of the present invention find use in impacting plant microbial pathogens and in enhancing plant disease resistance to microbial pathogens.

Expression cassettes comprising the nucleic acid molecules encoding the defensive agents, vector sequences and host cells for the expression of the polypeptides, and antibodies to the polypeptides are also provided. The compositions of the invention further provide plant cells, plants, and seed thereof, transformed with the nucleic acid molecules of the invention. The transgenic plants of the present invention are transformed with a nucleotide sequence of the invention and exhibit increased antimicrobial disease resistance, particularly fungal disease resistance that will lessen the need for artificial agricultural chemicals to protect field crops and increase crop yield.

The methods of the invention involve stably transforming a plant with at least one expression cassette comprising at least one nucleotide sequence of the invention operably linked with a promoter capable of driving expression of the nucleotide sequence in the plant or plant cell. It is recognized that a variety of promoters will be useful in the invention, the choice of which will depend in part upon the desired tissue localization and the level of expression of the disclosed nucleotide sequences and corresponding polypeptides. It is recognized that the levels of expression of the defensive agents in the plant cell can be controlled so as to achieve optimal disease resistance.

BRIEF DESCRIPTION OF THE DRAWINGS

FIG. 1. Amino acid sequence alignment of precursor Mag1 polypeptide (SEQ ID NO:2) with the class of immune proteins known as attacins. The precursor Mag1 polypeptide has 78% sequence similarity with attacin E/F precursor polypeptide (SEQ ID NO:19, Accession No: P01513). The remaining sequences are: Attacin A precursor polypeptide (SEQ ID NO:17, Accession No: P50725); Attacin B precursor polypeptide (SEQ ID NO:18, Accession No: P01512);

and the attacin precursor polypeptide known as Nuecin (SEQ ID NO:20, Accession No: Q26431).

FIG. 2. Amino acid sequence alignment of precursor Mag1 polypeptide (SEQ ID NO:2) with homologous polypeptide sequences of the invention encoded by cDNAs isolated from pathogen induced *Manduca sexta* libraries (SEQ ID NOS:4, 6, 8, and 10).

FIG. 3. The N-terminal amino acid sequences for the four Mag1 polypeptide Lys-C digestion fragments (SEQ ID NO:96, 97, 98, and 99).

DETAILED DESCRIPTION OF THE INVENTION

The present invention provides compositions and methods for enhancing plant disease resistance to plant pathogens, particularly fungal pathogens. The compositions of the invention include polypeptides and peptides that possess antimicrobial activity, particularly fungicidal activity. Such peptides or polypeptides are collectively referred to as "defensive agents" herein. Nucleic acid molecules encoding such defensive agents, as well as plants transformed with the nucleic acid molecules, are also included.

The invention is drawn to compositions and methods for inducing resistance in a plant to plant pests. The defensive agents comprise insect derived nucleotide and polypeptide sequences. Accordingly, the compositions and methods are also useful in protecting plants against fungal pathogens, viruses, nematodes, and the like.

Compositions for controlling plant pathogenic agents, particularly plant pathogenic microbial agents, more particularly plant pathogenic fungal agents are provided. Specific compositions provided include insect-derived antimicrobial polypeptides and the nucleic acid molecules encoding such polypeptides. Plants, plant cells, plant tissues and seeds thereof transformed with the nucleotide sequences of the invention are provided. Additionally, the compositions of the invention can be used in formulations for their disease resistance activities.

The present invention provides for isolated nucleic acid molecules comprising nucleotide sequences encoding the amino acid sequences shown in SEQ ID NOS:2, 4, 6, 8, 10, 12, 14, 16, 22, 23, 25, 26, 28, 29, 31, 32, 34, 35, 37, 38, 40, 41, 43, 44, 46, 47, 49, 50, 52, 53, 55, 56, 58, 59, 61, 62, 64, 65, 67, 68, 70, 71, 73, 74, 76, 77, 79, 80, 82, 83, 85, 86, 88, 89, 91, 92, 94, 95, 101, 103, 105, 107, 109, 111, 113, 115, 117, 119, 121, 123, 125, or 127. Further provided are polypeptides having an amino acid sequence encoded by a nucleic acid molecule described herein, for example, those set forth in SEQ ID NO:1, 3, 5, 7, 9, 11, 13, 15, 21, 24, 27, 30, 33, 36, 39, 42, 45, 48, 51, 54, 57, 60, 63, 66, 69, 72, 75, 78, 81, 84, 87, 90, 93, 100, 102, 104, 106, 108, 110, 112, 114, 116, 118, 120, 122, 124, or 126, and fragments and variants thereof.

Methods are provided for the expression of these sequences in a host plant to confer enhanced disease resistance of the host plant to plant pathogens, particularly plant fungal pathogens. The methods of the invention involve stably transforming a plant with at least one expression cassette comprising at least one nucleotide sequence of the invention operably linked with a promoter capable of driving expression of the nucleotide sequence in the plant cell. It is recognized that a variety of promoters will be useful in the invention, the choice of which will depend in part upon the desired level and desired tissue localization of expression of the disclosed nucleotide sequences. It is recognized that the levels and tissue location of expression can be controlled to modulate the levels of the antimicrobial polypeptides in the plant cell to optimize plant disease resistance to a particular pathogen.

By "plant pathogen" or "plant pest" is intended any microorganism that can cause harm to a plant, such as by inhibiting or slowing the growth of a plant, by damaging the tissues of a plant, by weakening the immune system of a plant or the resistance of a plant to abiotic stresses, and/or by causing the premature death of the plant, etc. Plant pathogens and plant pests include microbes such as fungi, viruses, bacteria, and nematodes.

By "disease resistance" or "pathogen resistance" is intended that the plants avoid the disease symptoms which are the outcome of plant pathogen interactions. That is, pathogens are prevented from causing plant diseases and the associated disease symptoms, or alternatively, the disease symptoms caused by the pathogen are minimized or lessened. The methods of the invention can be utilized to protect plants from disease, particularly those diseases that are caused by plant fungal pathogens.

An "antimicrobial agent," a "pesticidal agent," a "defensive agent," and/or a "fungicidal agent" will act similarly to suppress, control, and/or kill the invading pathogen.

A defensive agent will possess defensive activity. By "defensive activity" is intended an antipathogenic, antimicrobial, or antifungal activity.

By "antipathogenic compositions" is intended that the compositions of the invention have activity against pathogens including fungi, microorganisms, viruses, and nematodes and thus are capable of suppressing, controlling, and/or killing the invading pathogenic organism. An antipathogenic composition of the invention will reduce the disease symptoms resulting from microbial pathogen challenge by at least about 5% to about 50%, at least about 10% to about 60%, at least about 30% to about 70%, at least about 40% to about 80%, or at least about 50% to about 90% or greater. Hence, the methods of the invention can be utilized to protect organisms, particularly plants, from disease, particularly those diseases that are caused by invading pathogens.

Assays that measure antipathogenic activity are commonly known in the art, as are methods to quantify disease resistance in plants following pathogen infection. See, for example, U.S. Pat. No. 5,614,395, herein incorporated by reference. Such techniques include measuring over time the average lesion diameter, the pathogen biomass, and the overall percentage of decayed plant tissues. For example, a plant either expressing an antipathogenic polypeptide or having an antipathogenic composition applied to its surface shows a decrease in tissue necrosis (i.e., lesion diameter) or a decrease in plant death following pathogen challenge when compared to a control plant that was not exposed to the antipathogenic composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107–15111, herein incorporated by reference.

Furthermore, in vitro fungicidal assays include, for example, the addition of varying concentrations of the fungicidal composition to paper disks and placing the disks on agar containing a suspension of the pathogen of interest.

Following incubation, clear inhibition zones develop around the discs that contain an effective concentration of the fungicidal polypeptide (Liu et al. (1994) *Plant Biology* 91:1888–1892, herein incorporated by reference). Additional methods are used in the art to measure the in vitro fungicidal properties of a composition (Hu et al. (1997) *Plant Mol. Biol.* 34:949–959; Cammue et al. (1992) *J. Biol. Chem.* 267:2228–2233; and Thevissen et al. (1996) *J. Biol. Chem.* 271:15018–15025, all of which are herein incorporated by reference).

Pathogens of the invention include but are not limited to viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Specific fungal and viral pathogens for the major crops include: Soybeans: *Phytophthora megasperma* f.sp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*), *Corynespora cassicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata*, Soybean mosaic virus, *Glomerella glycines*, Tobacco Ring spot virus, Tobacco Streak virus, *Phakopsora pachyrhizi, Pythium aphanidermatum, Pythium ultimum, Pythium debaryanum*, Tomato spotted wilt virus, *Heterodera glycines Fusarium solani*; Canola: *Albugo candida, Alternaria brassicae, Leptosphaeria maculans, Rhizoctonia solani, Sclerotinia sclerotiorum, Mycosphaerella brassiccola, Pythium ultimum, Peronospora parasitica, Fusarium roseum, Alternaria alternata*; Alfalfa: *Clavibacter michiganensis* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium, Xanthomonas campestris* p.v. *alfalfae, Aphanomyces euteiches, Stemphylium herbarum, Stemphylium alfalfae*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana*, Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomanes, Pythium gramicola, Pythium aphanidermatum*, High Plains Virus, European wheat striate virus; Sunflower: *Plasmophora halstedii, Sclerotinia sclerotiorum, Aster Yellows, Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* p.v. *carotovora, Cephalosporium acremonium, Phytophthora cryptogea, Albugo tragopogonis*; Corn: *Fusarium moniliforme* var. *subglutinans, Erwinia stewartii, Fusarium verticilloides, Fusarium moniliforme, Gibberella zeae* (*Fusarium graminearum*), *Stenocarpella maydis* (*Diplodia maydis*), *Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride*, Maize Dwarf Mosaic Virus A & B, Wheat Streak Mosaic Virus, Maize Chlorotic Dwarf Virus, *Claviceps sorghi, Pseudomonas avenae, Erwinia chrysanthemi* pv. *zea, Erwinia carotovora*, Corn stunt spiroplasma, *Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium*, Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola* (*Glomerella graminicola*), *Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Periconia circinata, Fusarium moniliforme, Alternaria alternata, Bipolaris sorghicola, Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari, Sporisorium reilianum* (*Sphacelotheca reiliana*), *Sphacelotheca cruenta, Sporisorium sorghi*, Sugarcane mosaic H, Maize Dwarf Mosaic Virus A & B, *Claviceps sorghi, Rhizoctonia solani, Acremonium strictum, Sclerophthora macrospora, Peronosclerospora sorghi, Peronosclerospora philippinensis, Sclerospora graminicola, Fusarium graminearum, Fusarium oxysporum, Pythium arrhenomanes, Pythium graminicola*; Rice: *Magnaporthe grisea, Rhizoctonia solani*, etc.

The specific defensive agents of the invention have been demonstrated to have antipathogenic activity against particular pathogens. It is recognized that they may demonstrate activity against other pathogens, particularly other fungal pathogens. Some may even exhibit broad-spectrum antipathogenic activity. It is recognized that while antifungal polypeptides may demonstrate activity against a particular pest, such defensive agents may have activity against numerous fungal pathogens, as well as other plant pests. Thus, a plant transformed with a particular defensive agent of the invention may demonstrate broad-spectrum resistance.

In one embodiment of the invention, defensive agents are isolated from the hemolymph of insect larvae induced by injection of a plant pathogenic fungi. The antimicrobial polypeptides induced can be placed into at least four groups according to their amino acid sequence homology to known classes of proteins. These four groups consist of the attacin, lebocin, and serine protease inhibitor classes of proteins, and a group that does not demonstrate substantial homology to known proteins. The defensive agents enhance disease resistance to fungal pathogens, *Magnathorpa grisea* (*M. grisea*), *Rhizoctonia solani* (*R. solani*), and *Fusarium verticilloides* (*F. verticilloides*). Specifically, the polypeptides of the invention were identified from the hemolymph of insect larvae induced by injection of the plant pathogenic fungi, *M. grisea, R. solani,* or *F. verticilloides*.

The compositions of the invention comprise *M. sexta* (tobacco hornworm), *Heliothis virescens* (tobacco budworm), *Ostrinia nubilalis* (European cornborer), *Peregrinus maidis* (cornplant hopper), *Helicoverpa zea* (corn earworm), and *Agrotis ipsilon* (Black cutworm) nucleic acid and amino acid sequences. Particularly, the compositions of the invention comprise: an *M. sexta* full-length cDNA herein designated Mag1 (SEQ ID NO:1) and corresponding amino acid sequence (SEQ ID NO:2); an *M. sexta* full-length cDNA herein designated Rhizoc2 or iim1c.pk003.f3 (SEQ ID NO:3) and corresponding amino acid sequence (SEQ ID NO:4); an *M. sexta* partial cDNA herein designated iig1c.pk004.f3 (SEQ ID NO:5) and corresponding amino acid sequence (SEQ ID NO:6); an *M. sexta* partial cDNA herein designated imi1c.pk001.h7 (SEQ ID NO:7) and corresponding amino acid sequence (SEQ ID NO:8); an *M. sexta* partial cDNA herein designated imi1c.pk002.m21 (SEQ ID NO:9) and corresponding amino acid sequence (SEQ ID NO:10); an *M. sexta* full-length cDNA herein designated Rhizoc1 (SEQ ID NO:11) and corresponding amino acid sequence (SEQ ID NO:12); an *M. sexta* full-length cDNA herein designated Fus1 (SEQ ID NO:13) and corresponding amino acid sequence (SEQ ID NO:14); and an *M. sexta* full-length cDNA herein designated Rhizoc3 (SEQ ID NO:15) and corresponding amino acid sequence (SEQ ID NO:16).

The mature Mag1 polypeptide was isolated from the hemolymph of *M. sexta* larvae induced by injection of the plant pathogenic fungus *M. grisea*. The Mag1 precursor polypeptide consists of 206 amino acids. This polypeptide belongs to a broad class of insect immune proteins known as attacins that were originally isolated from *Hyalophora cecropia*. A Mag1 precursor polypeptide-encoding cDNA (SEQ ID NO:1) was subsequently isolated from a cDNA library derived from the fatbodies of pathogen induced *M. sexta*. The Mag1 precursor polypeptide shares 78% sequence similarity with attacin E/F precursor (SEQ ID NO:19, FIG. 1).

Attacin proteins are induced upon injection of insects (mostly lepidopteran species) with bacteria, and have been demonstrated to possess antibacterial properties (Kockum et al. (1984) *EMBO J.* 3:2071–2075; Engstrom et al. (1984) *EMBO J.* 3:2065–2070; Engstrom et al. (1984) *EMBO J.* 3:3347–3351; Bowman et al. (1985) *Dev. Comp. Immunol.* 9:551–558; Sun et al. (1991) *Eur. J. Biochem.* 196:247–254. The Mag1 polypeptide was induced by injection of an insect with a plant pathogenic fungus rather than by induction with a bacteria. Furthermore, the isolated Mag1 polypeptide demonstrates fungicidal activity at low concentrations against the plant pathogen *M. grisea* (see Example 1).

In addition, the polypeptides set forth in SEQ ID NOS:6, 8, and 10, and encoded by the cDNA clones, iig1c.pk004.f3, imi1c.pk001.h7, and imi1c.pk002.m21, respectively, are also attacin homologs. These polypeptides display about 48 to 62.3% sequence identity to the Mag1 polypeptide (SEQ ID NO:2) (see FIG. 2). These cDNA clones were isolated from *M. grisea* (iig1c.pk004.f3) and *B. bassiana* (imi1c.pk001.h7 and imi1c.pk002.m21) induced *M. sexta* derived cDNA libraries.

Similar to the Mag1 precursor polypeptide, the Rhizoc2 (SEQ ID NO:3) precursor polypeptide also shares sequence homology to the attacin class of proteins. The Rhizoc2 precursor polypeptide shares 75% sequence similarity and 68% sequence identity with the attacin E/F precursor protein shown in FIG. 1 (SEQ ID NO:19). The cDNA encoding the Rhizoc2 precursor polypeptide (SEQ ID NO:3) was isolated from a cDNA library derived from the fatbodies of *R. solani* induced *M. sexta*. The Rhizoc2 precursor polypeptide consists of 196 amino acids and the mature polypeptide demonstrates fungicidal activity at low concentrations against the plant pathogen *R. solani* (see Example 1). The partial cDNA imi1c.pk001.h7 identified from a *B. bassiana* induced *M. sexta* library is a fragment of the Rhizoc2 sequence.

Another polypeptide, designated Rhizoc1, with homology to the lebocin class of insect immune proteins, was similarly isolated from the hemolymph of *M. sexta* larvae induced by injection of the plant pathogenic fungus *R. solani*. A Rhizoc1 precursor polypeptide-encoding cDNA (SEQ ID NO:11) was subsequently isolated from a cDNA library derived from the fatbodies of *M. grisea* induced *M. sexta*. The Rhizoc1 precursor polypeptide consists of 142 amino acids and shares 65% sequence similarity and 61% sequence identity with lebocin 4 precursor protein (Accession No: JC5666).

The Rhizoc1 polypeptide demonstrates fungicidal activity at low concentrations against the plant pathogens *R. solani* and *F. verticilloides* (see Example 1). Unlike other members of the lebocin class of polypeptides, the Rhizoc1 polypeptide was induced upon injection of an insect with a plant fungal pathogen, rather than by induction with a bacteria. Indeed, other lebocin polypeptides have been demonstrated to possess antibacterial rather than fungicidal properties (Hara and Yamakawa (1995) *Biochem. J.* 310:651–656; Chowdhury, S. et al. (1995) *Biochem. Biophys. Res. Com.* 214:271–278; and Furukawa, S. et al. (1997) *Biochem. Biophys. Res. Com.* 238:769–774).

Additional Rhizoc1 homologs have been identified. The nucleotide sequences of the Rhizoc1 homologs are set forth in SEQ ID NOS:27, 33, 45, 48, 51, 72, 81, and 84. The amino acid sequences of the Rhizoc1 homologs are set forth in SEQ ID NOS:28, 29, 34, 35, 46, 47, 49, 50, 52, 53, 73, 74, 82, 83, 85, and 86.

A mature polypeptide designated Fus1 was isolated from the hemolymph of *M. sexta* larvae induced by injection of the plant pathogenic fungus *F. verticilloides*. This polypeptide demonstrates fungicidal activity at low concentrations against the plant pathogen *F. verticilloides* (see Example 1). A cDNA encoding the mature Fus1 polypeptide and part of the signal sequence (SEQ ID NO:13) was subsequently isolated from a cDNA library derived from the fatbodies of *M. grisea* induced *M. sexta*.

The Fus1 polypeptide of the invention is homologous to several proteins isolated from insect species that belong to the class of proteins known as the serine protease inhibitors (Frobius et al. (2000) *Eur. J. Biochem.* 267:2046–2053; Ramesh et al. (1988) *J. Biol. Chem.* 263:11523–1127; and Sasaki, T (1988) *Biol. Chem.* 369:1235–1241). The Fus1 polypeptide has about 47% sequence similarity to these proteins. The polypeptides identified by Frobius et al. were isolated from *Galleria mellonella* hemolymph after injection of larvae with a yeast polysaccharide preparation and demonstrate inhibition of serine proteases from the entomopathogenic fungus, *Metarhizium anisopliae*, an insect pathogen. A codon-biased Fus1 nucleotide sequence linked to the BAA signal sequence has been created. The codon-biased Fus1 nucleotide sequence was developed according to the codon bias of *M. sexta*. The codon-biased BAA-Fus1 nucleotide sequence is set forth in SEQ ID NO:120 and the also codon-biased Fus1 sequence is set forth in SEQ ID NO:122. The amino acid sequence of the BAA-Fus1 polypeptide is set forth in SEQ ID NO:121 and SEQ ID NO:123.

Additional Fus1 homologs have been identified. The nucleotide sequences of the Fus1 homologs are set forth in SEQ ID NOS:21, 36, and 78. The amino acid sequences of the Fus1 homologs are set forth in SEQ ID NOS:22, 23, 37, 38, 79, and 80.

A mature polypeptide designated, Rhizoc3, was isolated from the hemolymph of *M. sexta* larvae induced by injection of the plant pathogenic fungus *R. solani*. This polypeptide demonstrates fungicidal activity at low concentrations against the plant pathogen *R. solani* (see Example 1).

A Rhizoc3 precursor polypeptide encoding cDNA (SEQ ID NO:15) was subsequently isolated from a cDNA library derived from the fatbodies of *M. grisea* induced *M. sexta*. The Rhizoc3 precursor polypeptide consists of 61 amino acids and does not demonstrate sequence homology to any known proteins.

Homologs of Fus4 have been identified. The nucleotide sequences of the Fus4 homologs are set forth in SEQ ID NOS:24, 30, 39, 42, 54, 57, 60, 63, 66, 69, 75, 87, 90, and 93. The amino acid sequences of the Fus4 homologs are set forth in SEQ ID NOS:25, 26, 31, 32, 40, 41, 43, 44, 55, 56, 58, 59, 61, 62, 64, 65, 67, 68, 70, 71, 76, 77, 88, 89, 91, 92, 94, and 95.

Additional polypeptides active against *Fusarium* species have been identified from *Agrotis ipsilon*. The Fus6, Fus7, Fus8, Fus9, and Fus10 nucleotide sequences are set forth in SEQ ID NOS:100, 102, 104, 106, 108, 110, 112, 114, 116, and 118. The amino acid sequences of the Fus6, Fus7, Fus8, Fus9, and Fus10 polypeptides are set forth in SEQ ID NOS:101, 103, 105, 107, 109, 111, 113, 115, 117, and 119.

A codon-biased Fus2 nucleotide sequence linked to the BAA signal sequence has been created. The codon-biased BAA-Fus2 nucleotide sequence is set forth in SEQ ID NO:124 and the codon-biased Fus2 sequence is set forth in SEQ ID NO:126. The amino acid sequence of the BAA-Fus2 polypeptide is set forth in SEQ ID NO:125 and SEQ ID NO:127.

The polypeptides encoded by the nucleotide sequences of the invention may be processed into mature peptides as discussed elsewhere herein. The region from nucleotide 169 to nucleotide 298 of SEQ ID NO:11 encodes the mature Rhizoc1 peptide. The region from nucleotide 58 to nucleotide 624 of SEQ ID NO:3 encodes the mature Rhizoc2 peptide. The region from nucleotide 86 to nucleotide 208 of SEQ ID NO:15 encodes the mature Rhizoc3 peptide. The region from nucleotide 46 to nucleotide 216 of SEQ ID NO:13 encodes the mature Fus1 peptide. The nucleotide sequence set forth in SEQ ID NO:102 encodes the mature Fus6 peptide, the amino acid sequence of which, is set forth in SEQ ID NO:103. The nucleotide sequence set forth in SEQ ID NO:106 encodes the mature Fus7 peptide, the amino acid sequence of which, is set forth in SEQ ID NO:107. The nucleotide sequence set forth in SEQ ID NO:110 encodes the mature Fus8 peptide, the amino acid sequence of which, is set forth in SEQ ID NO:111. The nucleotide sequence set forth in SEQ ID NO:114 encodes the mature Fus9 peptide, the amino acid sequence of which, is set forth in SEQ ID NO:115. The nucleotide sequence set forth in SEQ ID NO:118 encodes the mature Fus10 peptide, the amino acid sequence of which, is set forth in SEQ ID NO:119.

Fragments and variants of the disclosed nucleotide sequences and polypeptides encoded thereby are also encompassed by the present invention. By "fragment" is intended a portion of the nucleotide sequence or a portion of the amino acid sequence. Fragments of a nucleotide sequence may encode polypeptide fragments that retain the biological activity of the native protein and hence possess antimicrobial and/or fungicidal activity. By "antimicrobial activity" or "fungicidal activity" is intended the ability to suppress, control, and/or kill the invading pathogenic microbe or fungus, respectively. A composition of the invention that possesses antimicrobial or fungicidal activity will reduce the disease symptoms resulting from microbial or fungal pathogen challenge by at least about 5% to about 50%, at least about 10% to about 60%, at least about 30% to about 70%, at least about 40% to about 80%, or at least about 50% to about 90% or greater. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

Alternatively, fragments of a nucleotide sequence of the invention may encode polypeptide fragments that are antigenic, thus, they are capable of eliciting an immune response. An "antigenic polypeptide" is herein defined as a polypeptide that is capable of generating an antibody. Antigenic polypeptide fragments of the disclosed amino acid sequences are also encompassed by the invention.

A nucleotide fragment of SEQ ID NO:1 that encodes a biologically active or antigenic portion of the amino acid sequence of SEQ ID NO:2 (Mag1), will encode at least 30, 35, 40, 45, 50, 55, 60, 70, 80, 90, 100, 150, or 200 contiguous amino acids, or up to the total number of amino acids (206) present in SEQ ID NO:2.

A nucleotide fragment of SEQ ID NO:3 that encodes a biologically active or antigenic portion of the amino acid sequence of SEQ ID NO:4 (Rhizoc2), will encode at least 15, 20, 25, 30, 35, 40, 45, 50, 55, 60, 70, 80, 90, 100, 110, 120, 130, 140, 150, 160, 170, 180, or 190 contiguous amino acids, or up to the total number of amino acids (196) present in SEQ ID NO:4.

A nucleotide fragment of SEQ ID NO:5 that encodes a biologically active or antigenic portion of the amino acid sequence of SEQ ID NO:6 (iig1c.pk004.f3), will encode at least 25, 30, 35, 40, 45, 50, 55, 60, or 70 contiguous amino acids, or up to the total number of amino acids (80) present in SEQ ID NO:6.

A nucleotide fragment of SEQ ID NO:7 that encodes a biologically active or antigenic portion of the amino acid sequence of SEQ ID NO:8 (imi1c.pk001.h7), will encode at least 25, 30, 35, 40, 45, 50, 55, 60, 70, 80, 90, 100, or 110 contiguous amino acids, or up to the total number of amino acids (111) present in SEQ ID NO:8.

A nucleotide fragment of SEQ ID NO:9 that encodes a biologically active or antigenic portion of the amino acid sequence of SEQ ID NO:10 (imi1c.pk002.m21), will encode at least 25, 30, 35, 40, 45, 50, 55, 60, 70, 80, 90, 100, 110, 120, 130, or 140 contiguous amino acids, or up to the total number of amino acids (148) present in SEQ ID NO:10.

A nucleotide fragment of SEQ ID NO:11 that encodes a biologically active or antigenic portion of the amino acid sequence of SEQ ID NO:12 (Rhizoc1), will encode at least 15, 20, 25, 35, 40, 45, 50, 55, 60, 70, 80, 90, 100, 110, 120, 130, or 140 contiguous amino acids, or up to the total number of amino acids (142) present in SEQ ID NO:12.

A nucleotide fragment of SEQ ID NO:13 that encodes a biologically active or antigenic portion of the amino acid sequence of SEQ ID NO:14 (Fus1), will encode at least 25, 30, 35, 40, 45, 50, 55, 60, 65, or 70 contiguous amino acids, or up to the total number of amino acids (71) present in SEQ ID NO:14.

A nucleotide fragment of SEQ ID NO:15 that encodes a biologically active or antigenic portion of the amino acid sequence of SEQ ID NO:16 (Rhizoc3), will encode at least 5, 10, 15, 20, 25, 30, 35, 40, 45, 50, 55, or 60 contiguous amino acids, or up to the total number of amino acids (61) present in SEQ ID NO:16.

A nucleotide fragment of SEQ ID NO:1, 3, 5, 7, 9, 11, 13, 15, 21, 24, 27, 30, 33, 36, 39, 42, 45, 48, 51, 54, 57, 60, 63, 66, 69, 72, 75, 78, 81, 84, 87, 90, 93, 100, 102, 104, 106, 108, 110, 112, 114, 116, 118, 120, 122, 124, or 126 that encodes a biologically active or antigenic portion of the amino acid sequence of SEQ ID NO:2, 4, 6, 8, 10, 12, 14, 16, 22, 23, 25, 26, 28, 29, 31, 32, 34, 35, 37, 38, 40, 41, 43, 44, 46, 47, 49, 50, 52, 53, 55, 56, 58, 59, 61, 62, 64, 65, 67, 68, 70, 71, 73, 74, 76, 77, 79, 80, 82, 83, 85, 86, 88, 89, 91, 92, 94, 95, 101, 103, 105, 107, 109, 111, 113, 115, 117, 119, 121, 123, 125, or 127, will encode at least 5, 10, 15, 20, 25, 30, 35, 40, 45, 50, or 55 contiguous amino acids, or up to the total number of amino acids present in SEQ ID NO:2, 4, 6, 8, 10, 12, 14, 16, 22, 23, 25, 26, 28, 29, 31, 32, 34, 35, 37, 38, 40, 41, 43, 44, 46, 47, 49, 50, 52, 53, 55, 56, 58, 59, 61, 62, 64, 65, 67, 68, 70, 71, 73, 74, 76, 77, 79, 80, 82, 83, 85, 86, 88, 89, 91, 92, 94, 95, 101, 103, 105, 107, 109, 111, 113, 115, 117, 119, 121, 123, 125, or 127.

A biologically active or antigenic portion of a polypeptide sequence set forth in SEQ ID NO:2, 4, 6, 8, 10, 12, 14, 16, 22, 23, 25, 26, 28, 29, 31, 32, 34, 35, 37, 38, 40, 41, 43, 44, 46, 47, 49, 50, 52, 53, 55, 56, 58, 59, 61, 62, 64, 65, 67, 68, 70, 71, 73, 74, 76, 77, 79, 80, 82, 83, 85, 86, 88, 89, 91, 92, 94, 95, 101, 103, 105, 107, 109, 111, 113, 115, 117, 119, 121, 123, 125, or 127 can be prepared by isolating a portion of one of the nucleotide sequences set forth in SEQ ID NO:1, 3, 5, 7, 9, 11, 13, 15, 21, 24, 27, 30, 33, 36, 39, 42, 45, 48, 51, 54, 57, 60, 63, 66, 69, 72, 75, 78, 81, 84, 87, 90, 93, 100, 102, 104, 106, 108, 110, 112, 114, 116, 118, 120, 122, 124, or 126, expressing the encoded portion of the polypeptide (e.g., by recombinant expression in vitro), and assessing the activity of the encoded portion of the polypeptide.

Alternatively, fragments of a nucleotide sequence that are useful as hybridization probes generally do not encode fragment polypeptides retaining biological activity. Thus, fragments of a nucleotide sequence may range from at least about 15 nucleotides, about 30 nucleotides, about 50 nucleotides, about 100 nucleotides, and up to the full-length nucleotide sequence encoding the polypeptides of the invention.

Fragments of the nucleotide sequence set forth in SEQ ID NO:1, from nucleotide 4 to 621, may range from at least 15, 20, 30, 40, 50, 60, 70, 80, 90, 100, 125, 150, 200, 300, 400, or 500 contiguous nucleotides, or up to the total number of nucleotides (618) present in SEQ ID NO:1 that encode SEQ ID NO:2 (Mag1).

Fragments of the nucleotide sequence set forth in SEQ ID NO:3, from nucleotide 34 to 624, may range from at least 15, 20, 30, 40, 50, 60, 70, 80, 90, 100, 125, 150, 200, 300, 400, or 500 contiguous nucleotides, or up to the total number of nucleotides (588) present in SEQ ID NO:3 that encode SEQ ID NO:4 (Rhizoc2).

Fragments of the nucleotide sequence set forth in SEQ ID NO:5 (iig1c.pk004.f3), from nucleotide 4 to 249, may range from at least 15, 20, 30, 40, 50, 60, 70, 80, 90, 100, 125, 150, or 200 contiguous nucleotides, or up to the total number of nucleotides (240) present in SEQ ID NO:5 that encode SEQ ID NO:6.

Fragments of the nucleotide sequence set forth in SEQ ID NO:7 (imi1c.pk001.h7), from nucleotide 4 to 336, may range from at least 15, 20, 30, 40, 50, 60, 70, 80, 90, 100, 125, 150, 200, 250, or 300 contiguous nucleotides, or up to the total number of nucleotides (333) present in SEQ ID NO:7 that encode SEQ ID NO:8. SEQ ID NO:7 is a fragment of the nucleotide sequence set forth in SEQ ID NO:3.

Fragments of the nucleotide sequence set forth in SEQ ID NO:9 (imi1c.pk002.m21), from nucleotide 4 to 447, may range from at least 15, 20, 30, 40, 50, 60, 70, 80, 90, 100, 125, 150, 200, 250, 300, 350, or 400 contiguous nucleotides, or up to the total number of nucleotides (444) present in SEQ ID NO:9 that encode SEQ ID NO:10.

Fragments of the nucleotide sequence set forth in SEQ ID NO:11 (Rhizoc1), from nucleotide 28 to 456, may range from at least 15, 20, 30, 40, 50, 60, 70, 80, 90, 100, 125, 150, 200, 250, 300, 350, or 400 contiguous nucleotides, or up to the total number of nucleotides (426) present in SEQ ID NO:11 that encode SEQ ID NO:12.

Fragments of the nucleotide sequence set forth in SEQ ID NO:13 (Fus1), from nucleotide 22 to 237, may range from at least 15, 20, 30, 40, 50, 60, 70, 80, 90, 100, 125, 150, 175, or 200 contiguous nucleotides, or up to the total number of nucleotides (216) present in SEQ ID NO:13 that encode SEQ ID NO:14.

Fragments of the nucleotide sequence set forth in SEQ ID NO:15 (Rhizoc3), from nucleotide 23 to 208, may range from at least 15, 20, 30, 40, 50, 60, 70, 80, 90, 100, 125, or 150 contiguous nucleotides, or up to the total number of nucleotides (183) present in SEQ ID NO:15 that encode SEQ ID NO:16.

Fragments of the nucleotide sequence set forth in SEQ ID NO:21, 24, 27, 30, 33, 36, 39, 42, 45, 48, 51, 54, 57, 60, 63, 66, 69, 72, 75, 78, 81, 84, 87, 90, or 93 may range from at least 15, 20, 30, 40, 50, 60, 70, 80, 90, 100, 125, or 150 contiguous nucleotides, or up to the total number of nucleotides present in SEQ ID NO:21, 24, 27, 30, 33, 36, 39, 42, 45, 48, 51, 54, 57, 60, 63, 66, 69, 72, 75, 78, 81, 84, 87, 90, or 93 that encode SEQ ID NO:22, 23, 25, 26, 28, 29, 31, 32, 34, 35, 37, 38, 40, 41, 43, 44, 46, 47, 49, 50, 52, 53, 55, 56, 58, 59, 61, 62, 64, 65, 67, 68, 70, 71, 73, 74, 76, 77, 79, 80, 82, 83, 85, 86, 88, 89, 91, 92, 94, or 95, respectively.

Fragments of the nucleotide sequence set forth in SEQ ID NO:100 (Fus6), from nucleotide 1 to 195, may range from at least 15, 20, 30, 40, 50, 60, 70, 80, 90, 100, 125, 150, 175, 180, 185, 190, or 195 contiguous nucleotides, or up to the total number of nucleotides (358) present in SEQ ID NO:100 that encode SEQ ID NO:101.

Fragments of the nucleotide sequence set forth in SEQ ID NO:104 (Fus7), from nucleotide 1 to 195, may range from at least 15, 20, 30, 40, 50, 60, 70, 80, 90, 100, 125, 150, 175, 180, 185, 190, or 195 contiguous nucleotides, or up to the total number of nucleotides (387) present in SEQ ID NO:104 that encode SEQ ID NO:105.

Fragments of the nucleotide sequence set forth in SEQ ID NO:108 (Fus8), from nucleotide 1 to 195, may range from at least 15, 20, 30, 40, 50, 60, 70, 80, 90, 100, 125, 150, 175, 180, 185, 190, or 195 contiguous nucleotides, or up to the total number of nucleotides (361) present in SEQ ID NO:108 that encode SEQ ID NO:109.

Fragments of the nucleotide sequence set forth in SEQ ID NO:112 (Fus9), from nucleotide 1 to 195, may range from at least 15, 20, 30, 40, 50, 60, 70, 80, 90, 100, 125, 150, 175, 180, 185, 190, 195, 200, 210, 220, 230, 240, 250, 260, 270, 280, 290, or 291 contiguous nucleotides, or up to the total number of nucleotides (466) present in SEQ ID NO:112 that encode SEQ ID NO:113.

Fragments of the nucleotide sequence set forth in SEQ ID NO:116 (Fus10), from nucleotide 1 to 195, may range from at least 15, 20, 30, 40, 50, 60, 70, 80, 90, 100, 125, 150, 175, 180, 185, 190, 195, 200, 210, or 220 contiguous nucleotides, or up to the total number of nucleotides (372) present in SEQ ID NO:116 that encode SEQ ID NO:117.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

By "variants" is intended substantially similar sequences. For nucleotide sequences, conservative variants include those sequences that, because of the degeneracy of the genetic code, encode the amino acid sequence of one of the polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but that still encode a polypeptide of the invention. Generally, variants of a particular nucleotide sequence of the invention will have at least 40%, 50%, 60%, 65%, 70%, 75%, 80%, 85%, 90%, 91%, 92%, 93%, 94%, 95%, 96%, 97%, 98%, 99%, or more sequence identity to that particular nucleotide sequence as determined by sequence alignment programs described elsewhere herein using default parameters.

By "variant" polypeptide is intended a polypeptide derived from the native polypeptide by deletion (so-called truncation) or addition of one or more amino acids to the N-terminal and/or C-terminal end of the native polypeptide; deletion or addition of one or more amino acids at one or more sites in the native polypeptide; or substitution of one or more amino acids at one or more sites in the native polypeptide. Variant polypeptides encompassed by the present invention are biologically active, that is, they continue to possess the desired biological activity of the native polypeptide, hence they will continue to possess antimicrobial and/or fungicidal activity. Such variants may result from, for example, genetic polymorphism or from human manipulation.

Biologically active variants of a native polypeptide of the invention will have at least 40%, 50%, 60%, 70%, 75%, 80%, 85%, 90%, 91%, 92%, 93%, 94%, 95%, 96%, 97%, 98%, 99% or more sequence identity to the amino acid sequence for the native polypeptide as determined by sequence alignment programs described elsewhere herein using default parameters. A biologically active variant of a polypeptide of the invention may differ from that polypeptide by as few as 1–15 amino acid residues, as few as 1–10, such as 6–10, as few as 5, as few as 4, 3, 2, or even 1 amino acid residue.

Biological activity of the polypeptides of the present invention can be assayed by any method known in the art (see for example, U.S. Pat. No. 5,614,395; Thomma et al. (1998) *Plant Biology* 95:15107–15111; Liu et al. (1994) *Plant Biology* 91:1888–1892; Hu et al. (1997) *Plant Mol. Biol.* 34:949–959; Cammue et al. (1992) *J. Biol. Chem.* 267: 2228–2233; and Thevissen et al. (1996) *J. Biol. Chem.* 271:15018–15025, all of which are herein incorporated by reference).

The polypeptides of the invention may be altered in various ways including amino acid substitutions, deletions, truncations, and insertions. Methods for such manipulations are generally known in the art. For example, amino acid sequence variants of the polypeptides of the invention can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the polypeptide of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the polypeptides of the invention encompass both naturally occurring polypeptides as well as variations and modified forms thereof. Such variants will continue to possess the desired antimicrobial, or in some cases, fungicidal activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the polypeptide sequences encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays for antimicrobial and/or fungicidal activity as referenced supra.

Variant nucleotide sequences and polypeptides also encompass sequences and polypeptides derived from a mutagenic and recombinogenic procedure such as DNA shuffling. With such a procedure, one or more different coding sequences in the nucleic acid molecules described in SEQ ID NO:1, 3, 5, 7, 9, 11, 13, 15, 21, 24, 27, 30, 33, 36, 39, 42, 45, 48, 51, 54, 57, 60, 63, 66, 69, 72, 75, 78, 81, 84, 87, 90, 93, 100, 102, 104, 106, 108, 110, 112, 114, 116, 118, 120, 122, 124, or 126 can be manipulated to create a new polypeptides possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the nucleic acid molecules of the invention and other known antimicrobial encoding nucleotide sequences to obtain a new nucleotide sequence coding for a polypeptide with an improved property of interest, such as increased antimicrobial and/or fungicidal properties at lower polypeptide concentrations or specificity for particular plant pathogens as well as, for example, specificity for a particular plant fungal pathogen including, but not limited to, pathogens such as *M. grisea* and *F. verticilloides*. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

The nucleotide sequences of the invention can be used to isolate corresponding sequences from other organisms, particularly other insects. In this manner, methods such as PCR, hybridization, and the like can be used to identify such sequences based on their sequence homology to the sequences set forth herein. Sequences isolated based on their sequence identity to the full-length nucleotide sequences set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded polypeptide sequences share substantial identity as defined elsewhere herein. Functions of orthologs are often highly conserved among species. Thus, isolated sequences that encode an antimicrobial protein and which hybridize under stringent conditions to the nucleotide sequences disclosed herein, or to fragments thereof, are encompassed by the present invention.

In a PCR approach, oligonucleotide primers can be designed for use in PCR reactions to amplify corresponding DNA sequences from cDNA or genomic DNA extracted from any insect of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the disease resistant sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire nucleotide sequence disclosed herein, or one or more portions thereof, may be used as a probe capable of specifically hybridizing to the corresponding nucleotide sequences and messenger RNAs. To achieve specific hybridization under a variety of conditions, such probes include sequences that are unique among the nucleotide sequences of the invention and are preferably at least about 10 nucleotides in length, and most preferably at least about 20 nucleotides in length. Such probes may be used to amplify corresponding sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Thus, isolated sequences that encode for an anti-microbial polypeptide and which hybridize under stringent conditions to a sequence disclosed herein, or to fragments thereof, are encompassed by the present invention.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m=81.5°$ C.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

The following terms are used to describe the sequence relationships between two or more nucleic acids or polynucleotides:(a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad. Sci.* 85:2444–2448; the algorithm of Karlin and Altschul (1990) *Proc. Natl. Acad. Sci. USA* 87:2264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0); the ALIGN PLUS program (version 3.0, copyright 1997); and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN and the ALIGN PLUS programs are based on the algorithm of Myers and Miller (1988) supra. A PAM120 weight residue table, a gap length penalty of 12, and a gap penalty of 4 can be used with the ALIGN program when comparing amino acid sequences.

The BLAST programs of Altschul et al (1990) *J. Mol. Biol.* 215:403 are based on the algorithm of Karlin and Altschul (1990) supra. The BLAST family of programs that can be used for database similarity searches includes: BLASTN for nucleotide query sequences against nucleotide database sequences; BLASTP for peptide query sequences against a peptide database; BLASTX for nucleotide query sequences against protein database sequences; TBLASTN for protein query sequences against nucleotide database sequences; and TBLASTX for nucleotide query sequences against nucleotide databases with the translation of all nucleotide sequences to protein. BLAST nucleotide searches can be performed with the BLASTN program, score=100, wordlength=12, to obtain nucleotide sequences homologous to a nucleotide sequence encoding a polypeptide of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.hlm.nih.gov. Alignment may also be performed manually by inspection.

Unless otherwise stated, sequence identity/similarity values provided herein refer to the value obtained using GAP Version 10 using the following parameters:% identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

GAP uses the algorithm of Needleman and Wunsch (1970) *J. Mol. Biol.* 48:443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

For purposes of the present invention, comparison of nucleotide or polypeptide sequences for determination of percent sequence identity to the nucleotide or polypeptide sequences disclosed herein is preferably made using the ClustalW program (Version 1.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 80%, 90%, 95%, or more sequence identity compared to a reference sequence using one of the alignment programs described using standard parameters. One of skill in the art will recognize that these values can be appropriately adjusted to determine corresponding identity of polypeptides encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, or 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 80%, 85%, 90%, or 95% sequence identity to the reference sequence over a specified comparison window. Preferably, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The nucleic acid sequences of the present invention can be expressed in a host cell such as bacteria, fungi, yeast, insect, mammalian, or plant cells. It is expected that those of skill in the art are knowledgeable in the numerous expression systems available for expression of a nucleic acid encoding a polypeptide of the present invention. No attempt to describe in detail the various methods known for the expression of polypeptides in prokaryotes or eukaryotes will be made.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species, or, if from the same species, is substantially modified from its original form by deliberate human intervention.

By "host cell" is meant a cell, which comprises a heterologous nucleic acid sequence of the invention. Host cells may be prokaryotic cells such as *E. coli*, or eukaryotic cells such as yeast, insect, amphibian, or mammalian cells. Preferably, host cells are monocotyledonous or dicotyledonous plant cells, particularly rice and maize plant cells.

The disease resistance-conferring sequences of the invention are provided in expression cassettes or DNA constructs for expression in the plant of interest. The cassette will include 5' and 3' regulatory sequences operably linked to a nucleotide sequence of the invention. By "operably linked" is intended a functional linkage between a promoter and a second sequence, wherein the promoter sequence initiates and mediates transcription of the nucleotide sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the disease resistant sequence to be under the transcriptional regulation of the regulatory regions. The expression cassette may additionally contain selectable marker genes.

The expression cassette will include in the 5'-3' direction of transcription, a transcriptional and translational initiation region, a signal peptide sequence, a disease resistant DNA sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

While it may be preferable to express the sequences using heterologous promoters, the native promoter sequences may be used. Such constructs would vary expression levels of the disease resistant RNA/protein in the plant or plant cell. Thus, the phenotype of the plant or plant cell is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; and Joshi et al. (1987) *Nucleic Acid Res.* 15:9627–9639.

Where appropriate, the nucleotide sequences may be optimized for increased expression in the transformed host. That is, the nucleotide sequences can be synthesized using plant-preferred codons for improved expression in plants. Methods are available in the art for synthesizing plant-preferred nucleotide sequences or genes. See, for example, U.S. Pat. Nos. 5,380,831, and 5,436,391, and Murray et al. (1989) *Nucleic Acids Res.* 17:477–498, herein incorporated by reference. Nucleotide sequences have been created that encode Fus1 and Fus2 operably linked to BAA and codon biased for expression in host cells. The BAA-Fus1 nucleotide sequence was codon-biased according to *M. sexta* codon usage. The BAA-Fus2 nucleotide sequence was codon-biased according to *Streptomyces coelicolor* codon usage. *S. coelicolor* codon usage patterns resemble the codon usage patterns of many plants. The development of the codon-biased sequences is described elsewhere herein.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In certain embodiments of the invention, it is desirable to utilize the mature peptide or the nucleotide sequence encoding the mature peptide. Within the cell, proteolytic modifications of amino acid sequences occur frequently. The proteolytic event removes amino acids from the precursor polypeptide to yield a mature peptide. The proteolytic processing can be highly sequence specific. Often the precursor peptides are inactive while the mature peptides possess the desired activity. Thus, isolation of a peptide based on its activity results in isolation of the active, mature peptide. Discovery of the existence of pre-sequences occurs when the nucleotide sequence encoding the mature peptide is identified. The open reading frame that encodes the mature peptide also encodes the presequences that were removed by the cell. Proteolytic maturation of amino acid sequences occurs in multiple cellular locations including, but not limited to, the endoplasmic reticulum, the cytoplasm, the mitochondria, the chloroplasts, the nucleus, the Golgi Apparatus, and the extracellular matrix. Proteolytic processing of peptides is discussed in Creighton, T. E. (1993) *Proteins: Structures & Molecular Properties*. W.H. Freeman & Co., U.S.A and Alberts et al eds. (1994) *Molecular Biology of the Cell*. Garland Publishing, Inc., New York, herein incorporated by reference. Rather than rely on a host cell to properly process the polypeptide of the invention, employment of a nucleotide sequence encoding the mature peptide may be desirable.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126–6130); potyvirus leaders, for example, TEV leader (Tobacco Etch Virus) (Allison et al. (1986); MDMV leader (Maize Dwarf Mosaic Virus); *Virology* 154:9–20), and human immunoglobulin heavy-chain binding protein (BiP), (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, New York), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

Signal peptides may be fused to the disease resistant nucleotide sequence of the invention to direct transport of the expressed gene product out of the cell to the desired site of action in the intercellular space. Examples of signal peptides include those natively linked to the Barley alpha amylase protein (BAA), sporamin, oryzacystatin-I, and those from the plant pathogenesis-related proteins, e.g., PR-1, PR-2, etc.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D), and sulfonylureas (SUs). See generally, Yarranton (1992) *Curr. Opin. Biotech.* 3:506–511; Christopherson et al. (1992) *Proc. Natl. Acad. Sci. USA* 89:6314–6318; Yao et al. (1992) *Cell* 71:63–72; Reznikoff (1992) *Mol. Microbiol.* 6:2419–2422; Barkley et al. (1980) in *The Operon*, pp. 177–220; Hu et al. (1987) *Cell* 48:555–566; Brown et al. (1987) *Cell* 49:603–612; Figge et al. (1988) *Cell* 52:713–722; Deuschle et al. (1989) *Proc. Natl. Acad. Sci. USA* 86:5400–5404; Fuerst et al. (1989) *Proc. Natl. Acad. Sci. USA* 86:2549–2553; Deuschle et al. (1990) *Science* 248:480–483; Gossen (1993) Ph.D. Thesis, University of Heidelberg; Reines et al. (1993) *Proc. Natl. Acad. Sci. USA* 90:1917–1921; Labow et al. (1990) *Mol. Cell. Biol.* 10:3343–3356; Zambretti et al. (1992) *Proc. Natl. Acad. Sci. USA* 89:3952–3956; Baim et al. (1991) *Proc. Natl. Acad. Sci. USA* 88:5072–5076; Wyborski et al. (1991) *Nucleic Acids Res.* 19:4647–4653; Hillenand-Wissman (1989) *Topics Mol. Struc. Biol.* 10:143–162; Degenkolb et al. (1991) *Antimicrob. Agents Chemother.* 35:1591–1595; Kleinschnidt et al. (1988) *Biochemistry* 27:1094–1104; Bonin (1993) Ph.D. Thesis, University of Heidelberg; Gossen et al. (1992) *Proc. Natl. Acad. Sci. USA* 89:5547–5551; Oliva et al. (1992) *Antimicrob. Agents Chemother.* 36:913–919; Hlavka et al. (1985) *Handbook of Experimental Pharmacology*, Vol. 78 (Springer-Verlag, Berlin); Gill et al. (1988) *Nature* 334:721–724. Such disclosures are herein incorporated by reference.

The above list of selectable marker genes is not meant to be limiting. Any selectable marker gene can be used in the present invention.

A number of promoters can be used in the practice of the invention. The promoters can be selected based on the desired outcome. That is, the nucleic acids can be combined with constitutive, tissue-preferred, inducible or other promoters for expression in plants. Such constitutive promoters include, for example, the core promoter of the Rsyn7 promoter and other constitutive promoters disclosed in WO 99/43838 and U.S. Pat. No. 6,072,050; Scp1 promoter (U.S. Pat. No. 6,072,050), rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. Pat. No. 5,659,026), Maize h2B (PCT Application Serial No. WO 99/43797) and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992) *Plant Cell* 4:645–656; and Van Loon (1985) *Plant Mol. Virol.* 4:111–116. See also WO 99/43819, herein incorporated by reference.

Of interest are promoters that are expressed locally at or near the site of pathogen infection. See, for example, Marineau et al. (1987) *Plant Mol. Biol.* 9:335–342; Matton et al. (1989) *Molecular Plant-Microbe Interactions* 2:325–331; Somsisch et al. (1986) *Proc. Natl. Acad. Sci. USA* 83:2427–2430; Somsisch et al. (1988) *Mol. Gen. Genet.* 2:93–98; and Yang (1996) *Proc. Natl. Acad. Sci. USA*

93:14972–14977. See also, Chen et al. (1996) *Plant J.* 10:955–966; Zhang et al. (1994) *Proc. Natl. Acad. Sci. USA* 91:2507–2511; Warner et al. (1993) *Plant J.* 3:191–201; Siebertz et al. (1989) *Plant Cell* 1:961–968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189–200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425–449; Duan et al. (1996) *Nature Biotechnology* 14:494–498); wun1 and wun2, U.S. Pat. No. 5,428,148; win1 and win2 (Stanford et al. (1989) *Mol. Gen. Genet.* 215:200–208); systemin (McGurl et al. (1992) *Science* 225:1570–1573); WIP1 (Rohmeier et al. (1993) *Plant Mol. Biol.* 22:783–792; Eckelkamp et al. (1993) *FEBS Letters* 323:73–76); MPI gene (Corderok et al. (1994) *Plant J.* 6(2):141–150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421–10425 and McNellis et al. (1998) *Plant J.* 14(2):247–257) and tetracycline-inducible and tetracycline-repressible promoters (see, for example, Gatz et al. (1991) *Mol. Gen. Genet.* 227:229–237, and U.S. Pat. Nos. 5,814,618 and 5,789,156), herein incorporated by reference.

Tissue-preferred promoters can be utilized to target enhanced antimicrobial polypeptide expression within a particular plant tissue. See, for example, Yamamoto et al. (1997) *Plant J.* 12(2):255–265; Kawamata et al. (1997) *Plant Cell Physiol.* 38(7):792–803; Hansen et al. (1997) *Mol. Gen Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell Differ.* 20:181–196; Orozco et al. (1993) *Plant Mol. Biol.* 23(6):1129–1138; Matsuoka et al. (1993) *Proc. Natl. Acad. Sci. USA* 90(20):9586–9590; and Guevara-Garcia et al. (1993) *Plant J.* 4(3):495–505. Such promoters can be modified, if necessary, for weak expression.

The method of transformation/transfection is not critical to the instant invention; various methods of transformation or transfection are currently available. Thus, any method, which provides for effective transformation/transfection may be employed. Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717–2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923–926); and Lec1 transformation (WO 00/28058). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature (London)* 311:763–764; Bowen et al., U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, New York), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell Reports* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

The present invention may be used for transformation of any plant species, including, but not limited to, monocots and dicots. Examples of plants of interest include, but are not limited to, rice (*Oryza sativa*), corn (*Zea mays*), *Brassica* sp. (e.g., *B. napus, B. rapa, B. juncea*), particularly those *Brassica* species useful as sources of seed oil, alfalfa (*Medi*- cago sativa), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and muskmelon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, rice, corn, alfalfa, sunflower, *Brassica*, soybean, cotton, safflower, peanut, sorghum, wheat, millet, tobacco, etc.).

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang et al. (1977) *Nature* 198:1056), the tryptophan (trp) promoter system (Goeddel et al. (1980) *Nucleic Acids Res.* 8:4057) and the lambda derived P L promoter and N-gene ribosome binding site (Shimatake et al. (1981) *Nature* 292:128). The inclusion of selection markers in DNA vectors transfected in *E. coli*. is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a polypeptide of the present invention are available using *Bacillus* sp. and *Salmonella* (Palva et al. (1983) *Gene* 22:229–235); Mosbach et al. (1983) *Nature* 302:543–545).

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the polypeptides of the instant invention.

The sequences of the present invention can also be ligated to various expression vectors for use in transfecting cell cultures of, for instance, mammalian, insect, or plant origin. Illustrative cell cultures useful for the production of the peptides are mammalian cells. A number of suitable host cell lines capable of expressing intact proteins have been developed in the art, and include the HEK293, BHK21, and CHO cell lines. Expression vectors for these cells can include expression control sequences, such as an origin of replication, a promoter (e.g. the CMV promoter, a HSV tk promoter or pgk (phosphoglycerate kinase) promoter), an enhancer (Queen et al. (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of polypeptides of the present invention are available, for instance, from the American Type Culture Collection.

Appropriate vectors for expressing polypeptides of the present invention in insect cells are usually derived from the SF9 baculovirus. Suitable insect cell lines include mosquito larvae, silkworm, armyworm, moth and *Drosophila* cell lines such as a Schneider cell line (See, Schneider (1987) *J. Embryol. Exp. Morphol.* 27:353–365).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague et al. (1983) *J. Virol.* 45:773–781). Additionally, gene sequences to control replication in the host cell may be incorporated into the vector such as those found in bovine papilloma virus type-vectors (Saveria-Campo (1985) *DNA Cloning Vol. II a Practical Approach*, D. M. Glover, Ed., IRL Press, Arlington, Va., pp. 213–238).

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art (Kuchler (1997) *Biochemical Methods in Cell Culture and Virology*, Dowden, Hutchinson and Ross, Inc.).

Synthesis of heterologous nucleotide sequences in yeast is well known (Sherman et al. (1982) *Methods in Yeast Genetics*, Cold Spring Harbor Laboratory). Two widely utilized yeasts for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A polypeptide of the present invention, once expressed, can be isolated from yeast by lysing the cells and applying standard protein isolation techniques to the lysates. The monitoring of the purification process can be accomplished by using Western blot techniques, UV absorption spectra, radioimmunoassay, or other standard immunoassay techniques.

The invention is drawn to a general method for identifying and making antimicrobial compositions, particularly antifungal compositions. The methods involve injection of an insect with a suspension of a plant pathogenic fungus to induce insect polypeptides possessing antimicrobial activity. Such polypeptides are isolated from the insect hemolymph using a combination of high-resolution liquid chromatography and mass spectrophotometry.

The general strategy for the discovery of these insect-derived antimicrobial peptides involves challenging insects with a selected plant pathogen and collecting hemolymph and fat body samples at various times post-induction. For example, hemolymph and fat body samples can be collected at about 8 hour, 16 hour, 24 hour, or 48 hour intervals. It is recognized that any method for protein separation and identification may be used to isolate peptides and the corresponding nucleic acid sequences.

While not bound by any particular method, identification of antimicrobial peptides active against the target pathogen may be achieved using an integrated proteomic, genomic, and miniaturized bioassay approach. This approach consists of separation of hemolymph isolated from induced insects. Any method of separation can be used including HPLC separation. Fractions from HPLC-aided separation may be separated into 30-second fractions in a microtiter plate format, i.e., 96 well microtiter plate. Fractions collected in this manner are dried down and directly used in a fungal growth assay (FGA) in which the dried fractions are resuspended in 100 µl of half strength potato dextrose broth containing a suspension of the target fungal pathogen. Fractions that contain antimicrobial peptides are identified in the FGA by their ability to inhibit fungal growth after several hours, generally 24 to 48 hours. These fractions are subjected to further purification in order to isolate individual peptides and the specific peptide responsible for the observed activity is determined by FGA. This peptide is subsequently N-terminally sequenced and its molecular weight determined by mass spectrometry to provide information to identify the corresponding gene from sequence data derived from the corresponding insect cDNA libraries. The complete amino acid sequence of the peptide is determined by translation of the nucleic acid sequence and the mature peptide identified based on both N-terminal sequence and molecular weight information.

The defensive agents of the invention encompasses the mature active peptides as well as unprocessed or preproforms of the peptides. Where a mature peptide has been isolated, the prepro sequence, or signal sequence, can be obtained by a number of general molecular biology techniques known in the art.

As indicated, the defensive agents may be isolated from any insect of interest. Of particular interest are insects living in harsh environments and insects that are natural plant predators. While any insect may be utilized, it may be beneficial to use insect predators of a particular plant of interest. For example, to obtain defensive agents for use in maize, while any insect may be used, maize insect predators may be beneficial.

Although a defensive agent may be induced by a particular pathogen, it is anticipated that the defensive agent may be effective against one or more additional pathogens, including but not limited to, any of the pathogens listed above.

The polypeptides are tested for antimicrobial activity using in vitro assays as described elsewhere herein. Isolated antimicrobial polypeptides are subjected to proteolysis, and the amino termini of the resulting proteolytic fragments are sequenced. Degenerate oligonucleotides encoding the amino terminal sequence tags are used to identify the antimicrobial polypeptide-encoding cDNA's from corresponding pathogen induced insect cDNA libraries. The nucleic acid molecules encoding the antimicrobial polypeptides are used for the transformation of plant cells to generate plants with enhanced disease resistance. Additionally, the compositions of the invention can be used to generate formulations possessing disease resistance activities.

Methods for increasing pathogen resistance in a plant are provided. The methods involve stably transforming a plant with a DNA construct comprising a nucleotide sequence of a defensive agent of the invention operably linked to promoter that drives expression in a plant. Such methods may find use in agriculture particularly in limiting the impact of plant fungal pathogens on crop plants. The antimicrobial nucleotide sequences comprise the insect nucleic acid molecules of the invention and functional variants and fragments thereof. The choice of promoter will depend on the desired timing and location of expression of the antimicrobial nucleotide sequences. Promoters of the invention include constitutive, inducible, and tissue-preferred promoters.

As discussed above, the nucleotide sequences of the invention encode polypeptides with antimicrobial properties, particularly fungicidal properties. Hence, the sequences of the invention may enhance transgenic plant disease resistance by disrupting cellular function of plant pathogens, particularly plant fungal pathogens. However, it is recognized that the present invention is not dependent upon a particular mechanism of defense. Rather, the compositions and methods of the invention work to increase resistance of the plant to pathogens independent of how that resistance is increased or achieved.

The methods of the invention can be used with other methods available in the art for enhancing disease resistance in plants. Similarly, the antimicrobial compositions described herein may be used alone or in combination with other nucleotide sequences, polypeptides, or agents to protect against plant diseases and pathogens. Although any one of a variety of second nucleotide sequences may be utilized, specific embodiments of the invention encompass those second nucleotide sequences that, when expressed in a plant, help to increase the resistance of a plant to pathogens.

Proteins, peptides, and lysozymes that naturally occur in insects (Jaynes et al. (1987) *Bioassays* 6:263–270), plants (Broekaert et al. (1997) *Critical Reviews in Plant Sciences* 16:297–323), animals (Vunnam et al. (1997) *J. Peptide Res.* 49:59–66), and humans (Mitra and Zang (1994) *Plant Physiol.* 106:977–981; Nakajima et al. (1997) *Plant Cell Reports* 16:674–679) are also a potential source of plant disease resistance. Examples of such plant resistance-conferring sequences include those encoding sunflower rhoGTPase-Activating Protein (rhoGAP), lipoxygenase (LOX), Alcohol Dehydrogenase (ADH), and *Sclerotinia*-Inducible Protein-1 (SCIP-1) described in U.S. application Ser. No. 09/714,767, herein incorporated by reference. These nucleotide sequences enhance plant disease resistance through the modulation of development, developmental pathways, and the plant pathogen defense system. Other plant defense proteins include those described in WO 99/43823 and WO 99/43821, all of which are herein incorporated by reference. It is recognized that such second nucleotide sequences may be used in either the sense or antisense orientation depending on the desired outcome.

In one embodiment of the invention, at least one expression cassette comprising a nucleic acid molecule encoding the Mag1 polypeptide set forth in SEQ ID NO:2 is stably incorporated into a rice plant host, to confer on the plant enhanced disease resistance to fungal pathogens, particularly the pathogen *M. grisea*. While the choice of promoter will depend on the desired timing and location of expression of the Mag1 nucleotide sequence, preferred promoters include constitutive and pathogen-inducible promoters. By "inducible" is intended the ability of the promoter sequence to regulate expression of an operably linked nucleotide sequence in response to a stimulus. In the case of a pathogen-inducible promoter, regulation of expression will be in response to a pathogen-derived stimulus.

Another embodiment of the invention involves the stable incorporation of at least one expression cassette comprising a nucleotide sequence encoding at least one of the Rhizoc1 polypeptide set forth in SEQ ID NO:12, the Rhizoc2 polypeptide set forth in SEQ ID NO:4, or the Rhizoc3 polypeptide set forth in SEQ ID NO:16 into a rice plant host to confer on the plant enhanced disease resistance to fungal pathogens, particularly the pathogen *R. solani*. While the choice of promoter will depend on the desired timing and location of expression of the Mag1 nucleotide sequence, preferred promoters include constitutive and pathogen-inducible promoters.

An additional embodiment of the invention involves the stable incorporation of at least one expression cassette comprising a nucleotide sequence encoding at least one of the Rhizoc1 polypeptide set forth in SEQ ID NO:12 or the Fus1 polypeptide set forth in SEQ ID NO:14 into a corn plant host to confer on the plant enhanced disease resistance to fungal pathogens, particularly the pathogen *F. verticilloides*. In an embodiment the nucleotide sequence is a codon-biased sequence, such as the codon-biased sequence set forth in SEQ ID NO:122, 124, 126, or 128. While the choice of promoter will depend on the desired timing and location of expression of the Mag1 nucleotide sequence, preferred promoters include constitutive and pathogen-inducible promoters.

In an embodiment of the invention, the polypeptides of the invention can be formulated with an acceptable carrier into an antimicrobial composition(s) that is for example, a suspension, a solution, an emulsion, a dusting powder, a dispersible granule, a wettable powder, and an emulsifiable concentrate, an aerosol, an impregnated granule, an adjuvant, or a coatable paste, and also in encapsulations, for example, polymer substances.

In another embodiment, the defensive agents comprise isolated polypeptides of the invention. The defensive agents of the invention find use in the decontamination of plant pathogens during the processing of grain for animal or human food consumption; during the processing of feedstuffs, and during the processing of plant material for silage. In this embodiment, the defensive agents of the invention are presented to grain, plant material for silage, or a contaminated food crop, or during an appropriate stage of the processing procedure, in amounts effective for anti-microbial activity. The compositions can be applied to the environment of a plant pathogen by, for example, spraying, atomizing, dusting, scattering, coating or pouring, introducing into or on the soil, introducing into irrigation water, by seed treatment, or dusting at the time when the plant pathogen has begun to appear or before the appearance of pests as a protective measure. It is recognized that any means to bring the defensive agent polypeptides in contact with the plant pathogen can be used in the practice of the invention.

Methods are provided for controlling plant pathogens comprising applying a decontaminating amount of a polypeptide or composition of the invention to the environment of the plant pathogen. The polypeptides of the invention can be formulated with an acceptable carrier into a composition(s) that is, for example, a suspension, a solution, an emulsion, a dusting powder, a dispersible granule, a wettable powder, an emulsifiable concentrate, an aerosol, an impregnated granule, an adjuvant, a coatable paste, and also encapsulations in, for example, polymer substances.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors or other preparations that influence plant growth. One or more agrochemicals including, but not limited to, herbicides, insecticides, fungicides, bacteriocides, nematocides, molluscicides, acaracides, plant growth regulators, harvest aids, and fertilizers, can be combined with carriers, surfactants, or adjuvants customarily employed in the art of formulation or other components to facilitate product handling and application for particular target mycotoxins. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention are normally applied in the form of compositions and can be applied to the crop area or plant to be treated, simultaneously or in succession, with other compounds. In some embodiments, methods of applying an active ingredient of the present invention or an agrochemical composition of the present invention (which contains at least one of the proteins of the present invention) are foliar application, seed coating, and soil application.

Suitable surface-active agents include, but are not limited to, anionic compounds such as a carboxylate of, for example, a metal; a carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate, or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g. polyoxyethylene sorbitan fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate, or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include, but are not limited to, inorganic minerals such as kaolin, phyllosilicates, carbonates, sulfates, phosphates, or botanical materials such as cork, powdered corncobs, peanut hulls, rice hulls, and walnut shells.

The compositions of the present invention can be in a suitable form for direct application or as concentrate of primary composition, which requires dilution with a suitable quantity of water or other diluent before application. The decontaminating concentration will vary depending upon the nature of the particular formulation, specifically, whether it is a concentrate or to be used directly.

In a further embodiment, the compositions, as well as the polypeptides of the present invention can be treated prior to formulation to prolong the activity when applied to the environment of a plant pathogen as long as the pretreatment is not deleterious to the activity. Such treatment can be by chemical and/or physical means as long as the treatment does not deleteriously affect the properties of the composition(s). Examples of chemical reagents include, but are not limited to, halogenating agents; aldehydes such as formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) *Animal Tissue Techniques* (W.H. Freeman and Co.).

In an embodiment of the invention, the compositions of the invention comprise a microbe having stably integrated the nucleotide sequence of a defensive agent. The resulting microbes can be processed and used as a microbial spray. Any suitable microorganism can be used for this purpose. See, for example, Gaertner et al. (1993) in *Advanced Engineered Pesticides*, Kim (Ed.). In one embodiment, the nucleotide sequences of the invention are introduced into microorganisms that multiply on plants (epiphytes) to deliver the defensive agents to potential target crops. Epiphytes can be, for example, gram-positive or gram-negative bacteria.

It is further recognized that whole, i.e., unlysed, cells of the transformed microorganism can be treated with reagents that prolong the activity of the polypeptide produced in the microorganism when the microorganism is applied to the environment of a target plant. A secretion signal sequence may be used in combination with the gene of interest such that the resulting enzyme is secreted outside the microorganism for presentation to the target plant.

In this manner, a gene encoding a defensive agent of the invention may be introduced via a suitable vector into a microbial host, and said transformed host applied to the environment, plants, or animals. Microorganism hosts that are known to occupy the "phytosphere" (phylloplane, phyllosphere, rhizosphere, and/or rhizoplane) of one or more crops of interest may be selected for transformation. These microorganisms are selected so as to be capable of successfully competing in the particular environment with the wild-type microorganisms, to provide for stable maintenance and expression of the gene expressing the detoxifying polypeptide, and for improved protection of the enzymes of the invention from environmental degradation and inactivation.

Such microorganisms include bacteria, algae, and fungi. Of particular interest are microorganisms, such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*; fungi, particularly yeast, e.g., *Saccharomyces, Pichia, Cryptococcus, Kluyveromyces, Sporobolomyces, Rhodotorula, Aureobasidium*, and *Gliocladium*. Of particular interest are such phytosphere bacterial species as *Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae*, and *Aureobasidium pullulans.*

Illustrative prokaryotes, both Gram-negative and -positive, include Enterobacteriaceae, such as *Escherichia, Erwinia, Shigella, Salmonella*, and *Proteus*; Bacillaceae; Rhizobiaceae, such as *Rhizobium*; Spirillaceae, such as photobacterium, *Zymomonas, Serratia, Aeromonas, Vibrio, Desulovibrio, Spirillum*; Lactobacillaceae; Pseudomonadaceae, such as *Pseudomonas* and *Acetobacter*; Azotobacteraceae; and Nitrobacteraceae. Among eukaryotes are fungi, such as *Phycomycetes* and *Ascomycetes*, which includes yeast, such as *Saccharomyces* and *Schizosaccharomyces*; and *Basidiomycetes* yeast, such as *Rhodotorula, Aureobasidium, Sporobolomyces*, and the like.

In an embodiment of the invention, the defensive agents of the invention may be used as a pharmaceutical compound for treatment of fungal and microbial pathogens in humans and other animals. Diseases and disorders caused by fungal and microbial pathogens include but are not limited to fungal meningoencephalitis, superficial fungal infections, ringworm, Athlete's foot, histoplasmosis, candidiasis, thrush, coccidioidoma, pulmonary *cryptococcus*, trichosporonosis, piedra, tinea nigra, fungal keratitis, onychomycosis, tinea capitis, chromomycosis, aspergillosis, endobronchial pulmonary aspergillosis, mucormycosis, chromoblastomycosis, dermatophytosis, tinea, fusariosis, pityriasis, mycetoma, pseudallescheriasis, and sporotrichosis.

The compositions of the invention may be used as pharmaceutical compounds to provide treatment for diseases and disorders associated with, but not limited to, the following fungal pathogens: *Histoplasma capsulatum, Candida* spp. (*C. albicans, C. tropicalis, C. parapsilosis, C. guilliermondii, C. glabrata/Torulopsis glabrata, C. krusei, C. lusitaniae*), *Aspergillus fumigatus, A. flavus, A. niger, Rhizopus* spp., *Rhizomucor* spp., *Cunninghamella* spp., *Apophysomyces* spp., *Saksenaee* spp., *Mucor* spp., and *Absidia* spp. Efficacy of the compositions of the invention as anti-fungal treatments may be determined through anti-fungal assays known to one of skill in the art.

The defensive agents may be administered to a patient through numerous means. Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1 μg/kg to about 15 mg/kg (e.g., 0.1 to 20 mg/kg) of antibody is an initial candidate dosage for administration to the patient, whether, for example, by one or more separate administrations, or by continuous infusion. A typical daily dosage might range from about 1 μg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

"Treatment" is herein defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A "therapeutic agent" includes, but is not limited to, small molecules, peptides, antibodies, ribozymes and antisense oligonucleotides.

The defensive agents of the invention can be used for any application including coating surfaces to target microbes. In this manner, target microbes include human pathogens or microorganisms. Surfaces that might be coated with the defensive agents of the invention include carpets and sterile medical facilities. Polymer bound polypeptides of the invention may be used to coat surfaces. Methods for incorporating compositions with anti-microbial properties into polymers are known in the art. See U.S. Pat. No. 5,847,047, herein incorporated by reference.

An isolated polypeptide of the invention can be used as an immunogen to generate antibodies that bind defensive agents using standard techniques for polyclonal and monoclonal antibody preparation. The full-length defensive agents can be used or, alternatively, the invention provides antigenic peptide fragments of defensive agents for use as immunogens. The antigenic peptide of a defensive agent comprises at least 8, preferably 10, 15, 20, or 30 amino acid residues of the amino acid sequence shown in SEQ ID NO:2, 4, 6, 8, 10, 12, 14, 16, 22, 23, 25, 26, 28, 29, 31, 32, 34, 35, 37, 38, 40, 41, 43, 44, 46, 47, 49, 50, 52, 53, 55, 56, 58, 59, 61, 62, 64, 65, 67, 68, 70, 71, 73, 74, 76, 77, 79, 80, 82, 83, 85, 86, 88, 89, 91, 92, 94, 95, 96, 97, 98, 99, 101, 103, 105, 107, 109, 111, 113, 115, 117, 119, 121, 123, 125, or 127, and encompasses an epitope of a defensive agent such that an antibody raised against the peptide forms a specific immune complex with the anti-microbial polypeptides. Preferred epitopes encompassed by the antigenic peptide are regions of defensive agents that are located on the surface of the protein, e.g., hydrophilic regions.

Accordingly, another aspect of the invention pertains to anti-defensive agent polyclonal and monoclonal antibodies that bind a defensive agent. Polyclonal defensive agent-like antibodies can be prepared by immunizing a suitable subject (e.g., rabbit, goat, mouse, or other mammal) with a defensive agent-like immunogen. The anti-defensive agent antibody titer in the immunized subject can be monitored over time by standard techniques, such as with an enzyme linked immunosorbent assay (ELISA) using immobilized anti-microbial polypeptides. At an appropriate time after immunization, e.g., when the anti-defensive agent antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol. Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77–96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:55052; Kenneth (1980) in *Monoclonal Antibodies: A New Dimension In Biological Analyses* (Plenum Publishing Corp., NY; and Lerner (1981) *Yale J. Biol. Med.*, 54:387–402).

Alternative to preparing monoclonal antibody-secreting hybridomas, a monoclonal anti-defensive agent-like antibody can be identified and isolated by screening a recombinant combinatorial immunoglobulin library (e.g., an antibody phage display library) with a defensive agent to thereby isolate immunoglobulin library members that bind the defensive agent. Kits for generating and screening phage display libraries are commercially available (e.g., the Pharmacia *Recombinant Phage Antibody System*, Catalog No. 27-9400–01; and the Stratagene® SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734. The antibodies can be used to identify homologs of the defensive agents of the invention.

The following examples are offered by way of illustration and not by way of limitation.

EXPERIMENTAL

Example 1

Bioassay for Fungicidal Activity of *Manduca sexta* Hemolymph Polypeptides

After resolution by liquid chromatography (LC), the various pathogen induced *M. sexta* polypeptide-containing fractions were assayed for fungicidal activity against the plant pathogens *M. grisea, R. solani*, and *F. verticilloides*. The LC fractions were first lyophilized in 96-well microtitre plates. A suspension of 100 μl of *M. grisea* (or other named pathogen), at the standard fungal growth assay concentration (2500 spores/ml), was added to the polypeptide containing microtitre plate wells, and the plates sealed with Borden® Sealwrap™ wrap. The plates were then placed at 28° C. in a dark chamber for 24 hours. Hyphal growth was monitored using a dissecting microscope. The polypeptides contained in the wells that lacked hyphal growth, or that displayed reduced hyphal growth compared to control wells, were considered to possess fungicidal activity. Hyphal growth was scored again, 48 hours post inoculation, for a final determination of fungicidal activity.

Example 2

Induction of Antimicrobial Response in *Manduca sexta*

Fifth instar *M. sexta* larvae were injected intersegmentally with 20 μl of a highly concentrated suspension of *M. grisea* hyphae and spores previously scraped from an agar plate colony. The larvae were then placed on fresh diet and allowed to recover. After 24, 48, and 72 hours, hemolymph was collected from the larvae by clipping off a proleg using fine surgical scissors over a sheet of Parafilm™ film. Approximately 1 ml/insect can be collected in this way. The hemolymph was transferred to a 50 ml conical flask and placed on ice while the remaining larvae were being processed. Once all larvae have been processed, phenyl thiolurea was added to a final concentration of 20 mM. Aprotinin was also added to the sample (final concentration 20 μg/ml). The samples were centrifuged (3000 rpm) for 5 minutes to pellet cells. The remaining supernatant (hemolymph) was subjected to solid-phase extraction using Supelco Discovery® DSC-18 solid-phase extraction columns. The columns are preconditioned using 100% methanol, equilibrated using 100% Solvent A (5% acetonitrile, 0.1% TFA; 1 column volume) before the sample is loaded. After the hemolymph (supernatant) filters through, the column is washed with Solvent A before eluting with one column volume of 60% Solvent B/40% Solvent A (Solvent B: 95% acetonitrile, 0.1% TFA). The collected eluent is frozen at −80° C. and lyophilized to dryness. Hemolymph samples are then resuspended in a small volume of water (usually 200–500 μL) and a BCA assay is done to determine protein concentration. Following the solid-phase fractionation step, the hemolymph samples are fractionated by HPLC and tested by bioassay.

Induction of *M. sexta* with *B. bassiana* and *R. solani* was performed similarly.

Corresponding pathogen (*M. grisea; B. bassiana; R. solani*) induced *M. sexta* cDNA libraries were constructed according to standard protocols. Briefly, total RNA was isolated from the fatbodies of pathogen induced *M. sexta*. The mRNAs were isolated using an mRNA purification kit (BRL) according to the manufacture's instructions. The cDNA libraries were constructed using the ZAP-cDNA® synthesis kit and the pBluescript™ phagemid (Stratagene®).

Example 3

HPLC-Fractionation of Polypeptides from *Magnaportha grisea* Induced *Manduca sexta* Hemolymph Hemolymph from *M. grisea* induced *M. sexta* larvae (see Example 2) was fractionated on HP-1100 HPLC, using a Vydac® C4 (4.6–250 mm) column (FIG. 3). A gradient system was used to elute bound proteins. The gradient conditions are indicated below. Fractions were collected at one minute intervals into a 96-well microtiter plate and were assayed for fungicidal activity against *M. grisea* (see Example 1).

This protocol was also followed for fractionation of polypeptides from *B. bassiana* and *R. solani* induced *M. sexta* hemolymph. The bioassay for fungicidal activity (Example 1) was also conducted using the plant pathogens *R. solani* and *F. verticilloides.*

Gradient Conditions:

Solvent
Solvent A: 5% Acetonitrile, 0.1% TFA
Solvent B: 95% Acetonitrile, 0.1% TFA Flow Rate
0.6 ml/min Gradient
0–60% B over 70 minutes

Example 4

Microbore Purification of the Fungicidal Polypeptide, Mag1

After fractionation by HPLC, those fractions from Example 3 possessing fungicidal activity (47–52 min fractions) were further separated by microbore LC (Michrom Bioresources, Inc., Auburn, Calif.) using a Vydac® C4 column (−150 mm). The gradient conditions are indicated below. The column eluant was collected in such a manner as to best resolve the peaks with the highest polypeptide content (FIG. 4). The eluted polypeptides were assayed for fungicidal activity against *M. grisea* (See Example 1). The polypeptide fraction containing the greatest fungicidal activity is indicated with an arrow.

Gradient Conditions:

Solvents
Solvent A: 5% Acetonitrile, 0.1% TFA
Solvent B: 95% Acetonitrile, 0.1% TFA Flow Rate 50 µl/min Gradient 5–65% solvent B in 70 minutes The polypeptide fraction containing the greatest fungicidal activity (indicated with an arrow in FIG. 4 was further resolved using microbore-LC (Michrom Bioresources, Inc., Auburn, Calif.) on a Vydac® C18 (1–150 mm) column (FIG. 5). The gradient conditions follow. Again the polypeptide-containing fractions were assayed for fungicidal activity against *M. grisea* (See Example 1). (The resulting purified polypeptide was designated Mag1.)

Gradient Conditions

Solvents

Solvent A: 5% Acetonitrile, 0.1% HFBA

Solvent B: 95% Acetonitrile, 0.1% HFBA

Flow Rate

50 µl/min

Gradient

5–65% solvent B in 70 minutes

This protocol was also followed for microbore purification of fungicidal polypeptides identified in *B. bassiana* and *R. solani* induced *M. sexta* hemolymph. The bioassay for fungicidal activity (Example 1) was also conducted using the plant pathogens *R. solani* and *F. verticilloides*.

Example 5

Molecular Weight Determination of Mag1

The molecular weight of the isolated Mag1 polypeptide from Example 4 was determined using Liquid Chromatography-Mass Spectrophotometry (LC-MS). The molecular mass of Mag1 was determined using electrospray mass spectrometry on a Micromass® platform LCZ mass spectrometer (Micromass, Manchester, UK). Microbore LC (Michrom Bioresources, Auburn, Calif.) delivered the protein and mobile phase (acetonitrile/water) using a reversed phase column. Spectra were obtained in positive ion mode using a capillary voltage of 3.5 kV, a cone voltage of 45V, and a source temperature of 90° C. Spectra scanned over a range of 600–3000 at a rate of 3.5 s/scan. Molecular masses were determined using the maximum entropy deconvolution algorithm (MaxEnt) to transform the m/z range 600–3000 to give a true mass scale spectrum. Mass calibration was performed using horse heart myoglobin.

A similar protocol was performed for the other polypeptides of the invention.

Example 6

Lys-C Endoproteinase Digestion of Mag1

Sequencing grade lyophilized endoproteinase Lys-C (Boehringer Mannheim) was reconstituted in 50 µl redistilled water resulting in a buffer concentration of 50 mM Tricine pH 8.0, 10 mM EDTA, and 0.5 mg/ml raffinose. The Mag1 polypeptide from Example 4 was dissolved in digestion buffer (25 mM Tris HCl pH 8.5, 1 nM EDTA) to a ratio of 1:50 Lys-C to Mag1 polypeptide by weight. The reaction was allowed to proceed for 20 hours at 37° C. The digested polypeptide was fractionated using a C4 column on a microbore-HPLC with a gradient of 5–65% acetonitrile in 0.1% TFA over 70 minutes at a flow rate of 50 µl/min (FIG. 6). Four isolated fragments were collected and submitted for N-terminal sequence analysis.

A similar protocol was followed for digestion of the other fungicidal polypeptides of the invention.

Example 7

N-Terminal Amino Acid Sequence Determination of Mag1 Polypeptide Fragments

The N-termini of the isolated Mag1 fragments from Example 6 were sequenced on an ABI Procise® 494 Protein Sequencer, consisting of a chemistry workstation, a PTH analysis system, computer control and an automated sequence calling software. Standard protocols were used to run the system and determine the sequences (see FIG. 7).

The N-terminal amino acid sequences of isolated fragments of the other polypeptides of the invention were determined similarly.

N-terminal peptide sequence is critical in determining the exact or precise processing site for the conversion of the pro-peptide into the mature and active form of the protein (as in this example, Mag1). This is in particular important for secretory proteins.

C-terminal peptide sequence was deduced from both the molecular weight generated by LC-MS of the active protein and the predicted molecular weight of the same encoded polypeptide based of the identified cDNA sequence (in Example 8).

By knowing the precise termini of the mature protein, one can design and construct DNA molecules that encode the entire active mature protein for expression in plants. When necessary, additional plant specific controlling elements and targeting sequences can be tailored and incorporated in the gene design in order to enhance and target the expression of the mature polypeptide in plants.

To ensure the original specificity and functionality of the e.g. Mag1 protein retained in the plant, the expression of the active mature form of the protein in the plant is essential.

Example 8

Isolation of the cDNA Clone Encoding Mag1

Fat bodies were harvested directly into liquid nitrogen before processing. Total RNA from fatbodies of challenged *Manduca sexta* was prepared by pulverizing the tissue with a mortar and pestle in liquid nitrogen and lysing cells in the presence of TRIzol® (Life Technologies, Inc.) according to the manufacturer's protocol. PolyA(+) RNA was oligo(dT)-cellulose affinity purified from total RNA using the mRNA Purification Kit (Amersham Pharmacia Biotech) following the manufacturer's protocol in preparation for cDNA library construction. First strand cDNA synthesis using Superscript II (Life Technologies, Inc.) and subsequent second strand synthesis, linker addition, and directional cloning into restriction sites of pBlueScript™ SK+ plasmid (Stratagene®) was performed according to the instructions provided with the Stratagene® cDNA kit (Stratagene®). cDNA was purified using a cDNA column (Life Technologies, Inc.) immediately prior to ligation into the vector.

Sequencing of the cDNA library clones was performed using the ABI PRISM® Big Dye Terminator Cycle Sequencing Ready Kit with FS AmpliTaq DNA polymerase (Perkin Elmer™) and analyzed on an ABI Model 373 Automated DNA Sequencer. The Mag1 gene sequence was identified by sequencing about 2000 clones of the cDNA library prepared from mRNA derived from the fatbodies of challenged *M. sexta*. Amino acid sequences derived from amino termini of the complete peptide or proteolytic cleavage products were used to compare to the corresponding cDNA clone sequence library translated in the six possible frames. Sequences containing 100% identity to the N-terminal amino acid sequences were fully translated and their predicted MW compared to the MW of the purified Mag1 protein. Sequences with comparable MWs were identified as probably encoding Mag1.

Example 9

Isolation of the cDNA Clone Encoding a Polypeptide of Interest

The N-terminal amino acid sequence tags of a polypeptide of interest are used to identify cDNA clones encoding the polypeptide. Degenerate oligonucleotides encoding the amino acid sequence tags of the polypeptide are used as probes to detect cDNA's encoding the polypeptide in a pathogen induced *M. sexta* cDNA library (see Example 2). In this manner a full-length cDNA encoding the polypeptide of interest is isolated and sequenced. Complete sequencing of the identified cDNA clone is performed to confirm that it encodes the purified polypeptide. Confirmation is provided by the predicted molecular weight of the cDNA encoded polypeptide being the same as the molecular weight of the polypeptide generated by LC-MS.

Example 10

Construction of Recombinant Baculovirus Expressing Fungicidal Polypeptides

The nucleotide sequences encoding the polypeptides of the invention may be introduced into the baculovirus genome itself. For this purpose the nucleotide sequences may be placed under the control of the polyhedrin promoter, the IE1 promoter, or any other one of the baculovirus promoters. The cDNA, together with appropriate leader sequences is then inserted into a baculovirus transfer vector using standard molecular cloning techniques. Following transformation of *E. coli* DH5α, isolated colonies are chosen and plasmid DNA is prepared and is analyzed by restriction enzyme analysis. Colonies containing the appropriate fragment are isolated, propagated, and plasmid DNA is prepared for cotransfection.

Example 11

Expression of Fungicidal Polypeptides in Insect Cells

The polypeptides of the invention may be expressed in insect cells. For this purpose the *Spodoptera frugiperda* cells (Sf-9 or Sf-21) are propagated in ExCell® 401 media (JRH Biosciences™, Lenexa, Kans.), or a similar media, supplemented with 3.0% fetal bovine serum. Lipofectin® (50 μL at 0.1 mg/mL, Gibco BRL) is added to a 50 μL aliquot of the transfer vector containing the antimicrobial nucleotide sequences (500 ng) and linearized polyhedrin-negative AcNPV (2.5 μg, Baculogold® viral DNA, Pharmingen®, San Diego, Calif.). Sf-9 cells (approximate 50% monolayer) are co-transfected with the viral DNA/transfer vector solution. The supernatant fluid from the co-transfection experiment is collected at 5 days post-transfection and recombinant viruses are isolated employing standard plaque purification protocols, wherein only polyhedrin-positive plaques are selected (O'Reilly et al. (1992), *Baculovirus Expression Vectors: A Laboratory Manual*, W.H. Freeman and Company, New York). Sf-9 cells in 35 mm petri dishes (50% monolayer) are inoculated with 100 μL of a serial dilution of the viral suspension, and supernatant fluids are collected at 5 days post infection. In order to prepare larger quantities of virus for characterization, these supernatant fluids are used to inoculate larger tissue cultures for large scale propagation of recombinant viruses. Expression of the encoded fungicidal polypeptide by the recombinant baculovirus can be confirmed using a bioassay (such as described in Example 4), LC-MS, or antibodies.

Example 12

Expression of Fungicidal Peptides in *Pichia*

The nucleotide sequences encoding the polypeptides of the invention may be expressed in *Pichia* under constitutive or inducible promoter control and targeted to remain intracellular or to be secreted into the media. The nucleotide sequences are cloned into a *Pichia* expression vector using standard molecular techniques. Transformation of *Pichia* strains (e.g. X-33, GS115, SMD1168, KM71, etc.—Invitrogen™, Carlsbad, Calif.) involves linearization of the construct and introduction of the DNA into transformation competent *Pichia* cells by chemical means or by electroporation according to standard protocols. Transformants are selected by either resistance to Zeocin or blasticidin or by their ability to grow on histidine-deficient medium. Small scale expression tests are performed on selected transformants to identify high expressors of the polypeptides of the invention for additional scale up. In an inducible system, such as when the peptide is under control of the AOX1 promoter, transformants are grown in media with glycerol as a carbon source and induced by growth in media containing methanol instead of glycerol. Continuous induction over a period of 24–120 hrs is achieved by addition of methanol (0.5% final conc.) every 24 hr. Functional expression of the polypeptide is confirmed by LC-MS analysis/purification and bioassay.

Example 13

Expression of Fungicidal Polypeptides in Bacteria

The nucleotide sequences encoding the polypeptides of the invention may be expressed in bacteria and the peptides targeted for intracellular or extracellular expression. The cDNA's may be cloned into a suitable bacterial expression vector (e.g. pET vectors (Novagen®, Madison, Wis.) under constitutive or inducible promoter control using standard molecular cloning techniques. The plasmid containing the gene of interest is introduced into transformation competent bacteria cells using standard protocols for chemical transformation or electroporation and the transformants are selected using antibiotic resistance. In addition to traditional *E. coli* strains commonly used for transformation, mutant strains such as Origami™ (Novagen®, Madison, Wis.) that are permissive for disulfide bond formation can be used, especially with cysteine-rich peptides to express functional peptides. Inducible systems such as *E. coli* strains bearing the T7 RNA polymerase gene (lambda-DE3 lysogen) can be used in which expression of the gene of interest under a T7 promoter is induced by addition of IPTG for variable periods of time. Expression and activity of the polypeptides are confirmed by LC-MS and bioassays.

Example 14

Transformation of Rice Embryogenic Callus by Bombardment and Regeneration of Transgenic Plants Embryogenic callus cultures derived from the scutellum of germinating seeds serve as the source material for transformation experiments. This material is generated by germinating sterile rice seeds on a callus initiation media (MS salts, Nitsch and Nitsch vitamins, 1.0 mg/l 2,4-D and 10 µM AgNO$_3$) in the dark at 27–28° C. Embryogenic callus proliferating from the scutellum of the embryos is then transferred to CM media (N6 salts, Nitsch and Nitsch vitamins, 1 mg/l 2,4-D, Chu et al., 1985, *Sci. Sinica* 18:659–668). Callus cultures are maintained on CM by routine sub-culture at two week intervals and used for transformation within 10 weeks of initiation.

Callus is prepared for transformation by subculturing 0.5–1.0 mm pieces approximately 1 mm apart, arranged in a circular area of about 4 cm in diameter, in the center of a circle of Whatman® #541 paper placed on CM media. The plates with callus are incubated in the dark at 27–28° C. for 3–5 days. Prior to bombardment, the filters with callus are transferred to CM supplemented with 0.25 M mannitol and 0.25 M sorbitol for 3 hours in the dark. The petri dish lids are then left ajar for 20–45 minutes in a sterile hood to allow moisture on tissue to dissipate.

Circular plasmid DNA from two different plasmids one containing the selectable marker for rice transformation and one containing the nucleotide of the invention, are co-precipitated onto the surface of gold particles. To accomplish this, a total of 10 µg of DNA at a 2:1 ratio of trait:selectable marker DNAs is added to a 50 µl aliquot of gold particles resuspended at a concentration of 60 mg/ml. Calcium chloride (50 µl of a 2.5 M solution) and spermidine (20 µl of a 0.1 M solution) are then added to the gold-DNA suspension as the tube is vortexing for 3 minutes. The gold particles are centrifuged in a microfuge for 1 sec and the supernatant removed. The gold particles are then washed twice with 1 ml of absolute ethanol and then resuspended in 50 µl of absolute ethanol and sonicated (bath sonicator) for one second to disperse the gold particles. The gold suspension is incubated at −70° C. for five minutes and sonicated (bath sonicator) if needed to disperse the particles. Six microliters of the DNA-coated gold particles are then loaded onto mylar macrocarrier disks and the ethanol is allowed to evaporate.

At the end of the drying period, a petri dish containing the tissue is placed in the chamber of the PDS-1000/He. The air in the chamber is then evacuated to a vacuum of 28–29 inches Hg. The macrocarrier is accelerated with a helium shock wave using a rupture membrane that bursts when the He pressure in the shock tube reaches 1080–1100 p.s.i. The tissue is placed approximately 8 cm from the stopping screen and the callus is bombarded two times. Five to seven plates of tissue are bombarded in this way with the DNA-coated gold particles. Following bombardment, the callus tissue is transferred to CM media without supplemental sorbitol or mannitol.

Within 3–5 days after bombardment the callus tissue is transferred to SM media (CM medium containing 50 mg/l hygromycin). To accomplish this, callus tissue is transferred from plates to sterile 50 ml conical tubes and weighed. Molten top-agar at 40° C. is added using 2.5 ml of top agar/100 mg of callus. Callus clumps are broken into fragments of less than 2 mm diameter by repeated dispensing through a 10 ml pipette. Three milliliter aliquots of the callus suspension are plated onto fresh SM media and the plates incubated in the dark for 4 weeks at 27–28° C. After 4 weeks, transgenic callus events are identified, transferred to fresh SM plates and grown for an additional 2 weeks in the dark at 27–28° C.

Growing callus is transferred to RM1 media (MS salts, Nitsch and Nitsch vitamins, 2% sucrose, 3% sorbitol, 0.4% Gelrite™ gelling agent+50 ppm hyg B) for 2 weeks in the dark at 25° C. After 2 weeks the callus is transferred to RM2 media (MS salts, Nitsch and Nitsch vitamins, 3% sucrose, 0.4% Gelrite™ gelling agent+50 ppm hyg B) and placed under cool white light (~40 µEm$^{-2}$s$^{-1}$) with a 12 hr photoperiod at 25° C. and 30–40% humidity. After 2–4 weeks in the light, callus generally begins to organize, and form shoots. Shoots are removed from surrounding callus/media and gently transferred to RM3 media (½×MS salts, Nitsch and Nitsch vitamins, 1% sucrose+50 ppm hygromycin B) in phytatrays (Sigma® Chemical Co., St. Louis, Mo.) and incubation is continued using the same conditions as described in the previous step.

Plants are transferred from RM3 to 4" pots containing Metro mix 350 after 2–3 weeks, when sufficient root and shoot growth has occurred. Plants are grown using a 12 hr/12 hr light/dark cycle using ~30/18° C. day/night temperature regimen.

Example 15

Transformation of Maize by Particle Bombardment and Regeneration of Transgenic Plants Immature maize embryos from greenhouse donor plants are bombarded with a plasmid containing a nucleotide sequence of the invention operably linked to a ubiquitin promoter and the selectable marker gene PAT (Wohlleben et al. (1988) *Gene* 70:25–37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox™ bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the nucleotide sequence of the invention operably linked to a ubiquitin promoter is made. This plasmid DNA plus plasmid DNA containing a PAT selectable marker is precipitated onto 1.1 µm (average diameter) tungsten pellets using a CaCl$_2$ precipitation procedure as follows:

100 µl prepared tungsten particles in water
10 µl (1 µg) DNA in Tris EDTA buffer (1 µg total DNA)
100 µl 2.5M CaCl$_2$
10 µl 0.1M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 µl 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for expression of the nucleotide sequence encoding the fungicidal polypeptide of the invention, or for the presence of the fungicidal polypeptide by immunological methods, or for fungicidal activity by assays known in the art, described supra herein.

Bombardment and Culture Media

Bombardment medium (560Y) comprises 4.0 g/l N6 basal salts (Sigma® C-1416), 1.0 ml/l Eriksson's Vitamin Mix (1000× Sigma®-1511), 0.5 mg/l thiamine HCl, 120.0 g/l sucrose, 1.0 mg/l 2,4-D, and 2.88 g/l L-proline (brought to volume with D-I H$_2$O following adjustment to pH 5.8 with KOH); 2.0 g/l Gelrite™ gelling agent (added after bringing to volume with D-I H$_2$O); and 8.5 mg/l silver nitrate (added after sterilizing the medium and cooling to room temperature). Selection medium (560R) comprises 4.0 g/l N6 basal salts (Sigma®C-1416), 1.0 ml/l Eriksson's Vitamin Mix (1000× Sigma®-1511), 0.5 mg/l thiamine HCl, 30.0 g/l sucrose, and 2.0 mg/l 2,4-D (brought to volume with D-I H$_2$O following adjustment to pH 5.8 with KOH); 3.0 g/l Gelrite™ gelling agent (added after bringing to volume with D-I H$_2$O); and 0.85 mg/l silver nitrate and 3.0 mg/l bialaphos (both added after sterilizing the medium and cooling to room temperature).

Plant regeneration medium (288J) comprises 4.3 g/l MS salts (Gibco®11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I H$_2$O) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I H$_2$O after adjusting to pH 5.6); 3.0 g/l Gelrite™ gelling agent (added after bringing to volume with D-I H$_2$O); and 1.0 mg/l indoleacetic acid and 3.0 mg/l bialaphos (added after sterilizing the medium and cooling to 60° C.). Hormone-free medium (272V) comprises 4.3 g/l MS salts (Gibco® 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H$_2$O), 0.1 g/l myo-inositol, and 40.0 g/l sucrose (brought to volume with polished D-I H$_2$O after adjusting pH to 5.6); and 6 g/l bacto-agar (added after bringing to volume with polished D-I H$_2$O), sterilized and cooled to 60° C.

Example 16

*Agrobacterium*-Mediated Transformation of Maize and Regeneration of Transgenic Plants For *Agrobacterium*-mediated transformation of maize with a plant-optimized nucleotide sequence of the invention, preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the plant-optimized nucleotide sequence of the invention to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

Example 17

Transformation of Soybean Embryos and Regeneration of Transgenic Plants

Soybean embryos are bombarded with a plasmid containing a nucleotide sequence of the invention operably linked to a ubiquitin promoter as follows. To induce somatic embryos, cotyledons, 3–5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327:70–73, U.S. Pat. No. 4,945,050). A DuPont™ Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188), and the 3' region of the nopaline synthase gene from the T-DNA of the Ti plasmid of *Agrobacterium tumefaciens*. The expression cassette comprising the nucleotide sequence of the invention operably linked to the ubiquitin promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl $CaCl_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 18

Transformation of Sunflower Meristem Tissue and Regeneration of Transgenic Plants Sunflower meristem tissues are transformed with an expression cassette containing the nucleotide sequence of the invention operably linked to a ubiquitin promoter as follows (see also European Patent Number EP 0 486233, herein incorporated by reference, and Malone-Schoneberg et al. (1994) *Plant Science* 103:199–207). Mature sunflower seed (*Helianthus annuus* L.) are dehulled using a single wheat-head thresher. Seeds are surface sterilized for 30 minutes in a 20% Clorox™ bleach solution with the addition of two drops of Tween™ 20 per 50 ml of solution. The seeds are rinsed twice with sterile distilled water.

Split embryonic axis explants are prepared by a modification of procedures described by Schrammeijer et al. (Schrammeijer et al. (1990) *Plant Cell Rep.* 9:55–60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant.*, 15:473–497), Shepard's vitamin additions (Shepard (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzyl-aminopurine (BAP), 0.25 mg/l indole-3-acetic acid (IAA), 0.1 mg/l gibberellic acid ($GA_3$), pH 5.6, and 8 g/l Phytagar™ agar.

The explants are subjected to microprojectile bombardment prior to *Agrobacterium* treatment (Bidney et al. (1992) *Plant Mol. Biol.* 18:301–313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the nucleotide sequence of the invention operably linked to the ubiquitin promoter is introduced into *Agrobacterium* strain EHA105 via freeze-thawing as described by Holsters et al. (1978) *Mol. Gen. Genet.* 163:181–187. This plasmid further comprises a kanamycin selectable marker gene (i.e., nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The *Agrobacterium* cells are pelleted and resuspended at a final $OD_{600}$ of 0.5 in an inoculation medium comprised of 12.5 mM MES pH 5.7, 1 gm/l $NH_4Cl$, and 0.3 gm/l $MgSO_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for expression of the nucleotide sequence encoding the fungicidal polypeptide of the invention, the presence of the fungicidal polypeptide by immunological methods, or for fungicidal activity by assays known in the art, described supra herein.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% Gelrite™ gelling agent, pH 5.6) and grown under conditions described for explant culture. The upper portion of the seedling is removed, a 1 cm vertical slice is made in the hypocotyl, and the transformed shoot inserted into the cut. The entire area is wrapped with Parafilm™ film to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by the fungicidal activity analysis of leaf extracts while transgenic seeds harvested from NPTII-positive $T_0$ plants are identified by fungicidal activity analysis of small portions of dry seed cotyledon.

An alternative sunflower transformation protocol allows the recovery of transgenic progeny without the use of chemical selection pressure. This method is generally used in cases where the nucleotide sequences of the present invention are operably linked to constitutive or inducible promoters. Seeds are dehulled and surface-sterilized for 20 minutes in a 20% Clorox™ bleach solution with the addition of two to three drops of Tween™ 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar™ agar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar™ agar), and then cultured on the medium for 24 hours in the dark.

Approximately 18.8 mg of 1.8 µm tungsten particles are resuspended in 150 µl absolute ethanol. After sonication, 8 µl of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/l yeast extract, 10 g/l Bactopeptone, and 5 g/l NaCl, pH 7.0) in the presence of 50 µg/l kanamycin is resuspended in an inoculation medium (12.5 mM 2-mM 2-(N-morpholino)ethanesulfonic acid, MES, 1 g/l NH$_4$Cl and 0.3 g/l MgSO$_4$ at pH 5.7) to reach a final concentration of 4.0 at OD 600. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 µg/ml cefotaxime). The plantlets are cultured on the medium for about two weeks under 16-hour day and 26° C. incubation conditions.

Explants (around 2 cm long) from two weeks of culture in 374C medium are screened for the expression of the nucleotide sequence of the invention or the presence of the encoded polypeptide of the invention by immunological methods or fungicidal activity, or the like. After positive explants are identified, those shoots that fail to exhibit fungicidal activity are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for a fungicidal polypeptide of the invention are grafted to Pioneer® hybrid 6440 in vitro-grown sunflower seedling rootstock. The rootstocks are prepared in the following manner. Seeds are dehulled and surface-sterilized for 20 minutes in a 20% Clorox™ bleach solution with the addition of two to three drops of Tween™ 20 per 100 ml of solution, and are rinsed three times with distilled water. The sterilized seeds are germinated on the filter moistened with water for three days, then they are transferred into 48 medium (half-strength MS salt, 0.5% sucrose, 0.3% Gelrite™ gelling agent pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with Parafilm™ film. After one week of culture on the medium, grafted plants are transferred to soil. In the first two weeks, they are maintained under high humidity conditions to acclimatize to a greenhouse environment.

Example 19

Preparation of Antibodies

Standard methods for the production of antibodies were used such as those described in Harlow and Lane (1988) *Antibodies: A Laboratory Manual* (Cold Spring Harbor, N.Y.: Cold Spring Harbor Laboratory), incorporated herein in its entirety by reference. Specifically, antibodies for polypeptides of the invention were produced by injecting female New Zealand white rabbits (Bethyl Laboratory, Montgomery, Tex.) six times with 100 micrograms of denatured purified polypeptide.

Animals were then bled at two week intervals. The antibodies were purified by affinity-chromatography with Affigel 15 (Bio-Rad® Laboratories, Inc., Hercules, Calif.)—immobilized antigen as described by Harlow and Lane (1988) *Antibodies: A Laboratory Manual*, Cold Spring Harbor, N.Y. The affinity column was prepared with purified polypeptide essentially as recommended by the manufacturer. Immune detection of antigens on PVDF blots was carried out following the protocol of Meyer et al. (1988) *J. Cell. Biol.* 107:163; incorporated herein in its entirety by reference, using the ECL kit from Amersham™ Corporation (Arlington Heights, Ill.).

Example 20

Construction of Fus1 Transformation Vector

A synthetic version of the Fus1 gene corresponding to the mature Fus1 peptide was constructed with a codon-bias representative of *Manduca sexta* (SEQ ID NO:120 and SEQ ID NO:122). The codon preference selected for Fus1 was derived from the Kazusa codon usage database (available from www.Kazusa.or.jp/codon/). The BAA signal sequence was added to Fus1 to facilitate export of out of the cell and into the intercellular space (Rahmatullah R J et al. (1989) *Plant Mol. Biol.* 12(1):119–121). The BAA-Fus1 amino acid sequence is set forth in SEQ ID NO:121 and SEQ ID NO:123. Strong constitutive promoters were chosen to express Fus1 in tissues susceptible to *F. verticilloides*. BAA-Fus1 (SEQ ID NO:120) was subsequently subcloned into the corresponding sites of vectors containing either the maize ubiquitin promoter: ubi-intron or the maize h2B promoter: ubi-intron (U.S. Pat. No. 6,177,611, herein incorporated by reference). BAA-Fus1 was placed behind the indicated promoter with a 3' sequence corresponding to the pinII terminator. This cassette is flanked by non-compatible restriction enzyme sites designed to directionally clone the cassette into a binary plasmid containing the selectable marker gene cassette 35S-PAT-35S. The restriction enzyme sites were used to subclone the promoter/intron:BAA-Fus1:pinII ter cassette into a binary plasmid for corn transformation.

Example 21

Construction of Fus2 Transformation Vectors

A synthetic version of Fus2 operably linked to a modified barley alpha amylase (BAA) signal peptide was constructed with a codon-bias representative of *Streptomyces coelicolor* (SEQ ID NO:124 and SEQ ID NO:126). *S. coelicolor* codon usage was chosen because of its overall similarity to the codon usage observed in plants. The codon preference selected for Fus2 was derived from the Kazusa codon usage database (available from www.Kazusa.or.jp/codon/). See also Tables 1 and 2. The BAA signal sequence was added to Fus2 to facilitate export of Fus2 out of the cell and into the intercellular space. Modifications to the 3' end of the signal peptide were made to achieve correct signal peptide cleavage as predicted by the SIGNALP (Version 1.1) program (Center for Biological Sequence Analysis, Technical University of Denmark). The BAA-Fus2 amino acid sequence is set forth in SEQ ID NO:125 and SEQ ID NO:127. The synthetic gene was constructed using a series of overlapping complementary oligonucleotides that were annealed together, Klenow treated to repair the gaps, and PCR amplified using primers corresponding to 5' and 3' ends of the synthetic gene. Restriction enzyme sites were incorporated into the PCR primers to facilitate gene cloning. The PCR product was TOPO cloned into pCR2.1 (Invitrogen™) and sequence verified. A restriction enzyme fragment containing BAA-Fus2 was subsequently subcloned into the corresponding sites of vectors containing either the maize ubiquitin promoter: ubi-intron or the maize h2B promoter: ubi-intron. The vectors contained a 3' sequence corresponding to the pinII terminator. The BAA-Fus2 fragment was cloned between the indicated promoter and the pinII terminator. Strong constitutive promoters were chosen to express Fus2 in tissues susceptible to *F. verticilloides*. The promoter/intron:BAA-Fus2:pinII ter cassette is flanked by non-compatible restriction enzyme sites designed to directionally clone the cassette into a binary plasmid containing a selectable marker. The restriction enzyme sites were used to subclone the promoter/intron:BAA-Fus2:pinII ter cassette into a binary plasmid for corn transformation.

TABLE 1

*Streptomyces coelicolor* A3(2) [gbbct]:
6257 CDS's (2043281 codons)

fields: [triplet] [frequency: per thousand] ([number])

| | | | | | | | | | | | |
|---|---|---|---|---|---|---|---|---|---|---|---|
| UUU | 0.4 | (863) | UCU | 0.6 | (1266) | UAU | 1.0 | (1962) | UGU | 0.7 | (1448) |
| UUC | 26.0 | (53065) | UCC | 20.2 | (41262) | UAC | 19.5 | (39789) | UGC | 7.0 | (14341) |
| UUA | 0.1 | (128) | UCA | 1.0 | (2137) | UAA | 0.1 | (290) | UGA | 2.4 | (4878) |
| UUG | 2.4 | (4935) | UCG | 13.8 | (28229) | UAG | 0.5 | (1089) | UGG | 15.1 | (30770) |
| CUU | 1.5 | (3129) | CCU | 1.5 | (2995) | CAU | 1.6 | (3366) | CGU | 5.5 | (11183) |
| CUC | 36.6 | (74736) | CCC | 25.4 | (51951) | CAC | 21.5 | (44018) | CGC | 39.1 | (79956) |
| CUA | 0.3 | (657) | CCA | 1.3 | (2633) | CAA | 1.3 | (2593) | CGA | 2.5 | (5124) |
| CUG | 61.3 | (125241) | CCG | 33.6 | (68652) | CAG | 25.1 | (51248) | CGG | 32.0 | (65332) |
| AUU | 0.6 | (1228) | ACU | 1.1 | (2347) | AAU | 0.7 | (1436) | AGU | 1.5 | (3030) |
| AUC | 27.6 | (56340) | ACC | 39.6 | (80826) | AAC | 16.2 | (33191) | AGC | 12.3 | (25187) |
| AUA | 0.7 | (1367) | ACA | 1.6 | (3194) | AAA | 1.0 | (2041) | AGA | 0.8 | (1574) |
| AUG | 15.8 | (32271) | ACG | 18.9 | (38697) | AAG | 19.7 | (40293) | AGG | 3.7 | (7488) |
| GUU | 1.4 | (2905) | GCU | 2.9 | (5908) | GAU | 2.9 | (6024) | GGU | 9.3 | (18920) |
| GUC | 47.2 | (96460) | GCC | 78.6 | (160548) | GAC | 58.0 | (118595) | GGC | 61.4 | (125467) |
| GUA | 2.7 | (5416) | GCA | 5.3 | (10890) | GAA | 8.5 | (17445) | GGA | 7.1 | (14608) |
| GUG | 35.3 | (72144) | GCG | 49.8 | (101831) | GAG | 48.5 | (99056) | GGG | 18.2 | (37288) |

Coding GC 72.38% 1st letter GC 72.74% 2nd letter GC 51.39% 3rd letter GC 93.00%

TABLE 2

*Streptomyces coelicolor* [gbbct]:
2110 CDS's (646333 codons)

fields: [triplet] [frequency: per thousand] ([number])

| | | | | | | | | | |
|---|---|---|---|---|---|---|---|---|---|
| UUU | 0.5 (329) | UCU | 0.8 (496) | UAU | 1.0 (676) | UGU | 0.8 (517) | | |
| UUC | 25.7 (16596) | UCC | 20.1 (12971) | UAC | 19.4 (12521) | UGC | 7.3 (4734) | | |
| UUA | 0.1 (49) | UCA | 1.2 (797) | UAA | 0.2 (105) | UGA | 2.6 (1650) | | |
| UUG | 2.6 (1696) | UCG | 13.5 (8729) | UAG | 0.5 (355) | UGG | 15.2 (9813) | | |
| CUU | 1.9 (1228) | CCU | 1.8 (1178) | CAU | 1.9 (1251) | CGU | 5.6 (3602) | | |
| CUC | 36.2 (23411) | CCC | 25.4 (16419) | CAC | 22.6 (14594) | CGC | 39.2 (25310) | | |
| CUA | 0.5 (304) | CCA | 1.6 (1018) | CAA | 1.7 (1076) | CGA | 2.9 (1885) | | |
| CUG | 59.3 (38346) | CCG | 32.7 (21145) | CAG | 25.8 (16671) | CGG | 31.5 (20333) | | |
| AUU | 0.8 (497) | ACU | 1.4 (925) | AAU | 0.8 (515) | AGU | 1.6 (1023) | | |
| AUC | 27.8 (17997) | ACC | 39.9 (25804) | AAC | 16.2 (10447) | AGC | 12.7 (8194) | | |
| AUA | 0.7 (444) | ACA | 1.9 (1245) | AAA | 1.3 (829) | AGA | 0.8 (537) | | |
| AUG | 16.1 (10392) | ACG | 19.1 (12377) | AAG | 19.8 (12795) | AGG | 3.8 (2441) | | |
| GUU | 1.7 (1086) | GCU | 3.8 (2429) | GAU | 3.5 (2251) | GGU | 9.1 (5867) | | |
| GUC | 46.3 (29904) | GCC | 77.5 (50098) | GAC | 58.2 (37624) | GGC | 58.8 (38034) | | |
| GUA | 2.7 (1767) | GCA | 6.7 (4302) | GAA | 9.6 (6215) | GGA | 7.3 (4689) | | |
| GUG | 33.9 (21929) | GCG | 48.6 (31399) | GAG | 47.9 (30970) | GGG | 17.8 (11502) | | |

Coding GG 71.94% 1st letter GC 72.38% 2nd letter GC 51.28% 3rd letter GC 92.14%

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated polypeptide comprising an amino acid sequence that has at least 90% sequence identity to the amino acid sequence set forth in SEQ ID NO: 2, wherein said polypeptide has antimicrobial activity.

2. The isolated polypeptide of claim 1, wherein said amino acid sequence has at least 95% sequence identity to the amino acid sequence set forth in SEQ ID NO: 2.

3. The isolated polypeptide of claim 1, wherein said amino acid sequence has at least 97% sequence identity to the amino acid sequence set forth in SEQ ID NO: 2.

4. The isolated polypeptide of claim 1, wherein said amino acid sequence has at least 98% sequence identity to the amino acid sequence set forth in SEQ ID NO: 2.

5. The isolated polypeptide of claim 1, wherein said amino acid sequence is set forth in SEQ ID NO: 2.

6. An antimicrobial composition comprising the isolated polypeptide of claim 1 and an acceptable carrier.

* * * * *

SEQUENCE LISTING

<160> NUMBER OF SEQ ID NOS: 127

<210> SEQ ID NO 1
<211> LENGTH: 766
<212> TYPE: DNA
<213> ORGANISM: Manduca sexta
<220> FEATURE:
<221> NAME/KEY: CDS
<222> LOCATION: (1)...(621)

<400> SEQUENCE: 1

```
atg ttc acc aaa ttc gtc gtc ctg gtc tgt ctt ctc gtt ggt gct aag      48
Met Phe Thr Lys Phe Val Val Leu Val Cys Leu Leu Val Gly Ala Lys
  1               5                  10                  15 gct cgg cct cag ctc ggc gct ctc act ttc aat tct gat ggc act tcc      96
Ala Arg Pro Gln Leu Gly Ala Leu Thr Phe Asn Ser Asp Gly Thr Ser
             20                  25                  30 ggg gcg gcc gtc aaa gtt cca ttt ggt ggc aac aag aat aat ata ttt     144
Gly Ala Ala Val Lys Val Pro Phe Gly Gly Asn Lys Asn Asn Ile Phe
         35                  40                  45 agt gct atc ggt ggg gct gat ttt aac gct aat cac aaa ctg agt tct     192
Ser Ala Ile Gly Gly Ala Asp Phe Asn Ala Asn His Lys Leu Ser Ser
     50                  55                  60 gcg act gct gga gta gcg ctt gat aat atc cga ggt cac gga ctc agt     240
Ala Thr Ala Gly Val Ala Leu Asp Asn Ile Arg Gly His Gly Leu Ser
 65                  70                  75                  80 ttg acg gat acc cac atc ccc ggc ttt gga gac aag ttg acg gcg gcc     288
Leu Thr Asp Thr His Ile Pro Gly Phe Gly Asp Lys Leu Thr Ala Ala
                 85                  90                  95
```

```
ggc aag ttg aac ctc ttc cac aac aac aac cac gat ctg acc gcc aac      336
Gly Lys Leu Asn Leu Phe His Asn Asn Asn His Asp Leu Thr Ala Asn
        100                 105                 110 gct ttc gcc acc agg aac atg ccg aac att cct cag gtt cca aac ttc      384
Ala Phe Ala Thr Arg Asn Met Pro Asn Ile Pro Gln Val Pro Asn Phe
            115                 120                 125 aac acc gtt ggt ggc gga ctg gac tac atg ttc aag aac aag gtg ggc      432
Asn Thr Val Gly Gly Gly Leu Asp Tyr Met Phe Lys Asn Lys Val Gly
130                 135                 140 gct tca tta ggc gcc gcg cac act gac ttt atc aac cgc aac gac tac      480
Ala Ser Leu Gly Ala Ala His Thr Asp Phe Ile Asn Arg Asn Asp Tyr
145                 150                 155                 160 tct gtg ggc ggc aag ttg aac ctg ttc cgg aac ccg agc acc tcg ctc      528
Ser Val Gly Gly Lys Leu Asn Leu Phe Arg Asn Pro Ser Thr Ser Leu
                165                 170                 175 gac ttc aac gcc ggc ttt aag aag ttc gac acg ccc ttc atg aga tcc      576
Asp Phe Asn Ala Gly Phe Lys Lys Phe Asp Thr Pro Phe Met Arg Ser
            180                 185                 190 ggc tgg gaa ccc aac atg ggc ttc tcc ctc tcc aag ttc ttc taa          621
Gly Trp Glu Pro Asn Met Gly Phe Ser Leu Ser Lys Phe Phe *
        195                 200                 205 ttactttagt atatctctca gtattatgaa ttgtctttt ttattaatgt aatccgcctt     681
ttgtaccgaa taaatatttt tatataaaaa aaaaaaaaa aaaaaaaaa aaaaaaaaa       741 aaaaaaaaaa aaaaaaaaaa aaaaa                                          766

<210> SEQ ID NO 2
<211> LENGTH: 206
<212> TYPE: PRT
<213> ORGANISM: Manduca sexta

<400> SEQUENCE: 2

Met Phe Thr Lys Phe Val Val Leu Val Cys Leu Leu Val Gly Ala Lys
 1               5                  10                  15

Ala Arg Pro Gln Leu Gly Ala Leu Thr Phe Asn Ser Asp Gly Thr Ser
            20                  25                  30

Gly Ala Ala Val Lys Val Pro Phe Gly Gly Asn Lys Asn Asn Ile Phe
        35                  40                  45

Ser Ala Ile Gly Gly Ala Asp Phe Asn Ala Asn His Lys Leu Ser Ser
    50                  55                  60

Ala Thr Ala Gly Val Ala Leu Asp Asn Ile Arg Gly His Gly Leu Ser
65                  70                  75                  80

Leu Thr Asp Thr His Ile Pro Gly Phe Gly Asp Lys Leu Thr Ala Ala
                85                  90                  95

Gly Lys Leu Asn Leu Phe His Asn Asn Asn His Asp Leu Thr Ala Asn
            100                 105                 110

Ala Phe Ala Thr Arg Asn Met Pro Asn Ile Pro Gln Val Pro Asn Phe
        115                 120                 125

Asn Thr Val Gly Gly Gly Leu Asp Tyr Met Phe Lys Asn Lys Val Gly
130                 135                 140

Ala Ser Leu Gly Ala Ala His Thr Asp Phe Ile Asn Arg Asn Asp Tyr
145                 150                 155                 160

Ser Val Gly Gly Lys Leu Asn Leu Phe Arg Asn Pro Ser Thr Ser Leu
                165                 170                 175

Asp Phe Asn Ala Gly Phe Lys Lys Phe Asp Thr Pro Phe Met Arg Ser
            180                 185                 190
```

```
Gly Trp Glu Pro Asn Met Gly Phe Ser Leu Ser Lys Phe Phe
    195                 200                 205

<210> SEQ ID NO 3
<211> LENGTH: 760
<212> TYPE: DNA
<213> ORGANISM: Manduca sexta
<220> FEATURE:
<221> NAME/KEY: CDS
<222> LOCATION: (34)...(624)
<220> FEATURE:
<221> NAME/KEY: misc_feature
<222> LOCATION: (0)...(0)
<223> OTHER INFORMATION: n = A,T,C or G

<400> SEQUENCE: 3
attcggcacg aggacgatgt ggtgttcgta cca atg gtg gta tca agg gta cgg         54
                                     Met Val Val Ser Arg Val Arg
                                       1               5 cgc gac aca cac ggc tcg gtc acc gtc aac tcg gac ggc acc tcc gga        102
Arg Asp Thr His Gly Ser Val Thr Val Asn Ser Asp Gly Thr Ser Gly
            10                  15                  20 gcg atc gtc aag gtg ccg ttc gca ggc gac gac aag aac atc gtc agc        150
Ala Ile Val Lys Val Pro Phe Ala Gly Asp Asp Lys Asn Ile Val Ser
     25                  30                  35 gcc atc ggt ggc ctc gac ctc gac aag aac ctc aag atg agc ggc gcc        198
Ala Ile Gly Gly Leu Asp Leu Asp Lys Asn Leu Lys Met Ser Gly Ala
 40                  45                  50                  55 aca gcg ggc ttg gct tac gac aac gtc aat gga cac ggc gct act ctt        246
Thr Ala Gly Leu Ala Tyr Asp Asn Val Asn Gly His Gly Ala Thr Leu
                 60                  65                  70 aca aac aca cat ata ccc agc ttc ggt gac aag ctg acg gca gcc ggc        294
Thr Asn Thr His Ile Pro Ser Phe Gly Asp Lys Leu Thr Ala Ala Gly
             75                  80                  85 aag ttg aac gtg ttc cat aac gac aac cac aac ctg gac gtg aag gcg        342
Lys Leu Asn Val Phe His Asn Asp Asn His Asn Leu Asp Val Lys Ala
         90                  95                 100 ttg gcc acc agg acc atg ccg gat att ccg cgc gtg ccc gac ttc aac        390
Leu Ala Thr Arg Thr Met Pro Asp Ile Pro Arg Val Pro Asp Phe Asn
    105                 110                 115 acc tac ggc ggc ggc gtc gac tac atg ttc aag gac aag gtg ggc gcg        438
Thr Tyr Gly Gly Gly Val Asp Tyr Met Phe Lys Asp Lys Val Gly Ala
120                 125                 130                 135 tcg gcg agc gct gcg cac acg cct ctc ttc gat cgc aac gac tac tcc        486
Ser Ala Ser Ala Ala His Thr Pro Leu Phe Asp Arg Asn Asp Tyr Ser
                140                 145                 150 gtg ggc ggc aag ctg aac ctg ttc cgt gac aag acc acc tcg ctc gac        534
Val Gly Gly Lys Leu Asn Leu Phe Arg Asp Lys Thr Thr Ser Leu Asp
            155                 160                 165 ttc aac gcc gac tac aag aag ttc gag atg ccc aac ttc aag tcc gac        582
Phe Asn Ala Asp Tyr Lys Lys Phe Glu Met Pro Asn Phe Lys Ser Asp
        170                 175                 180 tgg aca ccc aac atc ggc ttc tca ttc agc aag ttt tgg tag                624
Trp Thr Pro Asn Ile Gly Phe Ser Phe Ser Lys Phe Trp *
    185                 190                 195 tttattatta tgattcaagt catccacgtt ttgtacgggt gtaattaatt acgattttaa      684
agtttaagta tttatattta ataaatatt ttggaaatna aaaaaaaaa aaaaaaaaa         744 aaaaaaaaaa ctcgag                                                     760

<210> SEQ ID NO 4
<211> LENGTH: 196
```

```
<212> TYPE: PRT
<213> ORGANISM: Manduca sexta

<400> SEQUENCE: 4

Met Val Val Ser Arg Val Arg Arg Asp Thr His Gly Ser Val Thr Val
1               5                   10                  15

Asn Ser Asp Gly Thr Ser Gly Ala Ile Val Lys Val Pro Phe Ala Gly
            20                  25                  30

Asp Asp Lys Asn Ile Val Ser Ala Ile Gly Gly Leu Asp Leu Asp Lys
        35                  40                  45

Asn Leu Lys Met Ser Gly Ala Thr Ala Gly Leu Ala Tyr Asp Asn Val
    50                  55                  60

Asn Gly His Gly Ala Thr Leu Thr Asn Thr His Ile Pro Ser Phe Gly
65                  70                  75                  80

Asp Lys Leu Thr Ala Ala Gly Lys Leu Asn Val Phe Asn Asp Asn
            85                  90                  95

His Asn Leu Asp Val Lys Ala Leu Ala Thr Arg Thr Met Pro Asp Ile
            100                 105                 110

Pro Arg Val Pro Asp Phe Asn Thr Tyr Gly Gly Val Asp Tyr Met
        115                 120                 125

Phe Lys Asp Lys Val Gly Ala Ser Ala Ser Ala Ala His Thr Pro Leu
130                 135                 140

Phe Asp Arg Asn Asp Tyr Ser Val Gly Gly Lys Leu Asn Leu Phe Arg
145                 150                 155                 160

Asp Lys Thr Thr Ser Leu Asp Phe Asn Ala Asp Tyr Lys Lys Phe Glu
            165                 170                 175

Met Pro Asn Phe Lys Ser Asp Trp Thr Pro Asn Ile Gly Phe Ser Phe
            180                 185                 190

Ser Lys Phe Trp
        195

<210> SEQ ID NO 5
<211> LENGTH: 246
<212> TYPE: DNA
<213> ORGANISM: Manduca sexta
<220> FEATURE:
<221> NAME/KEY: CDS
<222> LOCATION: (1)...(240)
<220> FEATURE:
<221> NAME/KEY: misc_feature
<222> LOCATION: 234, 242, 243, 244, 246
<223> OTHER INFORMATION: n = A,T,C or G

<400> SEQUENCE: 5 atg tcc ctg tcg tgt ctc ttc ctc gtt gcg ctg gcg ctg gtg ggc gca    48
Met Ser Leu Ser Cys Leu Phe Leu Val Ala Leu Ala Leu Val Gly Ala
1               5                   10                  15 gag agc aga tac atc gcc gac gat gtg gtg ttg gta ccg atg atg gta    96
Glu Ser Arg Tyr Ile Ala Asp Asp Val Val Leu Val Pro Met Met Val
            20                  25                  30 tca cgg gta agg cgc gac aca cac ggc tcg gtc acc gtc aac tcg gac   144
Ser Arg Val Arg Arg Asp Thr His Gly Ser Val Thr Val Asn Ser Asp
        35                  40                  45 ggc acc tcc ggg agc gtc gtc aag gtg ccg ttc gca ggc gac gac aag   192
Gly Thr Ser Gly Ser Val Val Lys Val Pro Phe Ala Gly Asp Asp Lys
    50                  55                  60 aac gtc ttt agc gcc atc ggt ggt ctc gac ctc gat aag aan ctc aag   240
Asn Val Phe Ser Ala Ile Gly Gly Leu Asp Leu Asp Lys Xaa Leu Lys
65                  70                  75                  80
```

-continued annngn                                                                246

<210> SEQ ID NO 6
<211> LENGTH: 80
<212> TYPE: PRT
<213> ORGANISM: Manduca sexta
<220> FEATURE:
<221> NAME/KEY: VARIANT
<222> LOCATION: 78
<223> OTHER INFORMATION: Xaa = Any Amino Acid

<400> SEQUENCE: 6

Met Ser Leu Ser Cys Leu Phe Leu Val Ala Leu Ala Leu Val Gly Ala
1               5                   10                  15

Glu Ser Arg Tyr Ile Ala Asp Asp Val Leu Val Pro Met Met Val
            20                  25                  30

Ser Arg Val Arg Arg Asp Thr His Gly Ser Val Thr Val Asn Ser Asp
        35                  40                  45

Gly Thr Ser Gly Ser Val Val Lys Val Pro Phe Ala Gly Asp Asp Lys
    50                  55                  60

Asn Val Phe Ser Ala Ile Gly Gly Leu Asp Leu Asp Lys Xaa Leu Lys
65                  70                  75                  80

<210> SEQ ID NO 7
<211> LENGTH: 336
<212> TYPE: DNA
<213> ORGANISM: Manduca sexta
<220> FEATURE:
<221> NAME/KEY: CDS
<222> LOCATION: (1)...(336)

<400> SEQUENCE: 7 ggc acg agg tcc ctg tcg tgc ctc ttg tta ttt gcg ctg gcg ctg atg      48
Gly Thr Arg Ser Leu Ser Cys Leu Leu Leu Phe Ala Leu Ala Leu Met
1               5                   10                  15 ggc gcg gag agc aga ttc atc gcc gac gat gtg gtg ttc gta cca atg      96
Gly Ala Glu Ser Arg Phe Ile Ala Asp Asp Val Val Phe Val Pro Met
            20                  25                  30 gtg gta tca agg gta cgg cgc gac aca cac ggc tcg gtc acc gtc aac     144
Val Val Ser Arg Val Arg Arg Asp Thr His Gly Ser Val Thr Val Asn
        35                  40                  45 tcg gac ggc acc tcc gga gcg atc gtc aag gtg ccg ttc gca ggc gac     192
Ser Asp Gly Thr Ser Gly Ala Ile Val Lys Val Pro Phe Ala Gly Asp
    50                  55                  60 gac aag aac atc gtc agc gcc atc ggt ggc ctc gac ctc gac aag aac     240
Asp Lys Asn Ile Val Ser Ala Ile Gly Gly Leu Asp Leu Asp Lys Asn
65                  70                  75                  80 ctc aag atg agc ggc gcc aca gcg ggc ttg gct tac gac aac gtc aat     288
Leu Lys Met Ser Gly Ala Thr Ala Gly Leu Ala Tyr Asp Asn Val Asn
                85                  90                  95 gga cac ggc gct act ctt aca aac aca cat ata ccc aag ctt cgg tga     336
Gly His Gly Ala Thr Leu Thr Asn Thr His Ile Pro Lys Leu Arg *
            100                 105                 110

<210> SEQ ID NO 8
<211> LENGTH: 111
<212> TYPE: PRT
<213> ORGANISM: Manduca sexta

<400> SEQUENCE: 8

Gly Thr Arg Ser Leu Ser Cys Leu Leu Leu Phe Ala Leu Ala Leu Met
1               5                   10                  15

-continued

```
Gly Ala Glu Ser Arg Phe Ile Ala Asp Asp Val Val Phe Val Pro Met
            20                  25                  30

Val Val Ser Arg Val Arg Arg Asp Thr His Gly Ser Val Thr Val Asn
        35                  40                  45

Ser Asp Gly Thr Ser Gly Ala Ile Val Lys Val Pro Phe Ala Gly Asp
    50                  55                  60

Asp Lys Asn Ile Val Ser Ala Ile Gly Gly Leu Asp Leu Asp Lys Asn
65                  70                  75                  80

Leu Lys Met Ser Gly Ala Thr Ala Gly Leu Ala Tyr Asp Asn Val Asn
                85                  90                  95

Gly His Gly Ala Thr Leu Thr Asn Thr His Ile Pro Lys Leu Arg
            100                 105                 110
```

<210> SEQ ID NO 9
<211> LENGTH: 444
<212> TYPE: DNA
<213> ORGANISM: Manduca sexta
<220> FEATURE:
<221> NAME/KEY: CDS
<222> LOCATION: (1)...(444)
<220> FEATURE:
<221> NAME/KEY: misc_feature
<222> LOCATION: 123, 339, 421
<223> OTHER INFORMATION: n = A,T,C or G

<400> SEQUENCE: 9

```
atg tcc ctg tcg tgc ctc ttg tta ttt gcg ctg gcg ctg atg ggc gcc      48
Met Ser Leu Ser Cys Leu Leu Leu Phe Ala Leu Ala Leu Met Gly Ala
 1               5                  10                  15 gag agc aga tac atc gct gac gat gtg gtg ttc gta ccg ata gtg gta      96
Glu Ser Arg Tyr Ile Ala Asp Asp Val Val Phe Val Pro Ile Val Val
            20                  25                  30 tca agg gta cgg cgt gac aca cac ggn tcg gtc acc gtc aac tcg gac     144
Ser Arg Val Arg Arg Asp Thr His Gly Ser Val Thr Val Asn Ser Asp
        35                  40                  45 ggc acc tcc gga gcg atc gtc aag gtg ccg ttc gca ggc aac gac aag     192
Gly Thr Ser Gly Ala Ile Val Lys Val Pro Phe Ala Gly Asn Asp Lys
    50                  55                  60 aac atc gtc agc gcc atc ggc ggc ctc gac ctc gac aag aac ttc aag     240
Asn Ile Val Ser Ala Ile Gly Gly Leu Asp Leu Asp Lys Asn Phe Lys
65                  70                  75                  80 atg agc ggc gcc aca gcg ggc ttg gca tac gac aac gtc aat aga cac     288
Met Ser Gly Ala Thr Ala Gly Leu Ala Tyr Asp Asn Val Asn Arg His
                85                  90                  95 ggg gct act ctt aca aac aca cat ata ccc agc ttc ggt gac aag ctg     336
Gly Ala Thr Leu Thr Asn Thr His Ile Pro Ser Phe Gly Asp Lys Leu
            100                 105                 110 acn gca acc ggc aag ttg aac gtg ttc caa aac gac aaa cac aac cct     384
Thr Ala Thr Gly Lys Leu Asn Val Phe Gln Asn Asp Lys His Asn Pro
        115                 120                 125 gga cgt gaa ggg gtt ggg cac caa gga cca tgc caa nta ttc cac gcg     432
Gly Arg Glu Gly Val Gly His Gln Gly Pro Cys Gln Xaa Phe His Ala
    130                 135                 140 tgg ccg act tca                                                     444
Trp Pro Thr Ser
145
```

<210> SEQ ID NO 10
<211> LENGTH: 148
<212> TYPE: PRT
<213> ORGANISM: Manduca sexta
<220> FEATURE:

-continued

```
<221> NAME/KEY: VARIANT
<222> LOCATION: 141
<223> OTHER INFORMATION: Xaa = Any Amino Acid

<400> SEQUENCE: 10

Met Ser Leu Ser Cys Leu Leu Leu Phe Ala Leu Ala Leu Met Gly Ala
 1               5                  10                  15

Glu Ser Arg Tyr Ile Ala Asp Asp Val Val Phe Val Pro Ile Val Val
             20                  25                  30

Ser Arg Val Arg Arg Asp Thr His Gly Ser Val Thr Val Asn Ser Asp
         35                  40                  45

Gly Thr Ser Gly Ala Ile Val Lys Val Pro Phe Ala Gly Asn Asp Lys
     50                  55                  60

Asn Ile Val Ser Ala Ile Gly Gly Leu Asp Leu Asp Lys Asn Phe Lys
 65                  70                  75                  80

Met Ser Gly Ala Thr Ala Gly Leu Ala Tyr Asp Asn Val Asn Arg His
                 85                  90                  95

Gly Ala Thr Leu Thr Asn Thr His Ile Pro Ser Phe Gly Asp Lys Leu
            100                 105                 110

Thr Ala Thr Gly Lys Leu Asn Val Phe Gln Asn Asp Lys His Asn Pro
        115                 120                 125

Gly Arg Glu Gly Val Gly His Gln Gly Pro Cys Gln Xaa Phe His Ala
    130                 135                 140

Trp Pro Thr Ser
145

<210> SEQ ID NO 11
<211> LENGTH: 617
<212> TYPE: DNA
<213> ORGANISM: Manduca sexta
<220> FEATURE:
<221> NAME/KEY: CDS
<222> LOCATION: (28)...(456)

<400> SEQUENCE: 11
gaattcggca cgaggctacg ggctaca atg tct aag ttt ata tcc ata ctt tgt     54
                                Met Ser Lys Phe Ile Ser Ile Leu Cys
                                 1               5 gtt gtc gcc tta ctg cta ata gca gaa act tat tgt tta aca agt ggt     102
Val Val Ala Leu Leu Leu Ile Ala Glu Thr Tyr Cys Leu Thr Ser Gly
 10              15                  20                  25 gtt cgc atc ata caa ccc act tat agg cct cca ccc agg aga cct gtt     150
Val Arg Ile Ile Gln Pro Thr Tyr Arg Pro Pro Pro Arg Arg Pro Val
                 30                  35                  40 att tac aga gct gca cgc gac gct gga gat gaa ccc ttg tgg ctg tac     198
Ile Tyr Arg Ala Ala Arg Asp Ala Gly Asp Glu Pro Leu Trp Leu Tyr
             45                  50                  55 caa gga gac gac cac cct cga gcc cct tca agc ggc gac cat cct gta     246
Gln Gly Asp Asp His Pro Arg Ala Pro Ser Ser Gly Asp His Pro Val
         60                  65                  70 ctg ccc tcg atc ata gac gat gtg aag ctg gac ccc aac agg cgg tat     294
Leu Pro Ser Ile Ile Asp Asp Val Lys Leu Asp Pro Asn Arg Arg Tyr
     75                  80                  85 gcg cgt agt gta agc gag cct tcg tca cag gag cat cat gac cgc ttt     342
Ala Arg Ser Val Ser Glu Pro Ser Ser Gln Glu His His Asp Arg Phe
 90                  95                 100                 105 gcg agg agc ttc gac tcc cgc agc agc aag cat cac ggc ggt agt cac     390
Ala Arg Ser Phe Asp Ser Arg Ser Ser Lys His His Gly Gly Ser His
                110                 115                 120
```

```
tcc acg tcc ggc ggc agc cgc gac act gga gct act cac ccg gga tac        438
Ser Thr Ser Gly Gly Ser Arg Asp Thr Gly Ala Thr His Pro Gly Tyr
            125                 130                 135 aat cgt cgt aac tca taa tttctcttca gtttctaaat attttttgttt               486
Asn Arg Arg Asn Ser *
            140 ctgctactaa ttttttctca tcaatattct tgtttgcttt caaatctttc attttatgat       546 aataatatgt atactgatca ttatattgaa ataaatgatt aaattgaaaa aaaaaaaaa        606 aaaaactcga g                                                           617

<210> SEQ ID NO 12
<211> LENGTH: 142
<212> TYPE: PRT
<213> ORGANISM: Manduca sexta

<400> SEQUENCE: 12

Met Ser Lys Phe Ile Ser Ile Leu Cys Val Val Ala Leu Leu Leu Ile
1               5                   10                  15

Ala Glu Thr Tyr Cys Leu Thr Ser Gly Val Arg Ile Ile Gln Pro Thr
            20                  25                  30

Tyr Arg Pro Pro Pro Arg Arg Pro Val Ile Tyr Arg Ala Ala Arg Asp
        35                  40                  45

Ala Gly Asp Glu Pro Leu Trp Leu Tyr Gln Gly Asp Asp His Pro Arg
    50                  55                  60

Ala Pro Ser Ser Gly Asp His Pro Val Leu Pro Ser Ile Ile Asp Asp
65                  70                  75                  80

Val Lys Leu Asp Pro Asn Arg Arg Tyr Ala Arg Ser Val Ser Glu Pro
                85                  90                  95

Ser Ser Gln Glu His His Asp Arg Phe Ala Arg Ser Phe Asp Ser Arg
            100                 105                 110

Ser Ser Lys His His Gly Gly Ser His Ser Thr Ser Gly Gly Ser Arg
        115                 120                 125

Asp Thr Gly Ala Thr His Pro Gly Tyr Asn Arg Arg Asn Ser
    130                 135                 140

<210> SEQ ID NO 13
<211> LENGTH: 370
<212> TYPE: DNA
<213> ORGANISM: Manduca sexta
<220> FEATURE:
<221> NAME/KEY: CDS
<222> LOCATION: (1)...(216)

<400> SEQUENCE: 13 cta tac tgt ctt ttg ttt ttg tgt ttc att act ttc tcc atg agt gaa        48
Leu Tyr Cys Leu Leu Phe Leu Cys Phe Ile Thr Phe Ser Met Ser Glu
1               5                   10                  15 gat ccg aga tgt tct cag ccg att gca tct ggt gtg tgc ttt gga aat        96
Asp Pro Arg Cys Ser Gln Pro Ile Ala Ser Gly Val Cys Phe Gly Asn
            20                  25                  30 att gaa aaa ttc gga tac gac atc gac gag cac aaa tgt gta cag ttc        144
Ile Glu Lys Phe Gly Tyr Asp Ile Asp Glu His Lys Cys Val Gln Phe
        35                  40                  45 gtg tac gga gga tgc ttt ggc aat gac aac caa ttc gac tcg ctt gaa        192
Val Tyr Gly Gly Cys Phe Gly Asn Asp Asn Gln Phe Asp Ser Leu Glu
    50                  55                  60 gaa tgt caa gca gtt tgt cct taa ccattccgat gtttataaat gacgtgtata       246
Glu Cys Gln Ala Val Cys Pro *
65                  70
```

```
taatgcaaga atgcattata gccaatcaat cgatttttaa tcgattcaga agccgttatc    306
gattatgaca ttgctgtgca attttctaaa tatttaattt agtgttattc atattcactt    366
tcaa                                                                  370

<210> SEQ ID NO 14
<211> LENGTH: 71
<212> TYPE: PRT
<213> ORGANISM: Manduca sexta

<400> SEQUENCE: 14

Leu Tyr Cys Leu Leu Phe Leu Cys Phe Ile Thr Phe Ser Met Ser Glu
 1               5                  10                  15

Asp Pro Arg Cys Ser Gln Pro Ile Ala Ser Gly Val Cys Phe Gly Asn
            20                  25                  30

Ile Glu Lys Phe Gly Tyr Asp Ile Asp Glu His Lys Cys Val Gln Phe
        35                  40                  45

Val Tyr Gly Gly Cys Phe Gly Asn Asp Asn Gln Phe Asp Ser Leu Glu
    50                  55                  60

Glu Cys Gln Ala Val Cys Pro
65                  70

<210> SEQ ID NO 15
<211> LENGTH: 948
<212> TYPE: DNA
<213> ORGANISM: Manduca sexta
<220> FEATURE:
<221> NAME/KEY: CDS
<222> LOCATION: (23)...(208)

<400> SEQUENCE: 15
gaattcggca cgagggttga ca atg aaa agc caa ttg caa atc gta ttg ttg      52
                        Met Lys Ser Gln Leu Gln Ile Val Leu Leu
                         1               5                  10 ttg ctg acg gtg atg ttt gca ata act tat gcc ggt tac tac aca aca      100
Leu Leu Thr Val Met Phe Ala Ile Thr Tyr Ala Gly Tyr Tyr Thr Thr
                15                  20                  25 aca caa cgt cat ttt gca gta agc tgc agt caa gct tgt gaa tca gaa      148
Thr Gln Arg His Phe Ala Val Ser Cys Ser Gln Ala Cys Glu Ser Glu
            30                  35                  40 gga agc aac tgt gaa ttg gtt aga agc tat gta tgg act tgc tat tgt      196
Gly Ser Asn Cys Glu Leu Val Arg Ser Tyr Val Trp Thr Cys Tyr Cys
        45                  50                  55 tat tgt cca tga ttttggctat gtttccaaga acatagtttt attatatggt          248
Tyr Cys Pro *
    60 gtaacacgaa aggaaaataa ttattttact gaagaatatt tttacaagaa agaaataaga    308 gacaagaaag aaaaaaaaac aagacagtta tattttgtaa aaggggacc tcgtgcatca     368 gaaaggaaat gtagttaatc atttaaagga ctgtatatgt tttaaatttt tctcacgaaa    428 tgaatctgaa gtgattttc tgacgactac gaaaattgtc gcggacataa tatatatttc     488 tgacaaatcc taatttgcac aggaatattt gaaagtggta tttaagctta tgcactgcgc    548 agtgtccttg tatataatca ttttactatt caagttgaat gaaacaattg aaatttgcat    608 caaattgtgc tttgtaaatc tcttatggtc acatcttacg gctgcatcat gtgtcaaccg    668 agagatattt tatcgtaata ttaagttcta cgctggtggt tatgtttta ttgtttagtg     728 tcatttacca agtacatctc taaatttcta gtttcagttt agattttaa gcggaatatt     788
```

```
ttaatctgta ataactacat atccttgaag gagtaggcag aggcgcaacg ctgcattccc    848
ttttcgccgt gtgtattaca tcccatgata tgatgagggg cgagcctatc gccgtatcgg    908
ggataaattc ccgattccgg gctgatactg agaagaaaaa                          948
```

<210> SEQ ID NO 16
<211> LENGTH: 61
<212> TYPE: PRT
<213> ORGANISM: Manduca sexta

<400> SEQUENCE: 16

```
Met Lys Ser Gln Leu Gln Ile Val Leu Leu Leu Thr Val Met Phe
 1               5                  10                  15

Ala Ile Thr Tyr Ala Gly Tyr Tyr Thr Thr Thr Gln Arg His Phe Ala
            20                  25                  30

Val Ser Cys Ser Gln Ala Cys Glu Ser Glu Gly Ser Asn Cys Glu Leu
        35                  40                  45

Val Arg Ser Tyr Val Trp Thr Cys Tyr Cys Tyr Cys Pro
    50                  55                  60
```

<210> SEQ ID NO 17
<211> LENGTH: 254
<212> TYPE: PRT
<213> ORGANISM: Trichoplusia ni

<400> SEQUENCE: 17

```
Met Phe Thr Tyr Lys Leu Ile Leu Gly Leu Val Leu Val Ser Ala
 1               5                  10                  15

Ser Ala Arg Tyr Leu Val Phe Glu Asp Leu Glu Gly Glu Ser Tyr Leu
            20                  25                  30

Val Pro Asn Gln Ala Glu Asp Glu Gln Val Leu Glu Gly Glu Pro Phe
        35                  40                  45

Tyr Glu Asn Ala Val Gln Leu Ala Ser Pro Arg Val Arg Arg Gln Ala
    50                  55                  60

Gln Gly Ser Val Thr Leu Asn Ser Asp Gly Ser Met Gly Leu Gly Ala
65                  70                  75                  80

Lys Val Pro Ile Val Gly Asn Glu Lys Asn Val Leu Ser Ala Leu Gly
            85                  90                  95

Ser Val Asp Leu Asn Asp Gln Leu Lys Pro Ala Ser Arg Gly Met Gly
        100                 105                 110

Leu Ala Leu Asp Asn Val Asn Gly His Gly Leu Ser Val Met Lys Glu
    115                 120                 125

Thr Val Pro Gly Phe Gly Asp Arg Leu Thr Gly Ala Gly Arg Val Asn
    130                 135                 140

Val Phe His Asn Asp Asn His Asp Ile Ser Ala Lys Ala Phe Val Thr
145                 150                 155                 160

Lys Asn Met Pro Asp Phe Pro Asn Val Pro Asn Phe Asn Thr Val Gly
            165                 170                 175

Gly Gly Val Asp Tyr Met Tyr Lys Asn Lys Val Gly Ala Ser Leu Gly
        180                 185                 190

Met Ala Asn Thr Pro Phe Leu Asp Arg Lys Asp Tyr Ser Ala Met Gly
    195                 200                 205

Asn Leu Asn Val Phe Arg Ser Pro Thr Thr Ser Val Asp Phe Asn Ala
        210                 215                 220

Gly Phe Lys Lys Phe Asp Thr Pro Val Phe Lys Ser Asn Trp Glu Pro
225                 230                 235                 240
```

```
Asn Phe Gly Leu Thr Phe Ser Arg Ser Phe Gly Asn Lys Trp
                245                 250

<210> SEQ ID NO 18
<211> LENGTH: 233
<212> TYPE: PRT
<213> ORGANISM: Hyalophora cecropia

<400> SEQUENCE: 18

Met Phe Ala Lys Leu Phe Leu Val Ser Val Leu Leu Val Gly Val Asn
1               5                   10                  15

Ser Arg Tyr Val Leu Val Glu Glu Pro Gly Tyr Tyr Asp Lys Gln Tyr
            20                  25                  30

Glu Glu Gln Pro Gln Gln Trp Val Asn Ser Arg Val Arg Arg Gln Ala
        35                  40                  45

Gly Ala Leu Thr Ile Asn Ser Asp Gly Thr Ser Gly Ala Val Val Lys
    50                  55                  60

Val Pro Ile Thr Gly Asn Glu Asn His Lys Phe Ser Ala Leu Gly Ser
65                  70                  75                  80

Val Asp Leu Thr Asn Gln Met Lys Leu Gly Ala Ala Thr Ala Gly Leu
                85                  90                  95

Ala Tyr Asp Asn Val Asn Gly His Gly Ala Thr Leu Thr Lys Thr His
            100                 105                 110

Ile Pro Gly Phe Gly Asp Lys Met Thr Ala Ala Gly Lys Val Asn Leu
        115                 120                 125

Phe His Asn Asp Asn His Asp Phe Ser Ala Lys Ala Phe Ala Thr Lys
    130                 135                 140

Asn Met Pro Asn Ile Pro Gln Val Pro Asn Phe Asn Thr Val Gly Ala
145                 150                 155                 160

Gly Val Asp Tyr Met Phe Lys Asp Lys Ile Gly Ala Ser Ala Asn Ala
                165                 170                 175

Ala His Thr Asp Phe Ile Asn Arg Asn Asp Tyr Ser Leu Gly Gly Lys
            180                 185                 190

Leu Asn Leu Phe Lys Thr Pro Thr Thr Ser Leu Asp Phe Asn Ala Gly
        195                 200                 205

Trp Lys Lys Phe Asp Thr Pro Phe Lys Ser Ser Trp Glu Pro Ser
    210                 215                 220

Thr Ser Phe Ser Phe Ser Lys Tyr Phe
225                 230

<210> SEQ ID NO 19
<211> LENGTH: 235
<212> TYPE: PRT
<213> ORGANISM: Hyalophora cecropia

<400> SEQUENCE: 19

Met Phe Gly Lys Ile Val Phe Leu Leu Val Ala Leu Cys Ala Gly
1               5                   10                  15

Val Gln Ser Arg Tyr Leu Ile Val Ser Glu Pro Val Tyr Tyr Ile Glu
            20                  25                  30

His Tyr Glu Glu Pro Glu Leu Leu Ala Ser Ser Arg Val Arg Arg Asp
        35                  40                  45

Ala His Gly Ala Leu Thr Leu Asn Ser Asp Gly Thr Ser Gly Ala Val
    50                  55                  60

Val Lys Val Pro Phe Ala Gly Asn Asp Lys Asn Ile Val Ser Ala Ile
65                  70                  75                  80
```

-continued

```
Gly Ser Val Asp Leu Thr Asp Arg Gln Lys Leu Gly Ala Ala Thr Ala
                85                  90                  95

Gly Val Ala Leu Asp Asn Ile Asn Gly His Gly Leu Ser Leu Thr Asp
            100                 105                 110

Thr His Ile Pro Gly Phe Gly Asp Lys Met Thr Ala Ala Gly Lys Val
        115                 120                 125

Asn Val Phe His Asn Asp Asn His Asp Ile Thr Ala Lys Ala Phe Ala
130                 135                 140

Thr Arg Asn Met Pro Asp Ile Ala Asn Val Pro Asn Phe Asn Thr Val
145                 150                 155                 160

Gly Gly Gly Ile Asp Tyr Met Phe Lys Asp Lys Ile Gly Ala Ser Ala
                165                 170                 175

Ser Ala Ala His Thr Asp Phe Ile Asn Arg Asn Asp Tyr Ser Leu Asp
            180                 185                 190

Gly Lys Leu Asn Leu Phe Lys Thr Pro Asp Thr Ser Ile Asp Phe Asn
        195                 200                 205

Ala Gly Phe Lys Lys Phe Asp Thr Pro Phe Met Lys Ser Ser Trp Glu
210                 215                 220

Pro Asn Phe Gly Phe Ser Leu Ser Lys Tyr Phe
225                 230                 235

<210> SEQ ID NO 20
<211> LENGTH: 214
<212> TYPE: PRT
<213> ORGANISM: Bombyx mori

<400> SEQUENCE: 20

Met Ser Lys Ser Val Ala Leu Leu Leu Cys Ala Cys Leu Ala Ser
  1               5                  10                  15

Gly Arg His Val Pro Thr Arg Ala Arg Arg Gln Ala Gly Ser Phe Thr
                 20                  25                  30

Val Asn Ser Asp Gly Thr Ser Gly Ala Ala Leu Lys Val Pro Leu Thr
             35                  40                  45

Gly Asn Asp Lys Asn Val Leu Ser Ala Ile Gly Ser Ala Asp Phe Asn
         50                  55                  60

Asp Arg His Lys Leu Ser Ala Ala Ser Ala Gly Leu Ala Leu Asp Asn
65                  70                  75                  80

Val Asn Gly His Gly Leu Ser Leu Thr Gly Thr Arg Ile Pro Gly Phe
                 85                  90                  95

Gly Glu Gln Leu Gly Val Ala Gly Lys Val Asn Leu Phe His Asn Asn
            100                 105                 110

Asn His Asp Leu Ser Ala Lys Ala Phe Ala Ile Arg Asn Ser Pro Ser
        115                 120                 125

Ala Ile Pro Asn Ala Pro Asn Phe Asn Thr Leu Gly Gly Gly Val Asp
130                 135                 140

Tyr Met Phe Lys Gln Lys Val Gly Ala Ser Leu Ser Ala Ala His Ser
145                 150                 155                 160

Asp Val Ile Asn Arg Asn Asp Tyr Ser Ala Gly Gly Lys Leu Asn Leu
                165                 170                 175

Phe Arg Ser Pro Ser Ser Leu Asp Phe Asn Ala Gly Phe Lys Lys
            180                 185                 190

Phe Asp Thr Pro Phe Tyr Arg Ser Ser Trp Glu Pro Asn Val Gly Phe
        195                 200                 205

Ser Phe Ser Lys Phe Phe
210
```

```
<210> SEQ ID NO 21
<211> LENGTH: 326
<212> TYPE: DNA
<213> ORGANISM: Manduca sexta
<220> FEATURE:
<221> NAME/KEY: CDS
<222> LOCATION: (1)...(177)

<400> SEQUENCE: 21 atg agt gaa gat ccg aga tgt tct cag ccg att gca tct ggt gtg tgc      48
Met Ser Glu Asp Pro Arg Cys Ser Gln Pro Ile Ala Ser Gly Val Cys
 1               5                  10                  15 ttt gga aat att gaa aaa ttc gga tac gac atc gac gag cac aaa tgt      96
Phe Gly Asn Ile Glu Lys Phe Gly Tyr Asp Ile Asp Glu His Lys Cys
                 20                  25                  30 gta cag ttc gtg tac gga gga tgc ttt ggc aat gat aac caa ttc gac     144
Val Gln Phe Val Tyr Gly Gly Cys Phe Gly Asn Asp Asn Gln Phe Asp
             35                  40                  45 tcg ctt gaa gaa tgt caa gca gtt tgt cct taa ccattccaat gtttataaat   197
Ser Leu Glu Glu Cys Gln Ala Val Cys Pro *
         50                  55 gacgtgtata taatacacac aataatcaat cgatttttaa tcgattcaga agccgttatc   257
tattactaaa ttgctgtgca attttataaa tatttaattt agtgttatta atattcactt   317
tcaaaaata                                                            326

<210> SEQ ID NO 22
<211> LENGTH: 58
<212> TYPE: PRT
<213> ORGANISM: Manduca sexta

<400> SEQUENCE: 22

Met Ser Glu Asp Pro Arg Cys Ser Gln Pro Ile Ala Ser Gly Val Cys
 1               5                  10                  15

Phe Gly Asn Ile Glu Lys Phe Gly Tyr Asp Ile Asp Glu His Lys Cys
                 20                  25                  30

Val Gln Phe Val Tyr Gly Gly Cys Phe Gly Asn Asp Asn Gln Phe Asp
             35                  40                  45

Ser Leu Glu Glu Cys Gln Ala Val Cys Pro
         50                  55

<210> SEQ ID NO 23
<211> LENGTH: 58
<212> TYPE: PRT
<213> ORGANISM: Manduca sexta

<400> SEQUENCE: 23

Met Ser Glu Asp Pro Arg Cys Ser Gln Pro Ile Ala Ser Gly Val Cys
 1               5                  10                  15

Phe Gly Asn Ile Glu Lys Phe Gly Tyr Asp Ile Asp Glu His Lys Cys
                 20                  25                  30

Val Gln Phe Val Tyr Gly Gly Cys Phe Gly Asn Asp Asn Gln Phe Asp
             35                  40                  45

Ser Leu Glu Glu Cys Gln Ala Val Cys Pro
         50                  55

<210> SEQ ID NO 24
<211> LENGTH: 365
<212> TYPE: DNA
<213> ORGANISM: Heliothis virescens
```

```
<220> FEATURE:
<221> NAME/KEY: CDS
<222> LOCATION: (1)...(192)

<400> SEQUENCE: 24 atg aat ttc tcg cgg ata ttt ttc ttc gtg ttc gcg tgt ttg gta gca        48
Met Asn Phe Ser Arg Ile Phe Phe Phe Val Phe Ala Cys Leu Val Ala
 1               5                  10                  15 gtg tgc agc gtg tcg gcg gcg cct gag ccg agg tgg aag gtc ttc aag        96
Val Cys Ser Val Ser Ala Ala Pro Glu Pro Arg Trp Lys Val Phe Lys
                 20                  25                  30 aaa att gag aag atg ggt cgc aac ata agg gac ggt gtc atc aaa gct       144
Lys Ile Glu Lys Met Gly Arg Asn Ile Arg Asp Gly Val Ile Lys Ala
         35                  40                  45 gcg cca gct atc gaa gtc ctg ggc cag gct aaa gct ctt gga aaa tag       192
Ala Pro Ala Ile Glu Val Leu Gly Gln Ala Lys Ala Leu Gly Lys  *
     50                  55                  60 atcttaacta ttaaggaata acgttcaaag tattataagt gttcattacc tcgaatatca     252
aagaatatct tatgtatttt ttttttttgt aaatatttt gcgtttattt tatgtaatac      312
tcagagtgca tgcaattaaa ttgttttaaa gcgttaaaaa aaaaaaaaaa aaa            365

<210> SEQ ID NO 25
<211> LENGTH: 63
<212> TYPE: PRT
<213> ORGANISM: Heliothis virescens

<400> SEQUENCE: 25

Met Asn Phe Ser Arg Ile Phe Phe Phe Val Phe Ala Cys Leu Val Ala
 1               5                  10                  15

Val Cys Ser Val Ser Ala Ala Pro Glu Pro Arg Trp Lys Val Phe Lys
                 20                  25                  30

Lys Ile Glu Lys Met Gly Arg Asn Ile Arg Asp Gly Val Ile Lys Ala
         35                  40                  45

Ala Pro Ala Ile Glu Val Leu Gly Gln Ala Lys Ala Leu Gly Lys
     50                  55                  60

<210> SEQ ID NO 26
<211> LENGTH: 63
<212> TYPE: PRT
<213> ORGANISM: Heliothis virescens

<400> SEQUENCE: 26

Met Asn Phe Ser Arg Ile Phe Phe Phe Val Phe Ala Cys Leu Val Ala
 1               5                  10                  15

Val Cys Ser Val Ser Ala Ala Pro Glu Pro Arg Trp Lys Val Phe Lys
                 20                  25                  30

Lys Ile Glu Lys Met Gly Arg Asn Ile Arg Asp Gly Val Ile Lys Ala
         35                  40                  45

Ala Pro Ala Ile Glu Val Leu Gly Gln Ala Lys Ala Leu Gly Lys
     50                  55                  60

<210> SEQ ID NO 27
<211> LENGTH: 600
<212> TYPE: DNA
<213> ORGANISM: Manduca sexta
<220> FEATURE:
<221> NAME/KEY: CDS
<222> LOCATION: (36)...(464)

<400> SEQUENCE: 27
```

```
actagtggat cccccgggct gcaggacggg ctaca atg tct aag ttt ata tcc           53
                                        Met Ser Lys Phe Ile Ser
                                        1               5 ata ctt tgt gtt gtc gcc tta ctg cta ata gca gaa act tat tgt tta        101
Ile Leu Cys Val Val Ala Leu Leu Leu Ile Ala Glu Thr Tyr Cys Leu
            10                  15                  20 aca agt ggt gtt cgc atc ata caa ccc act tat agg cct cca ccc agg        149
Thr Ser Gly Val Arg Ile Ile Gln Pro Thr Tyr Arg Pro Pro Pro Arg
        25                  30                  35 aga cct gtt att tac aga gct gca cgc gac gct gga gat gaa ccc ttg        197
Arg Pro Val Ile Tyr Arg Ala Ala Arg Asp Ala Gly Asp Glu Pro Leu
    40                  45                  50 tgg ctg tac caa gga gac gac cac cct cga gcc cct tca agc ggc gac        245
Trp Leu Tyr Gln Gly Asp Asp His Pro Arg Ala Pro Ser Ser Gly Asp
55                  60                  65                  70 cat cct gta ctg ccc tcg atc ata gac gat gtg aag ctg gac ccc aac        293
His Pro Val Leu Pro Ser Ile Ile Asp Asp Val Lys Leu Asp Pro Asn
                75                  80                  85 agg cgg tat gcg cgt agt gta agc gag cct tcg tca cag gag cat cat        341
Arg Arg Tyr Ala Arg Ser Val Ser Glu Pro Ser Ser Gln Glu His His
            90                  95                 100 gac cgc ttt gcg agg agc ttc gac tcc cgc agc agc aag cat cac ggc        389
Asp Arg Phe Ala Arg Ser Phe Asp Ser Arg Ser Ser Lys His His Gly
        105                 110                 115 ggc agt cac tcc acg tcc ggc ggc agc cgc gac act gga gct act cac        437
Gly Ser His Ser Thr Ser Gly Gly Ser Arg Asp Thr Gly Ala Thr His
    120                 125                 130 tcg gga tac aat cgt cgt aac tca taa tttctcttca gtttctaaat              484
Ser Gly Tyr Asn Arg Arg Asn Ser  *
135                 140 attttttgttt ctgctactaa tttttttctca tcaatattct tgtttgcttt caaatctttc    544
attttatgat aataatatgt atactgatca ttatattgaa ataaatgatt aaattg          600
```

<210> SEQ ID NO 28
<211> LENGTH: 142
<212> TYPE: PRT
<213> ORGANISM: Manduca sexta

<400> SEQUENCE: 28

```
Met Ser Lys Phe Ile Ser Ile Leu Cys Val Val Ala Leu Leu Leu Ile
1               5                   10                  15

Ala Glu Thr Tyr Cys Leu Thr Ser Gly Val Arg Ile Ile Gln Pro Thr
            20                  25                  30

Tyr Arg Pro Pro Pro Arg Arg Pro Val Ile Tyr Arg Ala Ala Arg Asp
        35                  40                  45

Ala Gly Asp Glu Pro Leu Trp Leu Tyr Gln Gly Asp Asp His Pro Arg
    50                  55                  60

Ala Pro Ser Ser Gly Asp His Pro Val Leu Pro Ser Ile Ile Asp Asp
65                  70                  75                  80

Val Lys Leu Asp Pro Asn Arg Arg Tyr Ala Arg Ser Val Ser Glu Pro
                85                  90                  95

Ser Ser Gln Glu His His Asp Arg Phe Ala Arg Ser Phe Asp Ser Arg
            100                 105                 110

Ser Ser Lys His His Gly Gly Ser His Ser Thr Ser Gly Gly Ser Arg
        115                 120                 125

Asp Thr Gly Ala Thr His Ser Gly Tyr Asn Arg Arg Asn Ser
    130                 135                 140
```

```
<210> SEQ ID NO 29
<211> LENGTH: 142
<212> TYPE: PRT
<213> ORGANISM: Manduca sexta

<400> SEQUENCE: 29

Met Ser Lys Phe Ile Ser Ile Leu Cys Val Ala Leu Leu Leu Ile
 1               5                  10                  15

Ala Glu Thr Tyr Cys Leu Thr Ser Gly Val Arg Ile Ile Gln Pro Thr
             20                  25                  30

Tyr Arg Pro Pro Arg Arg Pro Val Ile Tyr Arg Ala Ala Arg Asp
         35                  40                  45

Ala Gly Asp Glu Pro Leu Trp Leu Tyr Gln Gly Asp His Pro Arg
 50                  55                  60

Ala Pro Ser Ser Gly Asp His Pro Val Leu Pro Ser Ile Ile Asp Asp
 65                  70                  75                  80

Val Lys Leu Asp Pro Asn Arg Arg Tyr Ala Arg Ser Val Ser Glu Pro
                 85                  90                  95

Ser Ser Gln Glu His His Asp Arg Phe Ala Arg Ser Phe Asp Ser Arg
                100                 105                 110

Ser Ser Lys His His Gly Gly Ser His Ser Thr Ser Gly Gly Ser Arg
            115                 120                 125

Asp Thr Gly Ala Thr His Ser Gly Tyr Asn Arg Arg Asn Ser
        130                 135                 140

<210> SEQ ID NO 30
<211> LENGTH: 360
<212> TYPE: DNA
<213> ORGANISM: Ostrinia nubilalis
<220> FEATURE:
<221> NAME/KEY: CDS
<222> LOCATION: (1)...(201)

<400> SEQUENCE: 30 atg aac ttc tcc aaa att ttg ttc gct gtg ttc gct atc ttc atg gct      48
Met Asn Phe Ser Lys Ile Leu Phe Ala Val Phe Ala Ile Phe Met Ala
 1               5                  10                  15 ttt gcc gcg gta tcc gct gca ccc aac cct aga tgg aat cct ttt aag      96
Phe Ala Ala Val Ser Ala Ala Pro Asn Pro Arg Trp Asn Pro Phe Lys
             20                  25                  30 aaa ctg gag cgt gtg ggc cag aac atc cgt gac ggg atc atc aaa gca     144
Lys Leu Glu Arg Val Gly Gln Asn Ile Arg Asp Gly Ile Ile Lys Ala
         35                  40                  45 gct cca gca gtt gca gtg gtg ggc caa gct gcc acc ata tac aag ggc     192
Ala Pro Ala Val Ala Val Val Gly Gln Ala Ala Thr Ile Tyr Lys Gly
     50                  55                  60 ggg aaa taa ataactacat catcatcatc gtcatcatca tcatcatctg             241
Gly Lys *
 65 tgacgccaaa agatgcttat atatgctgct ggggatatga cttcatgtgg acaagcatct   301 ttactaactt tttgtatata attttgtacc aaaaatggta tggtaaagtt atgaaacgt    360

<210> SEQ ID NO 31
<211> LENGTH: 66
<212> TYPE: PRT
<213> ORGANISM: Ostrinia nubilalis

<400> SEQUENCE: 31

Met Asn Phe Ser Lys Ile Leu Phe Ala Val Phe Ala Ile Phe Met Ala
```

```
                1               5                   10                  15
Phe Ala Ala Val Ser Ala Ala Pro Asn Pro Arg Trp Asn Pro Phe Lys
                    20                  25                  30

Lys Leu Glu Arg Val Gly Gln Asn Ile Arg Asp Gly Ile Ile Lys Ala
            35                  40                  45

Ala Pro Ala Val Ala Val Val Gly Gln Ala Ala Thr Ile Tyr Lys Gly
        50                  55                  60

Gly Lys
65

<210> SEQ ID NO 32
<211> LENGTH: 66
<212> TYPE: PRT
<213> ORGANISM: Ostrinia nubilalis

<400> SEQUENCE: 32

Met Asn Phe Ser Lys Ile Leu Phe Ala Val Phe Ala Ile Phe Met Ala
  1               5                   10                  15

Phe Ala Ala Val Ser Ala Ala Pro Asn Pro Arg Trp Asn Pro Phe Lys
                    20                  25                  30

Lys Leu Glu Arg Val Gly Gln Asn Ile Arg Asp Gly Ile Ile Lys Ala
            35                  40                  45

Ala Pro Ala Val Ala Val Val Gly Gln Ala Ala Thr Ile Tyr Lys Gly
        50                  55                  60

Gly Lys
65

<210> SEQ ID NO 33
<211> LENGTH: 407
<212> TYPE: DNA
<213> ORGANISM: Ostrinia nubilalis
<220> FEATURE:
<221> NAME/KEY: CDS
<222> LOCATION: (3)...(281)
<220> FEATURE:
<221> NAME/KEY: misc_feature
<222> LOCATION: 378

```
ccggct                                                      407
```

```
<210> SEQ ID NO 34
<211> LENGTH: 90
<212> TYPE: PRT
<213> ORGANISM: Ostrinia nubilalis

<400> SEQUENCE: 34

Val Val Leu Cys Ser Leu Ala Ala Val Leu Leu Ala Phe Val Ala Glu
1               5                   10                  15

Ser Ser Ala Gln Arg Phe Ile Gln Pro Thr Tyr Arg Pro Pro Pro Gln
            20                  25                  30

Arg Pro Lys Ile Tyr Arg Leu Arg Arg Asp Ala Gly Glu Pro Leu
        35                  40                  45

Trp Leu Tyr Gln Gly Asp Asp Val Gln Arg Ala Pro Ala Thr Gly Asp
    50                  55                  60

His Pro Tyr Leu Pro Pro Asn Ile Asp Asp Ile His Leu Asp Pro Asn
65                  70                  75                  80

Thr Lys Ile Arg Ser Gln Arg Arg Leu Ser
                85                  90

<210> SEQ ID NO 35
<211> LENGTH: 92
<212> TYPE: PRT
<213> ORGANISM: Ostrinia nubilalis

<400> SEQUENCE: 35

His Gln Val Val Leu Cys Ser Leu Ala Ala Val Leu Leu Ala Phe Val
1               5                   10                  15

Ala Glu Ser Ser Ala Gln Arg Phe Ile Gln Pro Thr Tyr Arg Pro Pro
            20                  25                  30

Pro Gln Arg Pro Pro Lys Ile Tyr Arg Leu Arg Arg Asp Ala Gly Glu
        35                  40                  45

Pro Leu Trp Leu Tyr Gln Gly Asp Asp Val Gln Arg Ala Pro Ala Thr
    50                  55                  60

Gly Asp His Pro Tyr Leu Pro Pro Asn Ile Asp Asp Ile His Leu Asp
65                  70                  75                  80

Pro Asn Thr Lys Ile Arg Ser Gln Arg Arg Leu Ser
                85                  90

<210> SEQ ID NO 36
<211> LENGTH: 362
<212> TYPE: DNA
<213> ORGANISM: Ostrinia nubilalis
<220> FEATURE:
<221> NAME/KEY: CDS
<222> LOCATION: (1)...(252)

<400> SEQUENCE: 36 atg ttc aaa tta agt ttt att att ttc atg ttg gtg gcc att gcg agc    48
Met Phe Lys Leu Ser Phe Ile Ile Phe Met Leu Val Ala Ile Ala Ser
1               5                   10                  15 gtt tta agc agt gaa gcc cca gcc cca gac tgc acc tcg cct ctt gag    96
Val Leu Ser Ser Glu Ala Pro Ala Pro Asp Cys Thr Ser Pro Leu Glu
            20                  25                  30 acc gga cca tgc aga ggc agg aaa gtt gct ttc ggc tac gat act gac   144
Thr Gly Pro Cys Arg Gly Arg Lys Val Ala Phe Gly Tyr Asp Thr Asp
        35                  40                  45 ttg gaa gga tgc aaa cag ttc atc tac gga gga tgt gac ggc aac ggc   192
```

```
Leu Glu Gly Cys Lys Gln Phe Ile Tyr Gly Gly Cys Asp Gly Asn Gly
    50                  55                  60 aac cgt tac aac act cta gag gag tgt cag gct gct tgc gag agt gac    240
Asn Arg Tyr Asn Thr Leu Glu Glu Cys Gln Ala Ala Cys Glu Ser Asp
65                  70                  75                  80 tgc aac aaa taa taacgaaatg caagcaatca attgggtatt tgacagcaca        292
Cys Asn Lys  * gtcaattgac atactttttt taaactgtca aaacgcaaca ttccctattt ttcacatttt   352
gcaaagtaga                                                          362

<210> SEQ ID NO 37
<211> LENGTH: 83
<212> TYPE: PRT
<213> ORGANISM: Ostrinia nubilalis

<400> SEQUENCE: 37

Met Phe Lys Leu Ser Phe Ile Ile Phe Met Leu Val Ala Ile Ala Ser
1               5                   10                  15

Val Leu Ser Ser Glu Ala Pro Ala Pro Asp Cys Thr Ser Pro Leu Glu
                20                  25                  30

Thr Gly Pro Cys Arg Gly Arg Lys Val Ala Phe Gly Tyr Asp Thr Asp
            35                  40                  45

Leu Glu Gly Cys Lys Gln Phe Ile Tyr Gly Gly Cys Asp Gly Asn Gly
    50                  55                  60

Asn Arg Tyr Asn Thr Leu Glu Glu Cys Gln Ala Ala Cys Glu Ser Asp
65                  70                  75                  80

Cys Asn Lys

<210> SEQ ID NO 38
<211> LENGTH: 83
<212> TYPE: PRT
<213> ORGANISM: Ostrinia nubilalis

<400> SEQUENCE: 38

Met Phe Lys Leu Ser Phe Ile Ile Phe Met Leu Val Ala Ile Ala Ser
1               5                   10                  15

Val Leu Ser Ser Glu Ala Pro Ala Pro Asp Cys Thr Ser Pro Leu Glu
                20                  25                  30

Thr Gly Pro Cys Arg Gly Arg Lys Val Ala Phe Gly Tyr Asp Thr Asp
            35                  40                  45

Leu Glu Gly Cys Lys Gln Phe Ile Tyr Gly Gly Cys Asp Gly Asn Gly
    50                  55                  60

Asn Arg Tyr Asn Thr Leu Glu Glu Cys Gln Ala Ala Cys Glu Ser Asp
65                  70                  75                  80

Cys Asn Lys

<210> SEQ ID NO 39
<211> LENGTH: 242
<212> TYPE: DNA
<213> ORGANISM: Ostrinia nubilalis
<220> FEATURE:
<221> NAME/KEY: CDS
<222> LOCATION: (1)...(201)

<400> SEQUENCE: 39 atg aat ttc tcc aaa att ctt ttc gcg atc ttc gct tgt ttc atg gcg    48
Met Asn Phe Ser Lys Ile Leu Phe Ala Ile Phe Ala Cys Phe Met Ala
1               5                   10                  15
```

| | |
|---|---|
| ttc gcc gcc gtg tca gct gct cct gaa cca aga tgg aac ccg ttt aag<br>Phe Ala Ala Val Ser Ala Ala Pro Glu Pro Arg Trp Asn Pro Phe Lys<br>               20                   25                 30 | 96 |
| aaa ctt gag cga gtg ggc cag aac atc cga gac ggc atc gtg aag gca<br>Lys Leu Glu Arg Val Gly Gln Asn Ile Arg Asp Gly Ile Val Lys Ala<br>        35                      40                     45 | 144 |
| caa cca gct atc caa gta gtg gga gaa gcg gct aca ata tac aga ggt<br>Gln Pro Ala Ile Gln Val Val Gly Glu Ala Ala Thr Ile Tyr Arg Gly<br> 50                        55                     60 | 192 |
| ggt aaa taa tttaccacat agcaaacatc gtctagttta aaaatcgaat<br>Gly Lys *<br> 65 | 241 |
| a | 242 |

<210> SEQ ID NO 40
<211> LENGTH: 66
<212> TYPE: PRT
<213> ORGANISM: Ostrinia nubilalis

<400> SEQUENCE: 40

Met Asn Phe Ser Lys Ile Leu Phe Ala Ile Phe Ala Cys Phe Met Ala
1               5                   10                  15

Phe Ala Ala Val Ser Ala Ala Pro Glu Pro Arg Trp Asn Pro Phe Lys
            20                  25                  30

Lys Leu Glu Arg Val Gly Gln Asn Ile Arg Asp Gly Ile Val Lys Ala
        35                  40                  45

Gln Pro Ala Ile Gln Val Val Gly Glu Ala Ala Thr Ile Tyr Arg Gly
    50                  55                  60

Gly Lys
65

<210> SEQ ID NO 41
<211> LENGTH: 63
<212> TYPE: PRT
<213> ORGANISM: Ostrinia nubilalis

<400> SEQUENCE: 41

Met Asn Phe Ser Lys Ile Leu Phe Ala Ile Phe Ala Cys Phe Met Ala

```
gga atc ggc cag aga gtg agg gac agc atc atc agt gcc cga ccg gct      144
Gly Ile Gly Gln Arg Val Arg Asp Ser Ile Ile Ser Ala Arg Pro Ala
         35                  40                  45 gtt gac acc atc ttg gaa gcc cag aag ata ttc aag gga ggc gac aaa      192
Val Asp Thr Ile Leu Glu Ala Gln Lys Ile Phe Lys Gly Gly Asp Lys
     50                  55                  60 gac tga acgaaatgac gtcataattt aaatacaaat attttttaa gttagtttta        248
Asp  *
 65 caacataaaa cgttaatacc tacgtacgtt tgaggaaaaa ctcattagat tattattcat    308 gtaaattatg tagattagca aaagagaatt tcaaattacc tttgtttgga actcggattc    368 tgtgatataa tatatgttta ttttaaagta tttagttgta tctattttta ttttcacagt    428 cagcacattt cctaattaat tttgaacttt gaattagagt aag                      471
```

<210> SEQ ID NO 43
<211> LENGTH: 65
<212> TYPE: PRT
<213> ORGANISM: Ostrinia nubilalis

<400> SEQUENCE: 43

```
Met Lys Phe Ser Lys Val Phe Val Phe Ala Phe Val Ala Ala
 1               5                  10                  15

Phe Ala Thr Val Thr Ala Ser Pro Phe Asn Leu Gly Lys Glu Leu Glu
             20                  25                  30

Gly Ile Gly Gln Arg Val Arg Asp Ser Ile Ile Ser Ala Arg Pro Ala
         35                  40                  45

Val Asp Thr Ile Leu Glu Ala Gln Lys Ile Phe Lys Gly Gly Asp Lys
     50                  55                  60

Asp
 65
```

<210> SEQ ID NO 44
<211> LENGTH: 60
<212> TYPE: PRT
<213> ORGANISM: Ostrinia nubilalis

<400> SEQUENCE: 44

```
Met Lys Phe Ser Lys Val Phe Val Phe Ala Phe Val Ala Ala
 1               5                  10                  15

Phe Ala Thr Val Thr Ala Ser Pro Phe Asn Leu Gly Lys Glu Leu Glu
             20                  25                  30

Gly Ile Gly Gln Arg Val Arg Asp Ser Ile Ile Ser Ala Arg Pro Ala
         35                  40                  45

Val Asp Thr Ile Leu Glu Ala Gln Lys Ile Phe Lys
     50                  55                  60
```

<210> SEQ ID NO 45
<211> LENGTH: 464
<212> TYPE: DNA
<213> ORGANISM: Ostrinia nubilalis
<220> FEATURE:
<221> NAME/KEY: CDS
<222> LOCATION: (1)...(464)

<400> SEQUENCE: 45

```
atg caa cga gta gtg ttg tgt tcc ctg gcc gcc gtg ctc ctg gcg ttc       48
Met Gln Arg Val Val Leu Cys Ser Leu Ala Ala Val Leu Leu Ala Phe
 1               5                  10                  15
```

```
gtc gct gaa tcg tca gcg cag cgt ttc atc cag ccg acc tac agg ccg         96
Val Ala Glu Ser Ser Ala Gln Arg Phe Ile Gln Pro Thr Tyr Arg Pro
         20                  25                  30 ccg cct caa cga cca ccg aag ata tac aga ctg cga aga gat gca ggc        144
Pro Pro Gln Arg Pro Pro Lys Ile Tyr Arg Leu Arg Arg Asp Ala Gly
         35                  40                  45 gaa ccg cta tgg ctg tac caa ggt gat gat gtt cag cga gcg cca gcc        192
Glu Pro Leu Trp Leu Tyr Gln Gly Asp Asp Val Gln Arg Ala Pro Ala
 50                  55                  60 acc ggt gac cac cct tac ctg ccg cca aac atc gac gac atc cat cta        240
Thr Gly Asp His Pro Tyr Leu Pro Pro Asn Ile Asp Asp Ile His Leu
 65                  70                  75                  80 gac ccc aac acc aga tac gct cgc agc gtc gac tct cct agc gct aag        288
Asp Pro Asn Thr Arg Tyr Ala Arg Ser Val Asp Ser Pro Ser Ala Lys
                 85                  90                  95 cgt gga gga ggc agc cac agc acc tcc agt gga agc agg gat act ggc        336
Arg Gly Gly Gly Ser His Ser Thr Ser Ser Gly Ser Arg Asp Thr Gly
            100                 105                 110 gcc acg cac ccc ggg tac aat cgc cgc aac gcc cga agc ata aga ttc        384
Ala Thr His Pro Gly Tyr Asn Arg Arg Asn Ala Arg Ser Ile Arg Phe
        115                 120                 125 gac cct atc tct ccg ctg ccg tcc ccg act ttc cct aaa cca ttc gac        432
Asp Pro Ile Ser Pro Leu Pro Ser Pro Thr Phe Pro Lys Pro Phe Asp
130                 135                 140 ccg ttc aac ccc cgg cct gtt tcg ccc acc ag                             464
Pro Phe Asn Pro Arg Pro Val Ser Pro Thr
145                 150
```

<210> SEQ ID NO 46
<211> LENGTH: 154
<212> TYPE: PRT
<213> ORGANISM: Ostrinia nubilalis

<400> SEQUENCE: 46

```
Met Gln Arg Val Val Leu Cys Ser Leu Ala Ala Val Leu Leu Ala Phe
 1               5                  10                  15

Val Ala Glu Ser Ser Ala Gln Arg Phe Ile Gln Pro Thr Tyr Arg Pro
            20                  25                  30

Pro Pro Gln Arg Pro Pro Lys Ile Tyr Arg Leu Arg Arg Asp Ala Gly
        35                  40                  45

Glu Pro Leu Trp Leu Tyr Gln Gly Asp Asp Val Gln Arg Ala Pro Ala
 50                  55                  60

Thr Gly Asp His Pro Tyr Leu Pro Pro Asn Ile Asp Asp Ile His Leu
 65                  70                  75                  80

Asp Pro Asn Thr Arg Tyr Ala Arg Ser Val Asp Ser Pro Ser Ala Lys
                 85                  90                  95

Arg Gly Gly Gly Ser His Ser Thr Ser Ser Gly Ser Arg Asp Thr Gly
            100                 105                 110

Ala Thr His Pro Gly Tyr Asn Arg Arg Asn Ala Arg Ser Ile Arg Phe
        115                 120                 125

Asp Pro Ile Ser Pro Leu Pro Ser Pro Thr Phe Pro Lys Pro Phe Asp
130                 135                 140

Pro Phe Asn Pro Arg Pro Val Ser Pro Thr
145                 150
```

<210> SEQ ID NO 47
<211> LENGTH: 181
<212> TYPE: PRT
<213> ORGANISM: Ostrinia nubilalis

```
<220> FEATURE:
<221> NAME/KEY: VARIANT
<222> LOCATION: 155
<223> OTHER INFORMATION: Xaa = Any Amino Acid

<400> SEQUENCE: 47
```

| | | | | | | | | | | | | | | | |
|---|---|---|---|---|---|---|---|---|---|---|---|---|---|---|---|
|Met|Gln|Arg|Val|Val|Leu|Cys|Ser|Leu|Ala|Ala|Val|Leu|Leu|Ala|Phe|
|1| | | |5| | | | |10| | | | |15| |
|Val|Ala|Glu|Ser|Ser|Ala|Gln|Arg|Phe|Ile|Gln|Pro|Thr|Tyr|Arg|Pro|
| | | |20| | | | |25| | | | |30| | |
|Pro|Pro|Gln|Arg|Pro|Pro|Lys|Ile|Tyr|Arg|Leu|Arg|Arg|Asp|Ala|Gly|
| | | |35| | | | |40| | | | |45| | |
|Glu|Pro|Leu|Trp|Leu|Tyr|Gln|Gly|Asp|Asp|Val|Gln|Arg|Ala|Pro|Ala|
| |50| | | | |55| | | | |60| | | | |
|Thr|Gly|Asp|His|Pro|Tyr|Leu|Pro|Pro|Asn|Ile|Asp|Asp|Ile|His|Leu|
|65| | | | |70| | | | |75| | | | |80|
|Asp|Pro|Asn|Thr|Arg|Tyr|Ala|Arg|Ser|Val|Asp|Ser|Pro|Ser|Ala|Lys|
| | | | |85| | | | |90| | | | |95| |
|Arg|Gly|Gly|Ser|His|Ser|Thr|Ser|Ser|Gly|Ser|Arg|Asp|Thr|Gly|
| | | |100| | | | |105| | | | |110| | |
|Ala|Thr|His|Pro|Gly|Tyr|Asn|Arg|Arg|Asn|Ala|Arg|Ser|Ile|Arg|Phe|
| | | |115| | | | |120| | | | |125| | |
|Asp|Pro|Ile|Ser|Pro|Leu|Pro|Ser|Pro|Thr|Phe|Pro|Lys|Pro|Phe|Asp|
| | | |130| | | | |135| | | | |140| | |
|Pro|Phe|Asn|Pro|Arg|Pro|Val|Ser|Pro|Thr|Xaa|Pro|Phe|Pro|Leu|Tyr|
|145| | | | |150| | | | |155| | | | |160|
|Ala|Arg|Ser|Arg|Arg|Asp|Ile|Gln|Phe|Pro|Gln|Lys|Pro|Lys|His|His|
| | | | |165| | | | |170| | | | |175| |
|Asp|Ile|Val|Leu|Thr|
| | | | |180| |

```
<210> SEQ ID NO 48
<211> LENGTH: 538
<212> TYPE: DNA
<213> ORGANISM: Heliothis virescens
<220> FEATURE:
<221> NAME/KEY: CDS
<222> LOCATION: (1)...(432)

<400> SEQUENCE: 48 atg gca aaa tcc att ttc gcg ctt gga gtt atc gca gtt ctg ttg ata       48
Met Ala Lys Ser Ile Phe Ala Leu Gly Val Ile Ala Val Leu Leu Ile
1               5                   10                  15 aca gaa tcc aac tgt tgg aga agt gat ctc cct atc ata ctc ccg act       96
Thr Glu Ser Asn Cys Trp Arg Ser Asp Leu Pro Ile Ile Leu Pro Thr
            20                  25                  30 tat aaa cct cct cgt acc ccg agc acc gtt att atc agg aca gta cgc      144
Tyr Lys Pro Pro Arg Thr Pro Ser Thr Val Ile Ile Arg Thr Val Arg
        35                  40                  45 gaa gcc gga gat aaa ccg tta tgg ctc tac caa gga gac gat cac ccg      192
Glu Ala Gly Asp Lys Pro Leu Trp Leu Tyr Gln Gly Asp Asp His Pro
    50                  55                  60 cga gcc cct tca agc ggc gat cat cct gta ctg ccc ccg atc ata gac      240
Arg Ala Pro Ser Ser Gly Asp His Pro Val Leu Pro Pro Ile Ile Asp
65                  70                  75                  80 gat gtg aaa ctg gac ccc aac aga cgg tac gcg cgt agt gtg aac gag      288
Asp Val Lys Leu Asp Pro Asn Arg Arg Tyr Ala Arg Ser Val Asn Glu
                85                  90                  95 ccc tcg tct cag gag cat cac gaa cgc ttt gtg agg agc ttc gac tcc      336
```

```
Pro Ser Ser Gln Glu His His Glu Arg Phe Val Arg Ser Phe Asp Ser
            100                 105                 110 cgc agc agc agg cat cac ggc ggc agt cac tcc acg tcc agc ggc agc    384
Arg Ser Ser Arg His His Gly Gly Ser His Ser Thr Ser Ser Gly Ser
        115                 120                 125 cgc gac act gga gct act cat ccg gga tac aat cgt cgt aac tca taa    432
Arg Asp Thr Gly Ala Thr His Pro Gly Tyr Asn Arg Arg Asn Ser *
    130                 135                 140 tctgtggttt aatgtattag atatttgtgt ttaacattaa aacattttg aaattgtcta   492 ctcgaataaa tacatttacc tattttaaaa aaaaaaaaaa aaaaaa                 538

<210> SEQ ID NO 49
<211> LENGTH: 143
<212> TYPE: PRT
<213> ORGANISM: Heliothis virescens

<400> SEQUENCE: 49

Met Ala Lys Ser Ile Phe Ala Leu Gly Val Ile Ala Val Leu Leu Ile
 1               5                  10                  15

Thr Glu Ser Asn Cys Trp Arg Ser Asp Leu Pro Ile Ile Leu Pro Thr
            20                  25                  30

Tyr Lys Pro Pro Arg Thr Pro Ser Thr Val Ile Ile Arg Thr Val Arg
        35                  40                  45

Glu Ala Gly Asp Lys Pro Leu Trp Leu Tyr Gln Gly Asp Asp His Pro
    50                  55                  60

Arg Ala Pro Ser Ser Gly Asp His Pro Val Leu Pro Pro Ile Ile Asp
65                  70                  75                  80

Asp Val Lys Leu Asp Pro Asn Arg Arg Tyr Ala Arg Ser Val Asn Glu
                85                  90                  95

Pro Ser Ser Gln Glu His His Glu Arg Phe Val Arg Ser Phe Asp Ser
            100                 105                 110

Arg Ser Ser Arg His His Gly Gly Ser His Ser Thr Ser Ser Gly Ser
        115                 120                 125

Arg Asp Thr Gly Ala Thr His Pro Gly Tyr Asn Arg Arg Asn Ser
    130                 135                 140

<210> SEQ ID NO 50
<211> LENGTH: 143
<212> TYPE: PRT
<213> ORGANISM: Heliothis virescens

<400> SEQUENCE: 50

Met Ala Lys Ser Ile Phe Ala Leu Gly Val Ile Ala Val Leu Leu Ile
 1               5                  10                  15

Thr Glu Ser Asn Cys Trp Arg Ser Asp Leu Pro Ile Ile Leu Pro Thr
            20                  25                  30

Tyr Lys Pro Pro Arg Thr Pro Ser Thr Val Ile Ile Arg Thr Val Arg
        35                  40                  45

Glu Ala Gly Asp Lys Pro Leu Trp Leu Tyr Gln Gly Asp Asp His Pro
    50                  55                  60

Arg Ala Pro Ser Ser Gly Asp His Pro Val Leu Pro Pro Ile Ile Asp
65                  70                  75                  80

Asp Val Lys Leu Asp Pro Asn Arg Arg Tyr Ala Arg Ser Val Asn Glu
                85                  90                  95

Pro Ser Ser Gln Glu His His Glu Arg Phe Val Arg Ser Phe Asp Ser
            100                 105                 110
```

```
Arg Ser Ser Arg His His Gly Gly Ser His Ser Thr Ser Ser Gly Ser
        115                 120                 125

Arg Asp Thr Gly Ala Thr His Pro Gly Tyr Asn Arg Arg Asn Ser
    130                 135                 140

<210> SEQ ID NO 51
<211> LENGTH: 481
<212> TYPE: DNA
<213> ORGANISM: Heliothis virescens
<220> FEATURE:
<221> NAME/KEY: CDS
<222> LOCATION: (1)...(429)

<400> SEQUENCE: 51 atg aag tca gta ctt gta ctt tgc gtt gtt gcg gtg ttg cat acg gca      48
Met Lys Ser Val Leu Val Leu Cys Val Val Ala Val Leu His Thr Ala
 1               5                  10                  15 gca tcc tca ggc tgg aat aaa aat aat ggc ggc ata cta ccg acc         96
Ala Ser Ser Gly Trp Asn Lys Asn Asn Gly Gly Ile Ile Leu Pro Thr
                20                  25                  30 ttt aga cct cca cct ata tgg cca gga att acc agg aca gta cgt gaa    144
Phe Arg Pro Pro Pro Ile Trp Pro Gly Ile Thr Arg Thr Val Arg Glu
            35                  40                  45 gct gga gat caa cct tta tgg ctg tac caa gga gac aat cac ccg cga    192
Ala Gly Asp Gln Pro Leu Trp Leu Tyr Gln Gly Asp Asn His Pro Arg
    50                  55                  60 gcc cct tca agc ggc gat cat cct gta ctg ccc tcg atc ata gac gat    240
Ala Pro Ser Ser Gly Asp His Pro Val Leu Pro Ser Ile Ile Asp Asp
65                  70                  75                  80 gtg aag ttg gac ccc aac agg cgg tac gtg cgt agt gtg aac gag ccg    288
Val Lys Leu Asp Pro Asn Arg Arg Tyr Val Arg Ser Val Asn Glu Pro
                85                  90                  95 tcg tca cag gag cat cac gaa cgc ttt gtg agg agc ttc gac tcc cgc    336
Ser Ser Gln Glu His His Glu Arg Phe Val Arg Ser Phe Asp Ser Arg
            100                 105                 110 agc agc agg cat cac ggc ggc agc cac tct acg tcc agc ggc agc cgc    384
Ser Ser Arg His His Gly Gly Ser His Ser Thr Ser Ser Gly Ser Arg
        115                 120                 125 gac act gga gct act cat ccg gga tac aat cgt cgt aac tca taa        429
Asp Thr Gly Ala Thr His Pro Gly Tyr Asn Arg Arg Asn Ser *
    130                 135                 140 tctgtggttt aatccattag aaatttgtgt ttgtattttg ataaaaacaa tg           481

<210> SEQ ID NO 52
<211> LENGTH: 142
<212> TYPE: PRT
<213> ORGANISM: Heliothis virescens

<400> SEQUENCE: 52

Met Lys Ser Val Leu Val Leu Cys Val Val Ala Val Leu His Thr Ala
 1               5                  10                  15

Ala Ser Ser Gly Trp Asn Lys Asn Asn Gly Gly Ile Ile Leu Pro Thr
                20                  25                  30

Phe Arg Pro Pro Pro Ile Trp Pro Gly Ile Thr Arg Thr Val Arg Glu
            35                  40                  45

Ala Gly Asp Gln Pro Leu Trp Leu Tyr Gln Gly Asp Asn His Pro Arg
    50                  55                  60

Ala Pro Ser Ser Gly Asp His Pro Val Leu Pro Ser Ile Ile Asp Asp
65                  70                  75                  80

Val Lys Leu Asp Pro Asn Arg Arg Tyr Val Arg Ser Val Asn Glu Pro
```

```
                            85                  90                  95
Ser Ser Gln Glu His His Glu Arg Phe Val Arg Ser Phe Asp Ser Arg
            100                 105                 110

Ser Ser Arg His His Gly Gly Ser His Ser Thr Ser Ser Gly Ser Arg
            115                 120                 125

Asp Thr Gly Ala Thr His Pro Gly Tyr Asn Arg Arg Asn Ser
            130                 135                 140

<210> SEQ ID NO 53
<211> LENGTH: 142
<212> TYPE: PRT
<213> ORGANISM: Heliothis virescens

<400> SEQUENCE: 53

Met Lys Ser Val Leu Val Leu Cys Val Val Ala Val Leu His Thr Ala
1               5                   10                  15

Ala Ser Ser Gly Trp Asn Lys Asn Asn Gly Gly Ile Ile Leu Pro Thr
            20                  25                  30

Phe Arg Pro Pro Ile Trp Pro Gly Ile Thr Arg Thr Val Arg Glu
        35                  40                  45

Ala Gly Asp Gln Pro Leu Trp Leu Tyr Gln Gly Asp Asn His Pro Arg
    50                  55                  60

Ala Pro Ser Ser Gly Asp His Pro Val Leu Pro Ser Ile Ile Asp Asp
65                  70                  75                  80

Val Lys Leu Asp Pro Asn Arg Arg Tyr Val Arg Ser Val Asn Glu Pro
                85                  90                  95

Ser Ser Gln Glu His His Glu Arg Phe Val Arg Ser Phe Asp Ser Arg
            100                 105                 110

Ser Ser Arg His His Gly Gly Ser His Ser Thr Ser Ser Gly Ser Arg
            115                 120                 125

Asp Thr Gly Ala Thr His Pro Gly Tyr Asn Arg Arg Asn Ser
            130                 135                 140

<210> SEQ ID NO 54
<211> LENGTH: 418
<212> TYPE: DNA
<213> ORGANISM: Heliothis virescens
<220> FEATURE:
<221> NAME/KEY: CDS
<222> LOCATION: (1)...(192)

<400> SEQUENCE: 54 atg aat tct aaa ata gtg att ttt ttg tgc att tgt ttt gtt ctt gtg       48
Met Asn Ser Lys Ile Val Ile Phe Leu Cys Ile Cys Phe Val Leu Val
1               5                   10                  15 tca acg gca acg gca tgg gat ttg ttt aaa gaa att gag gga gca ggt       96
Ser Thr Ala Thr Ala Trp Asp Leu Phe Lys Glu Ile Glu Gly Ala Gly
            20                  25                  30 cag agg gtg cgt gat gcc atc atc agc gct ggc cct gcg gtc gac gtg      144
Gln Arg Val Arg Asp Ala Ile Ile Ser Ala Gly Pro Ala Val Asp Val
        35                  40                  45 ctc acc aaa act aaa gga tta ttc gac agc tct gaa gaa aaa gat tag      192
Leu Thr Lys Thr Lys Gly Leu Phe Asp Ser Ser Glu Glu Lys Asp  *
    50                  55                  60 tttataataa aatgtaaact cagcttagat taggtacaga cgctagccgg tcaacgtacc    252
aacgtctgtc aaattttacc aatcgaactt taaccttcca ctgttgtgat aaggttgaaa    312
atctattgag gaaatttgtc agattgtgat ttgccaggtc gacgtgttgg tatctgtaaa    372
```

```
tttatacttt cattaagtaa tattgtagct gtaacactga aagaac        418
```

<210> SEQ ID NO 55
<211> LENGTH: 57
<212> TYPE: PRT
<213> ORGANISM: Heliothis virescens

<400> SEQUENCE: 55

```
Met Asn Ser Lys Ile Val Ile Phe Leu Cys Ile Cys Phe Val Leu Val
 1               5                  10                  15

Ser Thr Ala Thr Ala Trp Asp Leu Phe Lys Glu Ile Glu Gly Ala Gly
            20                  25                  30

Gln Arg Val Arg Asp Ala Ile Ile Ser Ala Gly Pro Ala Val Asp Val
        35                  40                  45

Leu Thr Lys Thr Lys Gly Leu Phe Asp
    50                  55
```

<210> SEQ ID NO 56
<211> LENGTH: 63
<212> TYPE: PRT
<213> ORGANISM: Heliothis virescens

<400> SEQUENCE: 56

```
Met Asn Ser Lys Ile Val Ile Phe Leu Cys Ile Cys Phe Val Leu Val
 1               5                  10                  15

Ser Thr Ala Thr Ala Trp Asp Leu Phe Lys Glu Ile Glu Gly Ala Gly
            20                  25                  30

Gln Arg Val Arg Asp Ala Ile Ile Ser Ala Gly Pro Ala Val Asp Val
        35                  40                  45

Leu Thr Lys Thr Lys Gly Leu Phe Asp Ser Ser Glu Glu Lys Asp
    50                  55                  60
```

<210> SEQ ID NO 57
<211> LENGTH: 275
<212> TYPE: DNA
<213> ORGANISM: Heliothis virescens
<220> FEATURE:
<221> NAME/KEY: CDS
<222> LOCATION: (1)...(189)

<400> SEQUENCE: 57

```
atg aac ttc tca agg ata ttt ttc ttc gtg ttc gcg tgt ttg gta gta     48
Met Asn Phe Ser Arg Ile Phe Phe Phe Val Phe Ala Cys Leu Val Val
 1               5                  10                  15 ctg tgc agc gtg tcg gcg gcg cct gag ccg agg tgg aag gtc ttc aag     96
Leu Cys Ser Val Ser Ala Ala Pro Glu Pro Arg Trp Lys Val Phe Lys
            20                  25                  30 aaa att gag aag atg ggt cgc aac atc cga gac ggc atc gta aag gct    144
Lys Ile Glu Lys Met Gly Arg Asn Ile Arg Asp Gly Ile Val Lys Ala
        35                  40                  45 gga cca gcg ata gca gtt ctc ggc caa gct aaa gca tta gga taa        189
Gly Pro Ala Ile Ala Val Leu Gly Gln Ala Lys Ala Leu Gly *
    50                  55                  60 ataattattg tattattaat attaagagtt taatatctaa gtcgcattta aatactcatt   249
ctgccataaa taaatgtatt ttaagt                                        275
```

<210> SEQ ID NO 58
<211> LENGTH: 62
<212> TYPE: PRT
<213> ORGANISM: Heliothis virescens

```
<400> SEQUENCE: 58

Met Asn Phe Ser Arg Ile Phe Phe Val Phe Ala Cys Leu Val Val
1               5                   10                  15

Leu Cys Ser Val Ser Ala Ala Pro Glu Pro Arg Trp Lys Val Phe Lys
        20                  25                  30

Lys Ile Glu Lys Met Gly Arg Asn Ile Arg Asp Gly Ile Val Lys Ala
            35                  40                  45

Gly Pro Ala Ile Ala Val Leu Gly Gln Ala Lys Ala Leu Gly
        50                  55                  60

<210> SEQ ID NO 59
<211> LENGTH: 62
<212> TYPE: PRT
<213> ORGANISM: Heliothis virescens

<400> SEQUENCE: 59

Met Asn Phe Ser Arg Ile Phe Phe Val Phe Ala Cys Leu Val Val
1               5                   10                  15

Leu Cys Ser Val Ser Ala Ala Pro Glu Pro Arg Trp Lys Val Phe Lys
        20                  25                  30

Lys Ile Glu Lys Met Gly Arg Asn Ile Arg Asp Gly Ile Val Lys Ala
            35                  40                  45

Gly Pro Ala Ile Ala Val Leu Gly Gln Ala Lys Ala Leu Gly
        50                  55                  60

<210> SEQ ID NO 60
<211> LENGTH: 397
<212> TYPE: DNA
<213> ORGANISM: Helicoverpa zea
<220> FEATURE:
<221> NAME/KEY: CDS
<222> LOCATION: (1)...(192)
<220> FEATURE:
<221> NAME/KEY: misc_feature
<222> LOCATION: 229, 267, 326
<223> OTHER INFORMATION: n = A,T,C or G

<400> SEQUENCE: 60 atg aat tcc aaa att gta tta ttc ctg tgt gtt tgt ttg gtg ctt gtg          48
Met Asn Ser Lys Ile Val Leu Phe Leu Cys Val Cys Leu Val Leu Val
1               5                   10                  15 tcg acg gca aca gca tgg gac ttc ttt aag gaa ctt gaa gga gca gga          96
Ser Thr Ala Thr Ala Trp Asp Phe Phe Lys Glu Leu Glu Gly Ala Gly
            20                  25                  30 caa aga gtc cgc gat gct atc atc agc gct ggc cct gct gtc gac gtt         144
Gln Arg Val Arg Asp Ala Ile Ile Ser Ala Gly Pro Ala Val Asp Val
        35                  40                  45 ctc acc aaa gct aag ggg cta tac gac agc tcc gaa gaa aaa gat tag         192
Leu Thr Lys Ala Lys Gly Leu Tyr Asp Ser Ser Glu Glu Lys Asp *
    50                  55                  60 gatataagcc aatcaaatca tcatcatcat agtcaanaat caatcaaaat caaaactcat       252
ttattcaaac ttggntgcaa acaagcact  tttcgaacgt caaaaaaaaa tttacataag       312 acagccccc  aatncgccca ccctcacca  acttccctaa gttgtttttt gctggggaaa       372
gaaagaagtt ggcgcaacaa aacct                                             397

<210> SEQ ID NO 61
<211> LENGTH: 63
<212> TYPE: PRT
<213> ORGANISM: Heliocoverpa zea
```

-continued

```
<400> SEQUENCE: 61

Met Asn Ser Lys Ile Val Leu Phe Leu Cys Val Cys Leu Val Leu Val
 1               5                  10                  15

Ser Thr Ala Thr Ala Trp Asp Phe Phe Lys Glu Leu Glu Gly Ala Gly
            20                  25                  30

Gln Arg Val Arg Asp Ala Ile Ile Ser Ala Gly Pro Ala Val Asp Val
        35                  40                  45

Leu Thr Lys Ala Lys Gly Leu Tyr Asp Ser Ser Glu Glu Lys Asp
    50                  55                  60

<210> SEQ ID NO 62
<211> LENGTH: 57
<212> TYPE: PRT
<213> ORGANISM: Heliocoverpa zea

<400> SEQUENCE: 62

Met Asn Ser Lys Ile Val Leu Phe Leu Cys Val Cys Leu Val Leu Val
 1               5                  10                  15

Ser Thr Ala Thr Ala Trp Asp Phe Phe Lys Glu Leu Glu Gly Ala Gly
            20                  25                  30

Gln Arg Val Arg Asp Ala Ile Ile Ser Ala Gly Pro Ala Val Asp Val
        35                  40                  45

Leu Thr Lys Ala Lys Gly Leu Tyr Asp
    50                  55

<210> SEQ ID NO 63
<211> LENGTH: 263
<212> TYPE: DNA
<213> ORGANISM: Manduca sexta
<220> FEATURE:
<221> NAME/KEY: CDS
<222> LOCATION: (1)...(186)
<220> FEATURE:
<221> NAME/KEY: misc_feature
<222> LOCATION: 56, 65, 108, 123
<223> OTHER INFORMATION: n = A,T,C or G

<400> SEQUENCE: 63 atg aac ttc tct cgc gtt ttg ttc ttc gtg ttt gct tgc gtc agc gca      48
Met Asn Phe Ser Arg Val Leu Phe Phe Val Phe Ala Cys Val Ser Ala
 1               5                  10                  15 ttc gcc nng act tca gnt gcg ccc tgt aat ccc ttt aag gaa ctg gag      96
Phe Ala Xaa Thr Ser Xaa Ala Pro Cys Asn Pro Phe Lys Glu Leu Glu
            20                  25                  30 aga gct ggc can cga gtc cgc gac gcn gtc atc agc gcc gcg cct gca     144
Arg Ala Gly Xaa Arg Val Arg Asp Ala Val Ile Ser Ala Ala Pro Ala
        35                  40                  45 gtc gcg acc gtc gga cag gcg gcc gcc atc gcc agc gga taa              186
Val Ala Thr Val Gly Gln Ala Ala Ala Ile Ala Ser Gly *
    50                  55                  60 taaccaatgg atgcttcact attcattatt atcataaatt atatgtgcca taccttaata    246
tgttccttac atttgta                                                   263

<210> SEQ ID NO 64
<211> LENGTH: 61
<212> TYPE: PRT
<213> ORGANISM: Manduca sexta
<220> FEATURE:
<221> NAME/KEY: VARIANT
<222> LOCATION: 19, 22, 36
<223> OTHER INFORMATION: Xaa = Any Amino Acid
```

<400> SEQUENCE: 64

| Met | Asn | Phe | Ser | Arg | Val | Leu | Phe | Phe | Val | Phe | Ala | Cys | Val | Ser | Ala |
| 1 | | | | 5 | | | | | 10 | | | | | 15 | |

| Phe | Ala | Xaa | Thr | Ser | Xaa | Ala | Pro | Cys | Asn | Pro | Phe | Lys | Glu | Leu | Glu |
| | | | 20 | | | | | | 25 | | | | | 30 | |

| Arg | Ala | Gly | Xaa | Arg | Val | Arg | Asp | Ala | Val | Ile | Ser | Ala | Ala | Pro | Ala |
| | | | 35 | | | | | 40 | | | | | 45 | | |

| Val | Ala | Thr | Val | Gly | Gln | Ala | Ala | Ala | Ile | Ala | Ser | Gly |
| | 50 | | | | | 55 | | | | | 60 | |

<210> SEQ ID NO 65
<211> LENGTH: 61
<212> TYPE: PRT
<213> ORGANISM: Manduca sexta
<220> FEATURE:
<221> NAME/KEY: VARIANT
<222> LOCATION: 19, 22, 36
<223> OTHER INFORMATION: Xaa = Any Amino Acid

<400> SEQUENCE: 65

| Met | Asn | Phe | Ser | Arg | Val | Leu | Phe | Phe | Val | Phe | Ala | Cys | Val | Ser | Ala |
| 1 | | | | 5 | | | | | 10 | | | | | 15 | |

| Phe | Ala | Xaa | Thr | Ser | Xaa | Ala | Pro | Cys | Asn | Pro | Phe | Lys | Glu | Leu | Glu |
| | | | 20 | | | | | | 25 | | | | | 30 | |

| Arg | Ala | Gly | Xaa | Arg | Val | Arg | Asp | Ala | Val | Ile | Ser | Ala | Ala | Pro | Ala |
| | | | 35 | | | | | 40 | | | | | 45 | | |

| Val | Ala | Thr | Val | Gly | Gln | Ala | Ala | Ala | Ile | Ala | Ser | Gly |
| | 50 | | | | | 55 | | | | | 60 | |

<210> SEQ ID NO 66
<211> LENGTH: 367
<212> TYPE: DNA
<213> ORGANISM: Manduca sexta
<220> FEATURE:
<221> NAME/KEY: CDS
<222> LOCATION: (1)...(186)

<400> SEQUENCE: 66

```
atg aac ttc tcc agg atc ttc ttc ttc gtc ttc gcc ttg gtt ctt ggc      48
Met Asn Phe Ser Arg Ile Phe Phe Phe Val Phe Ala Leu Val Leu Gly
1               5                   10                  15 atg tct gct gta tca gca gct ccc aaa tgg aag att ttt aag aaa att      96
Met Ser Ala Val Ser Ala Ala Pro Lys Trp Lys Ile Phe Lys Lys Ile
            20                  25                  30 gaa aaa gtc gga agg aac gtc cgt gat ggt att atc aaa gcg gga cca     144
Glu Lys Val Gly Arg Asn Val Arg Asp Gly Ile Ile Lys Ala Gly Pro
        35                  40                  45 gcg ata caa gtg ctg gga cag gcg aaa gcg att gga aaa tga             186
Ala Ile Gln Val Leu Gly Gln Ala Lys Ala Ile Gly Lys *
    50                  55                  60 agctgtattg cagtgttctt aaagtcttta ttacctcaac aaaatgccat aactgtatac    246
tcttatagat aagtgaatca gaagaatgat ctgatgtaga gataatgaat ctgcctgtat    306
ttctttgaat aaattaagtg aatgtaaata ttttttttaaa taaataatttt ttattaatct   366 t                                                                     367
```

<210> SEQ ID NO 67
<211> LENGTH: 61
<212> TYPE: PRT
<213> ORGANISM: Manduca sexta -continued

```
<400> SEQUENCE: 67

Met Asn Phe Ser Arg Ile Phe Phe Val Phe Ala Leu Val Leu Gly
 1               5                  10                  15

Met Ser Ala Val Ser Ala Ala Pro Lys Trp Lys Ile Phe Lys Lys Ile
                20                  25                  30

Glu Lys Val Gly Arg Asn Val Arg Asp Gly Ile Ile Lys Ala Gly Pro
            35                  40                  45

Ala Ile Gln Val Leu Gly Gln Ala Lys Ala Ile Gly Lys
        50                  55                  60

<210> SEQ ID NO 68
<211> LENGTH: 61
<212> TYPE: PRT
<213> ORGANISM: Manduca sexta

<400> SEQUENCE: 68

Met Asn Phe Ser Arg Ile Phe Phe Val Phe Ala Leu Val Leu Gly
 1               5                  10                  15

Met Ser Ala Val Ser Ala Ala Pro Lys Trp Lys Ile Phe Lys Lys Ile
                20                  25                  30

Glu Lys Val Gly Arg Asn Val Arg Asp Gly Ile Ile Lys Ala Gly Pro
            35                  40                  45

Ala Ile Gln Val Leu Gly Gln Ala Lys Ala Ile Gly Lys
        50                  55                  60

<210> SEQ ID NO 69
<211> LENGTH: 230
<212> TYPE: DNA
<213> ORGANISM: Manduca sexta
<220> FEATURE:
<221> NAME/KEY: CDS
<222> LOCATION: (1)...(135)

<400> SEQUENCE: 69 atg gct tca gct gca cct tgg aat ccc ttc aag gag ctg gag aga gct      48
Met Ala Ser Ala Ala Pro Trp Asn Pro Phe Lys Glu Leu Glu Arg Ala
 1               5                  10                  15 ggt cag cga gtc cgc gac gcc atc atc agc gca ggc cca gca gtc gcg      96
Gly Gln Arg Val Arg Asp Ala Ile Ile Ser Ala Gly Pro Ala Val Ala
                20                  25                  30 acc gtc gga cag gcg gcc gct atc gcc agg ggt ggt taa gcaacgaatg      145
Thr Val Gly Gln Ala Ala Ala Ile Ala Arg Gly Gly *
            35                  40 ctttatctat gaatatgctt attaattata taagtttcat gtatctttat tacaataatg   205
atttggtata ataaacgtca ataat                                         230

<210> SEQ ID NO 70
<211> LENGTH: 44
<212> TYPE: PRT
<213> ORGANISM: Manduca sexta

<400> SEQUENCE: 70

Met Ala Ser Ala Ala Pro Trp Asn Pro Phe Lys Glu Leu Glu Arg Ala
 1               5                  10                  15

Gly Gln Arg Val Arg Asp Ala Ile Ile Ser Ala Gly Pro Ala Val Ala
                20                  25                  30

Thr Val Gly Gln Ala Ala Ala Ile Ala Arg Gly Gly
            35                  40
```

```
<210> SEQ ID NO 71
<211> LENGTH: 44
<212> TYPE: PRT
<213> ORGANISM: Manduca sexta

<400> SEQUENCE: 71

Met Ala Ser Ala Ala Pro Trp Asn Pro Phe Lys Glu Leu Glu Arg Ala
 1               5                  10                  15

Gly Gln Arg Val Arg Asp Ala Ile Ile Ser Ala Gly Pro Ala Val Ala
             20                  25                  30

Thr Val Gly Gln Ala Ala Ala Ile Ala Arg Gly Gly
         35                  40

<210> SEQ ID NO 72
<211> LENGTH: 287
<212> TYPE: DNA
<213> ORGANISM: Manduca sexta
<220> FEATURE:
<221> NAME/KEY: CDS
<222> LOCATION: (25)...(287)

<400> SEQUENCE: 72
actagtggat cccccgggct gcag ggt gaa aca atc atg aaa ttg cta ctg      51
                          Gly Glu Thr Ile Met Lys Leu Leu Leu
                           1               5 att ttg ggc gtt gcg ctg gtg ttg ctc ttt ggt gag tcc tta ggt cag      99
Ile Leu Gly Val Ala Leu Val Leu Leu Phe Gly Glu Ser Leu Gly Gln
 10                  15                  20                  25 cga ttt agc cag cct acg ttc aag cta cct caa ggt aga ttg aca ctt     147
Arg Phe Ser Gln Pro Thr Phe Lys Leu Pro Gln Gly Arg Leu Thr Leu
                 30                  35                  40 agt cga aaa ttt agg gag tcc ggc aat gag cca cta tgg ttg tat caa     195
Ser Arg Lys Phe Arg Glu Ser Gly Asn Glu Pro Leu Trp Leu Tyr Gln
             45                  50                  55 ggc gac aac ata cca aag gca cca tca act gca gaa cat ccc ttc ctt     243
Gly Asp Asn Ile Pro Lys Ala Pro Ser Thr Ala Glu His Pro Phe Leu
         60                  65                  70 ccg tct ata ata gat gat gtg aag ttc aat cca gat aga aga ta          287
Pro Ser Ile Ile Asp Asp Val Lys Phe Asn Pro Asp Arg Arg
     75                  80                  85

<210> SEQ ID NO 73
<211> LENGTH: 87
<212> TYPE: PRT
<213> ORGANISM: Manduca sexta

<400> SEQUENCE: 73

Gly Glu Thr Ile Met Lys Leu Leu Ile Leu Gly Val Ala Leu Val
 1               5                  10                  15

Leu Leu Phe Gly Glu Ser Leu Gly Gln Arg Phe Ser Gln Pro Thr Phe
             20                  25                  30

Lys Leu Pro Gln Gly Arg Leu Thr Leu Ser Arg Lys Phe Arg Glu Ser
         35                  40                  45

Gly Asn Glu Pro Leu Trp Leu Tyr Gln Gly Asp Asn Ile Pro Lys Ala
     50                  55                  60

Pro Ser Thr Ala Glu His Pro Phe Leu Pro Ser Ile Ile Asp Asp Val
 65                  70                  75                  80

Lys Phe Asn Pro Asp Arg Arg
                 85

<210> SEQ ID NO 74
```

```
<211> LENGTH: 87
<212> TYPE: PRT
<213> ORGANISM: Manduca sexta

<400> SEQUENCE: 74

Gly Glu Thr Ile Met Lys Leu Leu Ile Leu Gly Val Ala Leu Val
1               5                   10                  15

Leu Leu Phe Gly Glu Ser Leu Gly Gln Arg Phe Ser Gln Pro Thr Phe
            20                  25                  30

Lys Leu Pro Gln Gly Arg Leu Thr Leu Ser Arg Lys Phe Arg Glu Ser
        35                  40                  45

Gly Asn Glu Pro Leu Trp Leu Tyr Gln Gly Asp Asn Ile Pro Lys Ala
    50                  55                  60

Pro Ser Thr Ala Glu His Pro Phe Leu Pro Ser Ile Ile Asp Val
65                  70                  75                  80

Lys Phe Asn Pro Asp Arg Arg
                85

<210> SEQ ID NO 75
<211> LENGTH: 220
<212> TYPE: DNA
<213> ORGANISM: Manduca sexta
<220> FEATURE:
<221> NAME/KEY: CDS
<222> LOCATION: (1)...(192)

<400> SEQUENCE: 75 atg aac ttc tcc cgc att ttc ttc ttt gtg ttc gct ctg gtc ctc agt    48
Met Asn Phe Ser Arg Ile Phe Phe Phe Val Phe Ala Leu Val Leu Ser
1               5                   10                  15 ctg tcg gcg gtg tcc gcg gct cct gaa ccg aaa tgg aag gtg ttt aag    96
Leu Ser Ala Val Ser Ala Ala Pro Glu Pro Lys Trp Lys Val Phe Lys
            20                  25                  30 aaa att gaa aaa atg ggc cga aat atc aga gat gga att atc aaa gct   144
Lys Ile Glu Lys Met Gly Arg Asn Ile Arg Asp Gly Ile Ile Lys Ala
        35                  40                  45 ggc cca gcg att gaa gtc ctt ggc gca gct aag gcc ata gga aag tga   192
Gly Pro Ala Ile Glu Val Leu Gly Ala Ala Lys Ala Ile Gly Lys *
    50                  55                  60 acctaatgct tccttgttag tctattttt                                    220

<210> SEQ ID NO 76
<211> LENGTH: 63
<212> TYPE: PRT
<213> ORGANISM: Manduca sexta

<400> SEQUENCE: 76

Met Asn Phe Ser Arg Ile Phe Phe Phe Val Phe Ala Leu Val Leu Ser
1               5                   10                  15

Leu Ser Ala Val Ser Ala Ala Pro Glu Pro Lys Trp Lys Val Phe Lys
            20                  25                  30

Lys Ile Glu Lys Met Gly Arg Asn Ile Arg Asp Gly Ile Ile Lys Ala
        35                  40                  45

Gly Pro Ala Ile Glu Val Leu Gly Ala Ala Lys Ala Ile Gly Lys
    50                  55                  60

<210> SEQ ID NO 77
<211> LENGTH: 63
<212> TYPE: PRT
<213> ORGANISM: Manduca sexta
```

```
<400> SEQUENCE: 77

Met Asn Phe Ser Arg Ile Phe Phe Val Phe Ala Leu Val Leu Ser
 1               5                  10                  15

Leu Ser Ala Val Ser Ala Ala Pro Glu Pro Lys Trp Lys Val Phe Lys
            20                  25                  30

Lys Ile Glu Lys Met Gly Arg Asn Ile Arg Asp Gly Ile Ile Lys Ala
            35                  40                  45

Gly Pro Ala Ile Glu Val Leu Gly Ala Ala Lys Ala Ile Gly Lys
 50                  55                  60

<210> SEQ ID NO 78
<211> LENGTH: 293
<212> TYPE: DNA
<213> ORGANISM: Manduca sexta
<220> FEATURE:
<221> NAME/KEY: CDS
<222> LOCATION: (1)...(279)

<400> SEQUENCE: 78 atg aat tta tta tat ttc ctt tcg ttt ctg ggc tgt att act ctc tgc      48
Met Asn Leu Leu Tyr Phe Leu Ser Phe Leu Gly Cys Ile Thr Leu Cys
 1               5                  10                  15 ttg agt gcc ggt ttg tac aaa cct cct aat aac ata gaa tct gag aac      96
Leu Ser Ala Gly Leu Tyr Lys Pro Pro Asn Asn Ile Glu Ser Glu Asn
            20                  25                  30 gaa gtt tac acc gga aat att tgc ttc ttg cca ttg gaa gtt ggg gta     144
Glu Val Tyr Thr Gly Asn Ile Cys Phe Leu Pro Leu Glu Val Gly Val
            35                  40                  45 tgc cga gct ctg ttc ttt agg tac gga tac gat cca gcg ata aag gca     192
Cys Arg Ala Leu Phe Phe Arg Tyr Gly Tyr Asp Pro Ala Ile Lys Ala
 50                  55                  60 tgc aag gaa ttc atg tac ggc ggt tgc caa ggg aac gct aac aat ttc     240
Cys Lys Glu Phe Met Tyr Gly Gly Cys Gln Gly Asn Ala Asn Asn Phe
 65                  70                  75                  80 aag act tta gaa gaa tgc cag gaa gcc tgt gaa gcc taa gtacctggac      289
Lys Thr Leu Glu Glu Cys Gln Glu Ala Cys Glu Ala *
                85                  90 ttcg                                                                293

<210> SEQ ID NO 79
<211> LENGTH: 92
<212> TYPE: PRT
<213> ORGANISM: Manduca sexta

<400> SEQUENCE: 79

Met Asn Leu Leu Tyr Phe Leu Ser Phe Leu Gly Cys Ile Thr Leu Cys
 1               5                  10                  15

Leu Ser Ala Gly Leu Tyr Lys Pro Pro Asn Asn Ile Glu Ser Glu Asn
            20                  25                  30

Glu Val Tyr Thr Gly Asn Ile Cys Phe Leu Pro Leu Glu Val Gly Val
            35                  40                  45

Cys Arg Ala Leu Phe Phe Arg Tyr Gly Tyr Asp Pro Ala Ile Lys Ala
 50                  55                  60

Cys Lys Glu Phe Met Tyr Gly Gly Cys Gln Gly Asn Ala Asn Asn Phe
 65                  70                  75                  80

Lys Thr Leu Glu Glu Cys Gln Glu Ala Cys Glu Ala
                85                  90

<210> SEQ ID NO 80
```

```
<211> LENGTH: 92
<212> TYPE: PRT
<213> ORGANISM: Manduca sexta

<400> SEQUENCE: 80

Met Asn Leu Leu Tyr Phe Leu Ser Phe Leu Gly Cys Ile Thr Leu Cys
 1               5                  10                  15

Leu Ser Ala Gly Leu Tyr Lys Pro Pro Asn Asn Ile Glu Ser Glu Asn
            20                  25                  30

Glu Val Tyr Thr Gly Asn Ile Cys Phe Leu Pro Leu Glu Val Gly Val
        35                  40                  45

Cys Arg Ala Leu Phe Phe Arg Tyr Gly Tyr Asp Pro Ala Ile Lys Ala
    50                  55                  60

Cys Lys Glu Phe Met Tyr Gly Gly Cys Gln Gly Asn Ala Asn Asn Phe
65                  70                  75                  80

Lys Thr Leu Glu Glu Cys Gln Glu Ala Cys Glu Ala
                85                  90

<210> SEQ ID NO 81
<211> LENGTH: 489
<212> TYPE: DNA
<213> ORGANISM: Manduca sexta
<220> FEATURE:
<221> NAME/KEY: CDS
<222> LOCATION: (1)...(489)

<400> SEQUENCE: 81 atg aaa ttg cta ctg att ttg ggc gtt gcg ctg gtg ttg ctc ttt ggt      48
Met Lys Leu Leu Leu Ile Leu Gly Val Ala Leu Val Leu Leu Phe Gly
 1               5                  10                  15 gag tcc tta ggt cag cga ttt agc cag cct acg ttc aag cta cct caa      96
Glu Ser Leu Gly Gln Arg Phe Ser Gln Pro Thr Phe Lys Leu Pro Gln
            20                  25                  30 ggt aga ttg aca ctt agt cga aaa ttt agg gag tcc ggc aat gag cca     144
Gly Arg Leu Thr Leu Ser Arg Lys Phe Arg Glu Ser Gly Asn Glu Pro
        35                  40                  45 cta tgg ttg tat caa ggc gac aac ata cca aag gca cca tca act gca     192
Leu Trp Leu Tyr Gln Gly Asp Asn Ile Pro Lys Ala Pro Ser Thr Ala
    50                  55                  60 gaa cat ccc ttc ctt ccg tct ata ata gat gat gtg aag ttc aat cca     240
Glu His Pro Phe Leu Pro Ser Ile Ile Asp Asp Val Lys Phe Asn Pro
65                  70                  75                  80 gat aga aga tac gcg cgc agt ctt ggt aca cca gac cat tat cat gga     288
Asp Arg Arg Tyr Ala Arg Ser Leu Gly Thr Pro Asp His Tyr His Gly
                85                  90                  95 ggc cgt cat tcc ata tct cga ggt agc cag agc aca gga ccg act cat     336
Gly Arg His Ser Ile Ser Arg Gly Ser Gln Ser Thr Gly Pro Thr His
            100                 105                 110 ccg ggc tat aat cgc cgt aac gcc agg agt gtc gaa acg tta gct agc     384
Pro Gly Tyr Asn Arg Arg Asn Ala Arg Ser Val Glu Thr Leu Ala Ser
        115                 120                 125 caa gaa cat cta agc agc ctg ccg atg gat agc caa gag act tta ctg     432
Gln Glu His Leu Ser Ser Leu Pro Met Asp Ser Gln Glu Thr Leu Leu
    130                 135                 140 cgt ggc acc agg agc gtg gaa aca cta gct agt cag gaa cat cta agc     480
Arg Gly Thr Arg Ser Val Glu Thr Leu Ala Ser Gln Glu His Leu Ser
145                 150                 155                 160 agc ctg ccg                                                          489
Ser Leu Pro
```

```
<210> SEQ ID NO 82
<211> LENGTH: 163
<212> TYPE: PRT
<213> ORGANISM: Manduca sexta

<400> SEQUENCE: 82
```

Met Lys Leu Leu Leu Ile Leu Gly Val Ala Leu Val Leu Leu Phe Gly
1               5                   10                  15

Glu Ser Leu Gly Gln Arg Phe Ser Gln Pro Thr Phe Lys Leu Pro Gln
            20                  25                  30

Gly Arg Leu Thr Leu Ser Arg Lys Phe Arg Glu Ser Gly Asn Glu Pro
        35                  40                  45

Leu Trp Leu Tyr Gln Gly Asp Asn Ile Pro Lys Ala Pro Ser Thr Ala
    50                  55                  60

Glu His Pro Phe Leu Pro Ser Ile Ile Asp Asp Val Lys Phe Asn Pro
65                  70                  75                  80

Asp Arg Arg Tyr Ala Arg Ser Leu Gly Thr Pro Asp His Tyr His Gly
                85                  90                  95

Gly Arg His Ser Ile Ser Arg Gly Ser Gln Ser Thr Gly Pro Thr His
            100                 105                 110

Pro Gly Tyr Asn Arg Arg Asn Ala Arg Ser Val Glu Thr Leu Ala Ser
        115                 120                 125

Gln Glu His Leu Ser Ser Leu Pro Met Asp Ser Gln Glu Thr Leu Leu
    130                 135                 140

Arg Gly Thr Arg Ser Val Glu Thr Leu Ala Ser Gln Glu His Leu Ser
145                 150                 155                 160

Ser Leu Pro

```
<210> SEQ ID NO 83
<211> LENGTH: 165
<212> TYPE: PRT
<213> ORGANISM: Manduca sexta

<400> SEQUENCE: 83
```

Met Lys Leu Leu Leu Ile Leu Gly Val Ala Leu Val Leu Leu Phe Gly
1               5                   10                  15

Glu Ser Leu Gly Gln Arg Phe Ser Gln Pro Thr Phe Lys Leu Pro Gln
            20                  25                  30

Gly Arg Leu Thr Leu Ser Arg Lys Phe Arg Glu Ser Gly Asn Glu Pro
        35                  40                  45

Leu Trp Leu Tyr Gln Gly Asp Asn Ile Pro Lys Ala Pro Ser Thr Ala
    50                  55                  60

Glu His Pro Phe Leu Pro Ser Ile Ile Asp Asp Val Lys Phe Asn Pro
65                  70                  75                  80

Asp Arg Arg Tyr Ala Arg Ser Leu Gly Thr Pro Asp His Tyr His Gly
                85                  90                  95

Gly Arg His Ser Ile Ser Arg Gly Ser Gln Ser Thr Gly Pro Thr His
            100                 105                 110

Pro Gly Tyr Asn Arg Arg Asn Ala Arg Ser Val Glu Thr Leu Ala Ser
        115                 120                 125

Gln Glu His Leu Ser Ser Leu Pro Met Asp Ser Gln Glu Thr Leu Leu
    130                 135                 140

Arg Gly Thr Arg Ser Val Glu Thr Leu Ala Ser Gln Glu His Leu Ser
145                 150                 155                 160

Ser Leu Pro Met Asp
            165

```
<210> SEQ ID NO 84
<211> LENGTH: 475
<212> TYPE: DNA
<213> ORGANISM: Manduca sexta
<220> FEATURE:
<221> NAME/KEY: CDS
<222> LOCATION: (2)...(475)
<220> FEATURE:
<221> NAME/KEY: misc_feature
<222> LOCATION: 12, 13, 14
<223> OTHER INFORMATION: n = A,T,C or G

<400> SEQUENCE: 84 g ccg ctc tag ann ngt gga tcc ccc ggg ctg cag gca aaa tcc aat ttc       49
  Pro Leu  *  Xaa Xaa Gly Ser Pro Gly Leu Gln Ala Lys Ser Asn Phe
   1             5                  10                  15 gcg ctt gga gtt atc gca att ctg tta ata aca gaa tcc aac tgt tgg         97
Ala Leu Gly Val Ile Ala Ile Leu Leu Ile Thr Glu Ser Asn Cys Trp
             20                  25                  30 aga agt gat ctc cct atc ata ctc ccg act tat aaa cct cct cgt acc        145
Arg Ser Asp Leu Pro Ile Ile Leu Pro Thr Tyr Lys Pro Pro Arg Thr
         35                  40                  45 ccg agc acc att att atc agg aca gta cgc gaa gcc gga gat aaa ccg        193
Pro Ser Thr Ile Ile Ile Arg Thr Val Arg Glu Ala Gly Asp Lys Pro
     50                  55                  60 tta tgg ctc tac caa gga gac gat cac ccg caa gcc cct tca agc ggc        241
Leu Trp Leu Tyr Gln Gly Asp Asp His Pro Gln Ala Pro Ser Ser Gly
 65                  70                  75 gat cat cct gta ctg ccc tcg att ata gac gat gtg caa ctg gat ccc        289
Asp His Pro Val Leu Pro Ser Ile Ile Asp Asp Val Gln Leu Asp Pro
 80                  85                  90                  95 aac aga cgg tac gcg cgt agt gtg agc gag ccg tcg tct cag gat cat        337
Asn Arg Arg Tyr Ala Arg Ser Val Ser Glu Pro Ser Ser Gln Asp His
            100                 105                 110 cac gaa cgc ttt gtg agg agc ttc gac tcc cgc agc agc aag cat cac        385
His Glu Arg Phe Val Arg Ser Phe Asp Ser Arg Ser Ser Lys His His
        115                 120                 125 ggc ggc agt cac tcc acg tcc agc ggc agc cgc gac act gga gct act        433
Gly Gly Ser His Ser Thr Ser Ser Gly Ser Arg Asp Thr Gly Ala Thr
    130                 135                 140 cat ccg gga tac aat cgc cgt aac tca taa tct gtg gtt taa                475
His Pro Gly Tyr Asn Arg Arg Asn Ser  *  Ser Val Val  *
145                 150                 155

<210> SEQ ID NO 85
<211> LENGTH: 141
<212> TYPE: PRT
<213> ORGANISM: Manduca sexta

<400> SEQUENCE: 85

Lys Ser Asn Phe Ala Leu Gly Val Ile Ala Ile Leu Leu Ile Thr Glu
 1               5                  10                  15

Ser Asn Cys Trp Arg Ser Asp Leu Pro Ile Ile Leu Pro Thr Tyr Lys
            20                  25                  30

Pro Pro Arg Thr Pro Ser Thr Ile Ile Ile Arg Thr Val Arg Glu Ala
        35                  40                  45

Gly Asp Lys Pro Leu Trp Leu Tyr Gln Gly Asp Asp His Pro Gln Ala
    50                  55                  60

Pro Ser Ser Gly Asp His Pro Val Leu Pro Ser Ile Ile Asp Asp Val
65                  70                  75                  80
```

```
Gln Leu Asp Pro Asn Arg Arg Tyr Ala Arg Ser Val Ser Glu Pro Ser
                85                  90                  95

Ser Gln Asp His His Glu Arg Phe Val Arg Ser Phe Asp Ser Arg Ser
            100                 105                 110

Ser Lys His His Gly Gly Ser His Ser Thr Ser Ser Gly Ser Arg Asp
        115                 120                 125

Thr Gly Ala Thr His Pro Gly Tyr Asn Arg Arg Asn Ser
    130                 135                 140
```

<210> SEQ ID NO 86
<211> LENGTH: 155
<212> TYPE: PRT
<213> ORGANISM: Manduca sexta
<220> FEATURE:
<221> NAME/KEY: VARIANT
<222> LOCATION: 3, 4
<223> OTHER INFORMATION: Xaa = Any Amino Acid

<400> SEQUENCE: 86

```
Pro Leu Xaa Xaa Gly Ser Pro Gly Leu Gln Ala Lys Ser Asn Phe Ala
 1               5                  10                  15

Leu Gly Val Ile Ala Ile Leu Leu Ile Thr Glu Ser Asn Cys Trp Arg
            20                  25                  30

Ser Asp Leu Pro Ile Ile Leu Pro Thr Tyr Lys Pro Pro Arg Thr Pro
        35                  40                  45

Ser Thr Ile Ile Ile Arg Thr Val Arg Glu Ala Gly Asp Lys Pro Leu
    50                  55                  60

Trp Leu Tyr Gln Gly Asp Asp His Pro Gln Ala Pro Ser Ser Gly Asp
65                  70                  75                  80

His Pro Val Leu Pro Ser Ile Ile Asp Asp Val Gln Leu Asp Pro Asn
                85                  90                  95

Arg Arg Tyr Ala Arg Ser Val Ser Glu Pro Ser Ser Gln Asp His His
            100                 105                 110

Glu Arg Phe Val Arg Ser Phe Asp Ser Arg Ser Ser Lys His His Gly
        115                 120                 125

Gly Ser His Ser Thr Ser Ser Gly Ser Arg Asp Thr Gly Ala Thr His
    130                 135                 140

Pro Gly Tyr Asn Arg Arg Asn Ser Ser Val Val
145                 150                 155
```

<210> SEQ ID NO 87
<211> LENGTH: 273
<212> TYPE: DNA
<213> ORGANISM: Manduca sexta
<220> FEATURE:
<221> NAME/KEY: CDS
<222> LOCATION: (1)...(204)

<400> SEQUENCE: 87

```
atg aaa ttc tcc cgt gtt tta ttc ttc gtc ttc gct tgc ttc gcc gca      48
Met Lys Phe Ser Arg Val Leu Phe Phe Val Phe Ala Cys Phe Ala Ala
 1               5                  10                  15 ttt aca gta act gcg gcc aag cca tgg gac ttc tta aag gag ctg gag      96
Phe Thr Val Thr Ala Ala Lys Pro Trp Asp Phe Leu Lys Glu Leu Glu
            20                  25                  30 ggt gca ggt caa agg att cgt gac gct atc atc agc gcg cag ccg gcg     144
Gly Ala Gly Gln Arg Ile Arg Asp Ala Ile Ile Ser Ala Gln Pro Ala
        35                  40                  45 gtg gaa acc atc gcg cag gca acc gcc att ttc aaa gga caa tca aaa     192
Val Glu Thr Ile Ala Gln Ala Thr Ala Ile Phe Lys Gly Gln Ser Lys
```

-continued

```
                50                   55                   60 gaa gaa gat taa ttgtgtcatt acagtattac atatttaagg atataatttt      244
Glu Glu Asp *
 65 attttgacaa tatattcatt taattcaac                                   273

<210> SEQ ID NO 88
<211> LENGTH: 67
<212> TYPE: PRT
<213> ORGANISM: Manduca sexta

<400> SEQUENCE: 88

Met Lys Phe Ser Arg Val Leu Phe Phe Val Phe Ala Cys Phe Ala Ala
 1               5                  10                  15

Phe Thr Val Thr Ala Ala Lys Pro Trp Asp Phe Leu Lys Glu Leu Glu
            20                  25                  30

Gly Ala Gly Gln Arg Ile Arg Asp Ala Ile Ile Ser Ala Gln Pro Ala
        35                  40                  45

Val Glu Thr Ile Ala Gln Ala Thr Ala Ile Phe Lys Gly Gln Ser Lys
    50                  55                  60

Glu Glu Asp
 65

<210> SEQ ID NO 89
<211> LENGTH: 60
<212> TYPE: PRT
<213> ORGANISM: Manduca sexta

<400> SEQUENCE: 89

Met Lys Phe Ser Arg Val Leu Phe Phe Val Phe Ala Cys Phe Ala Ala
 1               5                  10                  15

Phe Thr Val Thr Ala Ala Lys Pro Trp Asp Phe Leu Lys Glu Leu Glu
            20                  25                  30

Gly Ala Gly Gln Arg Ile Arg Asp Ala Ile Ile Ser Ala Gln Pro Ala
        35                  40                  45

Val Glu Thr Ile Ala Gln Ala Thr Ala Ile Phe Lys
    50                  55                  60

<210> SEQ ID NO 90
<211> LENGTH: 418
<212> TYPE: DNA
<213> ORGANISM: Peregrinus maidis
<220> FEATURE:
<221> NAME/KEY: CDS
<222> LOCATION: (1)...(192)
<220> FEATURE:
<221> NAME/KEY: misc_feature
<222> LOCATION: 259, 305, 330, 340, 358, 359, 372, 380, 397, 417
<223> OTHER INFORMATION: n = A,T,C or G

<400> SEQUENCE: 90 atg aag ttc tcc cga gtg ttc ctg ttc gtg ttc gcg tgc ctg gtc gcg      48
Met Lys Phe Ser Arg Val Phe Leu Phe Val Phe Ala Cys Leu Val Ala
 1               5                  10                  15 ctg agc gcc gtc agc gcc gcg cca gag ccg agg tgg aag gtc ttc aag      96
Leu Ser Ala Val Ser Ala Ala Pro Glu Pro Arg Trp Lys Val Phe Lys
            20                  25                  30 aag att gag aag atg ggc cgc aac atc aga gac ggt atc gtc aag gca     144
Lys Ile Glu Lys Met Gly Arg Asn Ile Arg Asp Gly Ile Val Lys Ala
        35                  40                  45 ggt cct gct gtc gag gtg ttg ggt gca gcc aaa gcg ctg ggg aag taa     192
Gly Pro Ala Val Glu Val Leu Gly Ala Ala Lys Ala Leu Gly Lys *
```

```
Gly Pro Ala Val Glu Val Leu Gly Ala Ala Lys Ala Leu Gly Lys  *
        50                  55                  60 tcagcagtat catcttcatc atcatcactt aatatcatca caagtcttat ggtgtgacca    252
gcatatnctg gtgaccaaca acccctttaa attcctaaac ccaccaaaaa ggncgggtaa    312
cgcacttgtt acgcctcngg tgttttgnaa tgtccaaggg ggtggnnggc gattgcttan    372
ccatcaanaa tgattccttc tgatncgttt aaccggtaat ttccna                  418

<210> SEQ ID NO 91
<211> LENGTH: 63
<212> TYPE: PRT
<213> ORGANISM: Peregrinus maidis

<400> SEQUENCE: 91

Met Lys Phe Ser Arg Val Phe Leu Phe Val Phe Ala Cys Leu Val Ala
1               5                   10                  15

Leu Ser Ala Val Ser Ala Ala Pro Glu Pro Arg Trp Lys Val Phe Lys
            20                  25                  30

Lys Ile Glu Lys Met Gly Arg Asn Ile Arg Asp Gly Ile Val Lys Ala
        35                  40                  45

Gly Pro Ala Val Glu Val Leu Gly Ala Ala Lys Ala Leu Gly Lys
    50                  55                  60

<210> SEQ ID NO 92
<211> LENGTH: 63
<212> TYPE: PRT
<213> ORGANISM: Peregrinus maidis

<400> SEQUENCE: 92

Met Lys Phe Ser Arg Val Phe Leu Phe Val Phe Ala Cys Leu Val Ala
1               5                   10                  15

Leu Ser Ala Val Ser Ala Ala Pro Glu Pro Arg Trp Lys Val Phe Lys
            20                  25                  30

Lys Ile Glu Lys Met Gly Arg Asn Ile Arg Asp Gly Ile Val Lys Ala
        35                  40                  45

Gly Pro Ala Val Glu Val Leu Gly Ala Ala Lys Ala Leu Gly Lys
    50                  55                  60

<210> SEQ ID NO 93
<211> LENGTH: 370
<212> TYPE: DNA
<213> ORGANISM: Peregrinus maidis
<220> FEATURE:
<221> NAME/KEY: CDS
<222> LOCATION: (1)...(225)

<400> SEQUENCE: 93 atg aag ttc tcc cga gtg ttc ctg ttc gtg ttc gcg tgc ctg gtc gcg    48
Met Lys Phe Ser Arg Val Phe Leu Phe Val Phe Ala Cys Leu Val Ala
1               5                   10                  15 ctg agc gcc gtc agc gcc gcg cca gag ccg agg tgg aag gtc ttc aag    96
Leu Ser Ala Val Ser Ala Ala Pro Glu Pro Arg Trp Lys Val Phe Lys
            20                  25                  30 aag att gag aag atg ggc cgc aac atc aga gac ggt atc gtc aag gca    144
Lys Ile Glu Lys Met Gly Arg Asn Ile Arg Asp Gly Ile Val Lys Ala
        35                  40                  45 ggt cct gct gtc gag gtg ttg ggt gca agc caa ggc gct ggg gaa gta    192
Gly Pro Ala Val Glu Val Leu Gly Ala Ser Gln Gly Ala Gly Glu Val
    50                  55                  60 atc agc agt atc atc ttc atc atc atc act taa tatcatcaca gtcttatggt  245
```

```
Ile Ser Ser Ile Ile Phe Ile Ile Ile Thr    *
 65                  70 gtgaccagca tatctggtga caacaaccct taaattccta acccaccaaa agggcggtaa      305
cgcacttgtt acgcctcggg tgtttgaaat gtccaagggg tgggcggcga ttgcttacca      365
acaag                                                                 370

<210> SEQ ID NO 94
<211> LENGTH: 74
<212> TYPE: PRT
<213> ORGANISM: Peregrinus maidis

<400> SEQUENCE: 94

Met Lys Phe Ser Arg Val Phe Leu Phe Val Phe Ala Cys Leu Val Ala
 1               5                  10                  15

Leu Ser Ala Val Ser Ala Ala Pro Glu Pro Arg Trp Lys Val Phe Lys
            20                  25                  30

Lys Ile Glu Lys Met Gly Arg Asn Ile Arg Asp Gly Ile Val Lys Ala
        35                  40                  45

Gly Pro Ala Val Glu Val Leu Gly Ala Ser Gln Gly Ala Gly Glu Val
    50                  55                  60

Ile Ser Ser Ile Ile Phe Ile Ile Ile Thr
 65                  70

<210> SEQ ID NO 95
<211> LENGTH: 63
<212> TYPE: PRT
<213> ORGANISM: Peregrinus maidis

<400> SEQUENCE: 95

Met Lys Phe Ser Arg Val Phe Leu Phe Val Phe Ala Cys Leu Val Ala
 1               5                  10                  15

Leu Ser Ala Val Ser Ala Ala Pro Glu Pro Arg Trp Lys Val Phe Lys
            20                  25                  30

Lys Ile Glu Lys Met Gly Arg Asn Ile Arg Asp Gly Ile Val Lys Ala
        35                  40                  45

Gly Pro Ala Val Glu Val Leu Gly Ala Ser Gln Gly Ala Gly Glu
    50                  55                  60

<210> SEQ ID NO 96
<211> LENGTH: 12
<212> TYPE: PRT
<213> ORGANISM: Artificial Sequence
<220> FEATURE:
<223> OTHER INFORMATION: Peptide sequence from Lys-C digested Mag1

<400> SEQUENCE: 96

Val Gly Ala Ser Leu Gly Ala Ala His Thr Asp Phe
 1               5                  10

<210> SEQ ID NO 97
<211> LENGTH: 17
<212> TYPE: PRT
<213> ORGANISM: Artificial Sequence
<220> FEATURE:
<223> OTHER INFORMATION: Peptide sequence from Lys-C digested Mag1

<400> SEQUENCE: 97

Asn Asn Ile Phe Ser Ala Ile Gly Gly Ala Asp Phe Asn Ala Asn His
 1               5                  10                  15

Lys
```

<210> SEQ ID NO 98
<211> LENGTH: 12
<212> TYPE: PRT
<213> ORGANISM: Artificial Sequence
<220> FEATURE:
<223> OTHER INFORMATION: Peptide sequence from Lys-C digested Mag1

<400> SEQUENCE: 98

Lys Phe Asp Thr Pro Phe Met Arg Ser Gly Trp Glu
 1               5                  10

<210> SEQ ID NO 99
<211> LENGTH: 12
<212> TYPE: PRT
<213> ORGANISM: Artificial Sequence
<220> FEATURE:
<223> OTHER INFORMATION: Peptide sequence from Lys-C digested Mag1

<400> SEQUENCE: 99

Leu Asn Leu Phe His Asn Asn His Asp Leu Thr
 1               5                  10

<210> SEQ ID NO 100
<211> LENGTH: 358
<212> TYPE: DNA
<213> ORGANISM: Agrotis ipsilon
<220> FEATURE:
<221> NAME/KEY: CDS
<222> LOCATION: (1)...(195)
<220> FEATURE:
<221> NAME/KEY: misc_feature
<222> LOCATION: (0)...(0)
<223> OTHER INFORMATION: Fus6

<400> SEQUENCE: 100

```
atg gcc gcc aac aag act atc ttc ctt ctc gtg ctg atc gcc ttc gca      48
Met Ala Ala Asn Lys Thr Ile Phe Leu Leu Val Leu Ile Ala Phe Ala
 1               5                  10                  15 atg gtg atg gtg acc gtg gag gcc gtc cgt gtg gga ccc tgc gac cag      96
Met Val Met Val Thr Val Glu Ala Val Arg Val Gly Pro Cys Asp Gln
                20                  25                  30 gtc tgc agc cgc atc gat gct gag aag aac gag tgc tgc aga gct cac     144
Val Cys Ser Arg Ile Asp Ala Glu Lys Asn Glu Cys Cys Arg Ala His
            35                  40                  45 ggc tac tcc gga tac agc agc tgt aga tat ggg cag atg caa tgt tac     192
Gly Tyr Ser Gly Tyr Ser Ser Cys Arg Tyr Gly Gln Met Gln Cys Tyr
        50                  55                  60 tga cggaactcca caagagcaac agttttctaa ccacttttc aactttgtcc           245
  * agaggtaatc aagattgcct catcacttca aggttctttt tttgtcattt attaacttgt   305
tttcaaaatt aaccgattaa attaattaat ttaaaaaaaa aaaaaaaaaa aaa          358
```

<210> SEQ ID NO 101
<211> LENGTH: 64
<212> TYPE: PRT
<213> ORGANISM: Agrotis ipsilon

<400> SEQUENCE: 101

Met Ala Ala Asn Lys Thr Ile Phe Leu Leu Val Leu Ile Ala Phe Ala
 1               5                  10                  15

Met Val Met Val Thr Val Glu Ala Val Arg Val Gly Pro Cys Asp Gln
                20                  25                  30

```
Val Cys Ser Arg Ile Asp Ala Glu Lys Asn Glu Cys Cys Arg Ala His
         35                  40                  45

Gly Tyr Ser Gly Tyr Ser Cys Arg Tyr Gly Gln Met Gln Cys Tyr
 50                  55                  60
```

<210> SEQ ID NO 102
<211> LENGTH: 123
<212> TYPE: DNA
<213> ORGANISM: Agrotis ipsilon
<220> FEATURE:
<221> NAME/KEY: CDS
<222> LOCATION: (1)...(123)
<220> FEATURE:
<221> NAME/KEY: misc_feature
<222> LOCATION: (0)...(0)
<223> OTHER INFORMATION: Fus6

<400> SEQUENCE: 102

```
gtc cgt gtg gga ccc tgc gac cag gtc tgc agc cgc atc gat gct gag      48
Val Arg Val Gly Pro Cys Asp Gln Val Cys Ser Arg Ile Asp Ala Glu
 1               5                  10                  15 aag aac gag tgc tgc aga gct cac ggc tac tcc gga tac agc agc tgt      96
Lys Asn Glu Cys Cys Arg Ala His Gly Tyr Ser Gly Tyr Ser Ser Cys
             20                  25                  30 aga tat ggg cag atg caa tgt tac tga                                 123
Arg Tyr Gly Gln Met Gln Cys Tyr  *
         35                  40
```

<210> SEQ ID NO 103
<211> LENGTH: 40
<212> TYPE: PRT
<213> ORGANISM: Agrotis ipsilon

<400> SEQUENCE: 103

```
Val Arg Val Gly Pro Cys Asp Gln Val Cys Ser Arg Ile Asp Ala Glu
 1               5                  10                  15

Lys Asn Glu Cys Cys Arg Ala His Gly Tyr Ser Gly Tyr Ser Ser Cys
             20                  25                  30

Arg Tyr Gly Gln Met Gln Cys Tyr
         35                  40
```

<210> SEQ ID NO 104
<211> LENGTH: 387
<212> TYPE: DNA
<213> ORGANISM: Agrotis ipsilon
<220> FEATURE:
<221> NAME/KEY: CDS
<222> LOCATION: (1)...(195)
<220> FEATURE:
<221> NAME/KEY: misc_feature
<222> LOCATION: (0)...(0)
<223> OTHER INFORMATION: Fus7

<400> SEQUENCE: 104

```
atg gtt gcc aac aag act atc ctc ctt ctc gtg ctg atc gcc ttc gca      48
Met Val Ala Asn Lys Thr Ile Leu Leu Leu Val Leu Ile Ala Phe Ala
 1               5                  10                  15 atg gtg atg gtg acc gtg gaa gcc gtc cat gtg gga ccc tgc gac cag      96
Met Val Met Val Thr Val Glu Ala Val His Val Gly Pro Cys Asp Gln
             20                  25                  30 gtc tgc agc cgc atc gac gct gag aag gac gag tgc tgc aga gct cac     144
Val Cys Ser Arg Ile Asp Ala Glu Lys Asp Glu Cys Cys Arg Ala His
         35                  40                  45 ggc cac tcc ggc tac agc agc tgc aga tac gga cag atg caa tgt tac     192
Gly His Ser Gly Tyr Ser Ser Cys Arg Tyr Gly Gln Met Gln Cys Tyr
```

```
          50                  55                  60
tga cggtactccg caacaacaac ggtactatag tggagctatt gtgtaacttt       245
  * tccaaataca tgtgaaagtt aactgtgata tttttaagtt cctttacttt tgaattcggc  305
atgtgattaa gttattgttt aataaaagga attatttatg aaaaaaaaaa aaaaaaaaa   365 aaaaaaaaaa aaaaaaaaaa aa                                          387
```

<210> SEQ ID NO 105
<211> LENGTH: 64
<212> TYPE: PRT
<213> ORGANISM: Agrotis ipsilon

<400> SEQUENCE: 105

Met Val Ala Asn Lys Thr Ile Leu Leu Val Leu Ile Ala Phe Ala
1               5                   10                  15

Met Val Met Val Thr Val Glu Ala Val His Val Gly Pro Cys Asp Gln
                20                  25                  30

Val Cys Ser Arg Ile Asp Ala Glu Lys Asp Glu Cys Cys Arg Ala His
            35                  40                  45

Gly His Ser Gly Tyr Ser Ser Cys Arg Tyr Gly Gln Met Gln Cys Tyr
        50                  55                  60

<210> SEQ ID NO 106
<211> LENGTH: 123
<212> TYPE: DNA
<213> ORGANISM: Agrotis ipsilon
<220> FEATURE:
<221> NAME/KEY: CDS
<222> LOCATION: (1)...(123)
<220> FEATURE:
<221> NAME/KEY: misc_feature
<222> LOCATION: (0)...(0)
<223> OTHER INFORMATION: Fus7

<400> SEQUENCE: 106

```
gtc cat gtg gga ccc tgc gac cag gtc tgc agc cgc atc gac gct gag    48
Val His Val Gly Pro Cys Asp Gln Val Cys Ser Arg Ile Asp Ala Glu
1               5                   10                  15 aag gac gag tgc tgc aga gct cac ggc cac tcc ggc tac agc agc tgc    96
Lys Asp Glu Cys Cys Arg Ala His Gly His Ser Gly Tyr Ser Ser Cys
                20                  25                  30 aga tac gga cag atg caa tgt tac tga                                123
Arg Tyr Gly Gln Met Gln Cys Tyr *
            35                  40
```

<210> SEQ ID NO 107
<211> LENGTH: 40
<212> TYPE: PRT
<213> ORGANISM: Agrotis ipsilon

<400> SEQUENCE: 107

Val His Val Gly Pro Cys Asp Gln Val Cys Ser Arg Ile Asp Ala Glu
1               5                   10                  15

Lys Asp Glu Cys Cys Arg Ala His Gly His Ser Gly Tyr Ser Ser Cys
                20                  25                  30

Arg Tyr Gly Gln Met Gln Cys Tyr
            35                  40

<210> SEQ ID NO 108
<211> LENGTH: 361
<212> TYPE: DNA

<213> ORGANISM: Agrotis ipsilon
<220> FEATURE:
<221> NAME/KEY: CDS
<222> LOCATION: (1)...(195)
<220> FEATURE:
<221> NAME/KEY: misc_feature
<222> LOCATION: (0)...(0)
<223> OTHER INFORMATION: Fus8
<220> FEATURE:
<221> NAME/KEY: misc_feature
<222> LOCATION: 327, 328, 329, 330, 331, 332, 333
<223> OTHER INFORMATION: n = A,T,C or G

<400> SEQUENCE: 108

```
atg gtt gcc aac aag acc atc ttc ctt ctc gtg ctg atc gcc ttc gca      48
Met Val Ala Asn Lys Thr Ile Phe Leu Leu Val Leu Ile Ala Phe Ala
1               5                   10                  15 atg gtg atg gtg acc gtg gag gcc gtc cgt gtg gga ccc tgc gac cag      96
Met Val Met Val Thr Val Glu Ala Val Arg Val Gly Pro Cys Asp Gln
            20                  25                  30 gtc tgc agc cgc atc gac gct gag aag gac gag tgc tgc aga gct cac     144
Val Cys Ser Arg Ile Asp Ala Glu Lys Asp Glu Cys Cys Arg Ala His
        35                  40                  45 ggc cac tcc ggc tac agc agc tgc aga tac gga cag atg caa tgt tac     192
Gly His Ser Gly Tyr Ser Ser Cys Arg Tyr Gly Gln Met Gln Cys Tyr
    50                  55                  60 tga cggaactccg caacgacaac ggtactatag tggagctact gtgtaacttc          245
 * tctaaatttc tattactttc gaattcggca tgtgataaag ttattgttta ataaaggaa    305 ttatttataa aaaaaaaaaa annnnnnnaa aaaaaaaaa aaaaaaaaaa aaaaaa        361
```

<210> SEQ ID NO 109
<211> LENGTH: 64
<212> TYPE: PRT
<213> ORGANISM: Agrotis ipsilon

<400> SEQUENCE: 109

```
Met Val Ala Asn Lys Thr Ile Phe Leu Leu Val Leu Ile Ala Phe Ala
1               5                   10                  15

Met Val Met Val Thr Val Glu Ala Val Arg Val Gly Pro Cys Asp Gln
            20                  25                  30

Val Cys Ser Arg Ile Asp Ala Glu Lys Asp Glu Cys Cys Arg Ala His
        35                  40                  45

Gly His Ser Gly Tyr Ser Ser Cys Arg Tyr Gly Gln Met Gln Cys Tyr
    50                  55                  60
```

<210> SEQ ID NO 110
<211> LENGTH: 123
<212> TYPE: DNA
<213> ORGANISM: Agrotis ipsilon
<220> FEATURE:
<221> NAME/KEY: CDS
<222> LOCATION: (1)...(123)
<220> FEATURE:
<221> NAME/KEY: misc_feature
<222> LOCATION: (0)...(0)
<223> OTHER INFORMATION: Fus8

<400> SEQUENCE: 110

```
gtc cgt gtg gga ccc tgc gac cag gtc tgc agc cgc atc gac gct gag      48
Val Arg Val Gly Pro Cys Asp Gln Val Cys Ser Arg Ile Asp Ala Glu
1               5                   10                  15 aag gac gag tgc tgc aga gct cac ggc cac tcc ggc tac agc agc tgc     96
Lys Asp Glu Cys Cys Arg Ala His Gly His Ser Gly Tyr Ser Ser Cys
```

```
                    20                  25                  30
aga tac gga cag atg caa tgt tac tga                                     123
Arg Tyr Gly Gln Met Gln Cys Tyr *
         35                  40

<210> SEQ ID NO 111
<211> LENGTH: 40
<212> TYPE: PRT
<213> ORGANISM: Agrotis ipsilon

<400> SEQUENCE: 111

Val Arg Val Gly Pro Cys Asp Gln Val Cys Ser Arg Ile Asp Ala Glu
 1               5                  10                  15

Lys Asp Glu Cys Cys Arg Ala His Gly His Ser Gly Tyr Ser Ser Cys
             20                  25                  30

Arg Tyr Gly Gln Met Gln Cys Tyr
         35                  40

<210> SEQ ID NO 112
<211> LENGTH: 466
<212> TYPE: DNA
<213> ORGANISM: Agrotis ipsilon
<220> FEATURE:
<221> NAME/KEY: CDS
<222> LOCATION: (1)...(291)
<220> FEATURE:
<221> NAME/KEY: misc_feature
<222> LOCATION: (0)...(0)
<223> OTHER INFORMATION: Fus9

<400> SEQUENCE: 112 atg aac aag caa ctg tta gtc gtc ctt ttg gcc atg tgc ctt gtc agc        48
Met Asn Lys Gln Leu Leu Val Val Leu Leu Ala Met Cys Leu Val Ser
 1               5                  10                  15 gct cac gct ttc gtg aaa cgc gat gtc cca aca aat gca gac tta cag        96
Ala His Ala Phe Val Lys Arg Asp Val Pro Thr Asn Ala Asp Leu Gln
             20                  25                  30 gga caa cta gaa gcc ttg aga aac acc ctt aat cag tta acc aac tca       144
Gly Gln Leu Glu Ala Leu Arg Asn Thr Leu Asn Gln Leu Thr Asn Ser
         35                  40                  45 gtc att aat caa act tca act gtt ttc gac ccg gaa gaa att aag aag       192
Val Ile Asn Gln Thr Ser Thr Val Phe Asp Pro Glu Glu Ile Lys Lys
     50                  55                  60 aat atc gat aaa gcc att gac aca gct agc aaa gcc att gat agt tta       240
Asn Ile Asp Lys Ala Ile Asp Thr Ala Ser Lys Ala Ile Asp Ser Leu
 65                  70                  75                  80 gtg aaa cca caa gga gga gaa gcc cag ccc gct gcc cag cca gca gcc       288
Val Lys Pro Gln Gly Gly Glu Ala Gln Pro Ala Ala Gln Pro Ala Ala
                 85                  90                  95 taa ttttatgttt aagactgatt tttatgacca cataaaatac ctcaaataaa            341
* acatcaaaat taatctgctt cttcctatct ttcagaaaac taaattaaat aaataattta    401
tacgtctgct taaaaaaaaa aaaaaaaaaa aaaaaaaaaa aaaaaaaaaa aaaaaaaaaa    461
aaaaa                                                                466

<210> SEQ ID NO 113
<211> LENGTH: 96
<212> TYPE: PRT
<213> ORGANISM: Agrotis ipsilon

<400> SEQUENCE: 113
```

```
Met Asn Lys Gln Leu Leu Val Leu Leu Ala Met Cys Leu Val Ser
 1               5                  10                  15

Ala His Ala Phe Val Lys Arg Asp Val Pro Thr Asn Ala Asp Leu Gln
                 20                  25                  30

Gly Gln Leu Glu Ala Leu Arg Asn Thr Leu Asn Gln Leu Thr Asn Ser
             35                  40                  45

Val Ile Asn Gln Thr Ser Thr Val Phe Asp Pro Glu Glu Ile Lys Lys
 50                  55                  60

Asn Ile Asp Lys Ala Ile Asp Thr Ala Ser Lys Ala Ile Asp Ser Leu
 65                  70                  75                  80

Val Lys Pro Gln Gly Gly Glu Ala Gln Pro Ala Ala Gln Pro Ala Ala
                 85                  90                  95
```

<210> SEQ ID NO 114
<211> LENGTH: 222
<212> TYPE: DNA
<213> ORGANISM: Agrotis ipsilon
<220> FEATURE:
<221> NAME/KEY: CDS
<222> LOCATION: (1)...(222)
<220> FEATURE:
<221> NAME/KEY: misc_feature
<222> LOCATION: (0)...(0)
<223> OTHER INFORMATION: Fus9

<400> SEQUENCE: 114

```
gat gtc cca aca aat gca gac tta cag gga caa cta gaa gcc ttg aga      48
Asp Val Pro Thr Asn Ala Asp Leu Gln Gly Gln Leu Glu Ala Leu Arg
 1               5                  10                  15 aac acc ctt aat cag tta acc aac tca gtc att aat caa act tca act      96
Asn Thr Leu Asn Gln Leu Thr Asn Ser Val Ile Asn Gln Thr Ser Thr
                 20                  25                  30 gtt ttc gac ccg gaa gaa att aag aag aat atc gat aaa gcc att gac     144
Val Phe Asp Pro Glu Glu Ile Lys Lys Asn Ile Asp Lys Ala Ile Asp
             35                  40                  45 aca gct agc aaa gcc att gat agt tta gtg aaa cca caa gga gga gaa     192
Thr Ala Ser Lys Ala Ile Asp Ser Leu Val Lys Pro Gln Gly Gly Glu
 50                  55                  60 gcc cag ccc gct gcc cag cca gca gcc taa                              222
Ala Gln Pro Ala Ala Gln Pro Ala Ala *
 65                  70
```

<210> SEQ ID NO 115
<211> LENGTH: 73
<212> TYPE: PRT
<213> ORGANISM: Agrotis ipsilon

<400> SEQUENCE: 115

```
Asp Val Pro Thr Asn Ala Asp Leu Gln Gly Gln Leu Glu Ala Leu Arg
 1               5                  10                  15

Asn Thr Leu Asn Gln Leu Thr Asn Ser Val Ile Asn Gln Thr Ser Thr
                 20                  25                  30

Val Phe Asp Pro Glu Glu Ile Lys Lys Asn Ile Asp Lys Ala Ile Asp
             35                  40                  45

Thr Ala Ser Lys Ala Ile Asp Ser Leu Val Lys Pro Gln Gly Gly Glu
 50                  55                  60

Ala Gln Pro Ala Ala Gln Pro Ala Ala
 65                  70
```

<210> SEQ ID NO 116
<211> LENGTH: 372

<212> TYPE: DNA
<213> ORGANISM: Agrotis ipsilon
<220> FEATURE:
<221> NAME/KEY: CDS
<222> LOCATION: (1)...(222)
<220> FEATURE:
<221> NAME/KEY: misc_feature
<222> LOCATION: (0)...(0)
<223> OTHER INFORMATION: Fus10
<220> FEATURE:
<221> NAME/KEY: misc_feature
<222> LOCATION: 242
<223> OTHER INFORMATION: n = A,T,C or G

<400> SEQUENCE: 116

```
atg tcg aaa agc tac cag tcc gtg ttg ttg ttg gtg tgc ctc acg ttc      48
Met Ser Lys Ser Tyr Gln Ser Val Leu Leu Leu Val Cys Leu Thr Phe
 1               5                  10                  15 ctg gtg atc gtc tcg tct ccg cag aat gct gtc cag gct gat gta cac      96
Leu Val Ile Val Ser Ser Pro Gln Asn Ala Val Gln Ala Asp Val His
             20                  25                  30 atc ggc agc tgc gtg tgg gga gct gtt gac tac act tcg aac tgc aac     144
Ile Gly Ser Cys Val Trp Gly Ala Val Asp Tyr Thr Ser Asn Cys Asn
         35                  40                  45 aat gaa tgc aag cgg cgt gga tac aaa gga gga cat tgt gga agc ttc     192
Asn Glu Cys Lys Arg Arg Gly Tyr Lys Gly Gly His Cys Gly Ser Phe
     50                  55                  60 gct aat gtt aat tgt tgg tgt gaa caa tag gacaacaatt taacattagn      242
Ala Asn Val Asn Cys Trp Cys Glu Gln *
 65                  70 acactaaaca aaccatcaaa atttgcagac gtggacacct ttcatagttt ttatacctttg  302 tcactatggt ggatggacta tcaaaatggt tcatgatttt gaaatttgta tctttaatct  362
cggactgatg                                                          372
```

<210> SEQ ID NO 117
<211> LENGTH: 73
<212> TYPE: PRT
<213> ORGANISM: Agrotis ipsilon

<400> SEQUENCE: 117

```
Met Ser Lys Ser Tyr Gln Ser Val Leu Leu Leu Val Cys Leu Thr Phe
 1               5                  10                  15

Leu Val Ile Val Ser Ser Pro Gln Asn Ala Val Gln Ala Asp Val His
             20                  25                  30

Ile Gly Ser Cys Val Trp Gly Ala Val Asp Tyr Thr Ser Asn Cys Asn
         35                  40                  45

Asn Glu Cys Lys Arg Arg Gly Tyr Lys Gly Gly His Cys Gly Ser Phe
     50                  55                  60

Ala Asn Val Asn Cys Trp Cys Glu Gln
 65                  70
```

<210> SEQ ID NO 118
<211> LENGTH: 135
<212> TYPE: DNA
<213> ORGANISM: Agrotis ipsilon
<220> FEATURE:
<221> NAME/KEY: CDS
<222> LOCATION: (1)...(135)
<220> FEATURE:
<221> NAME/KEY: misc_feature
<222> LOCATION: (0)...(0)
<223> OTHER INFORMATION: Fus10

<400> SEQUENCE: 118

```
gat gta cac atc ggc agc tgc gtg tgg gga gct gtt gac tac act

```
<213> ORGANISM: Artificial Sequence
<220> FEATURE:
<221> NAME/KEY: SIGNAL
<222> LOCATION: (1)...(24)
<223> OTHER INFORMATION: Codon biased nucleotide sequence encoding
      BAA-Fus1.  Codon biased to Manduca sexta.

<400> SEQUENCE: 121

Met Ala Asn Lys His Leu Ser Leu Ser Leu Phe Leu Val Leu Leu Gly
                -20                 -15                 -10

Leu Ser Ala Ser Leu Ala Ser Gly Glu Asp Pro Arg Cys Ser Gln

```
             10                  15                  20
Ile Asp Glu His Lys Cys Val Gln Phe Val Tyr Gly Gly Cys Phe Gly
 25                  30                  35                  40

Asn Asp Asn Gln Phe Asp Ser Leu Glu Glu Cys Gln Ala Val Cys Pro
                 45                  50                  55
```

<210> SEQ ID NO 124
<211> LENGTH: 207
<212> TYPE: DNA
<213> ORGANISM: Artificial Sequence
<220> FEATURE:
<223> OTHER INFORMATION: Codon biased nucleotide sequence encoding
      BAA-Fus2.  Codon biased to Streptomyces
      coelicolor.
<220> FEATURE:
<221> NAME/KEY: CDS
<222> LOCATION: (1)...(207)
<220> FEATURE:
<221> NAME/KEY: sig_peptide
<222> LOCATION: (1)...(75)
<223> OTHER INFORMATION: BAA signal sequence
<220> FEATURE:
<221> NAME/KEY: misc_feature
<222> LOCATION: (0)...(0)
<223> OTHER INFORMATION: BAA-Fus2

<400> SEQUENCE: 124

```
atg gcg aac aag cac ctg tcc ctc tcc ctc ttc ctg gtc ctg ctg ggc      48
Met Ala Asn Lys His Leu Ser Leu Ser Leu Phe Leu Val Leu Leu Gly
-25                  -20                  -15                  -10 ctc tcg gcg acc ccg tcc gcc cag gcg gac gcc ggc gac gag ccg ctg      96
Leu Ser Ala Thr Pro Ser Ala Gln Ala Asp Ala Gly Asp Glu Pro Leu
                 -5                   1                   5 tgg ctg tac cag ggc gac gac cac ccc aga gcc ccg agc agc ggg gac     144
Trp Leu Tyr Gln Gly Asp Asp His Pro Arg Ala Pro Ser Ser Gly Asp
         10                  15                  20 cac ccg gtg ctc ccc tcg atc atc gac gac gtc aag ctg gac ccc aac     192
His Pro Val Leu Pro Ser Ile Ile Asp Asp Val Lys Leu Asp Pro Asn
     25                  30                  35 cgg cgc tac gcc tga                                                  207
Arg Arg Tyr Ala *
 40
```

<210> SEQ ID NO 125
<211> LENGTH: 68
<212> TYPE: PRT
<213> ORGANISM: Artificial Sequence
<220> FEATURE:
<221> NAME/KEY: SIGNAL
<222> LOCATION: (1)...(25)
<223> OTHER INFORMATION: Codon biased nucleotide sequence encoding
      BAA-Fus2.  Codon biased to Streptomyces
      coelicolor.

<400> SEQUENCE: 125

```
Met Ala Asn Lys His Leu Ser Leu Ser Leu Phe Leu Val Leu Leu Gly
-25                  -20                  -15                  -10

Leu Ser Ala Thr Pro Ser Ala Gln Ala Asp Ala Gly Asp Glu Pro Leu
                 -5                   1                   5

Trp Leu Tyr Gln Gly Asp Asp His Pro Arg Ala Pro Ser Ser Gly Asp
         10                  15                  20

His Pro Val Leu Pro Ser Ile Ile Asp Asp Val Lys Leu Asp Pro Asn
     25                  30                  35

Arg Arg Tyr Ala
 40
```

<210> SEQ ID NO 126
<211> LENGTH: 132
<212> TYPE: DNA
<213> ORGANISM: Artificial Sequence
<220> FEATURE:
<223> OTHER INFORMATION: Codon biased nucleotide sequence encoding Fus2.
    Codon biased to Streptomyces coelicolor.
<220> FEATURE:
<221> NAME/KEY: CDS
<222> LOCATION: (1)...(132)
<220> FEATURE:
<221> NAME/KEY: misc_feature
<222> LOCATION: (0)...(0)
<223> OTHER INFORMATION: Fus2

<400> SEQUENCE: 126

```
gac gcc ggc gac gag ccg ctg tgg ctg tac cag ggc gac gac cac ccc     48
Asp Ala Gly Asp Glu Pro Leu Trp Leu Tyr Gln Gly Asp Asp His Pro
 1               5                  10                  15 aga gcc ccg agc agc ggg gac cac ccg gtg ctc ccc tcg atc atc gac     96
Arg Ala Pro Ser Ser Gly Asp His Pro Val Leu Pro Ser Ile Ile Asp
                20                  25                  30 gac gtc aag ctg gac ccc aac cgg cgc tac gcc tga                    132
Asp Val Lys Leu Asp Pro Asn Arg Arg Tyr Ala *
            35                  40
```

<210> SEQ ID NO 127
<211> LENGTH: 68
<212> TYPE: PRT
<213> ORGANISM: Artificial Sequence
<220> FEATURE:
<223> OTHER INFORMATION: Codon biased nucleotide sequence encoding
    BAA-Fus2. Codon biased to Streptomyces
    coelicolor.
<220> FEATURE:
<221> NAME/KEY: SIGNAL
<222> LOCATION: (1)...(25)
<223> OTHER INFORMATION: BAA

<400> SEQUENCE: 127

```
Met Ala Asn Lys His Leu Ser Leu Ser Leu Phe Leu Val Leu Leu Gly
-25                 -20                 -15                 -10

Leu Ser Ala Thr Pro Ser Ala Gln Ala Asp Ala Gly Asp Glu Pro Leu
                -5                   1                   5

Trp Leu Tyr Gln Gly Asp Asp His Pro Arg Ala Pro Ser Ser Gly Asp
            10                  15                  20

His Pro Val Leu Pro Ser Ile Ile Asp Val Lys Leu Asp Pro Asn
    25                  30                  35

Arg Arg Tyr Ala
40
```